(12) United States Patent
Reynolds et al.

(10) Patent No.: US 11,666,549 B2
(45) Date of Patent: **\*Jun. 6, 2023**

(54) REGULATION OF CANCER USING NATURAL COMPOUNDS AND/OR DIET

(71) Applicant: UNIVERSITY OF FLORIDA RESEARCH FOUNDATION, INC., Gainesville, FL (US)

(72) Inventors: Brent Allan Reynolds, Gainesville, FL (US); Loic Pierre Deleyrolle, Gainesville, FL (US)

(73) Assignee: UNIVERSITY OF FLORIDA RESEARCH FOUNDATION, INCORPORATED, Gainesville, FL (US)

(*) Notice: Subject to any disclaimer, the term of this patent is extended or adjusted under 35 U.S.C. 154(b) by 96 days.

This patent is subject to a terminal disclaimer.

(21) Appl. No.: 16/860,153

(22) Filed: Apr. 28, 2020

(65) Prior Publication Data

US 2021/0008024 A1    Jan. 14, 2021

Related U.S. Application Data

(62) Division of application No. 14/775,751, filed as application No. PCT/US2014/023934 on Mar. 12, 2014, now abandoned.

(60) Provisional application No. 61/784,386, filed on Mar. 14, 2013.

(51) Int. Cl.
| | |
|---|---|
| *A61K 31/352* | (2006.01) |
| *A61K 45/06* | (2006.01) |
| *A61K 31/7028* | (2006.01) |
| *A61K 36/31* | (2006.01) |
| *A61K 31/12* | (2006.01) |
| *A61K 31/26* | (2006.01) |
| *A61K 31/353* | (2006.01) |
| *A23L 29/00* | (2016.01) |

(52) U.S. Cl.
CPC .......... *A61K 31/352* (2013.01); *A23L 29/035* (2016.08); *A23L 29/055* (2016.08); *A61K 31/12* (2013.01); *A61K 31/26* (2013.01); *A61K 31/353* (2013.01); *A61K 31/7028* (2013.01); *A61K 36/31* (2013.01); *A61K 45/06* (2013.01); *A23V 2002/00* (2013.01)

(58) Field of Classification Search
CPC ....... A61K 31/12; A61K 31/26; A61K 31/352
See application file for complete search history.

(56) References Cited

U.S. PATENT DOCUMENTS

| | | | |
|---|---|---|---|
| 7,303,770 B2 | 12/2007 | Fahey et al. | |
| 7,968,115 B2 | 6/2011 | Kurzrock et al. | |
| 8,252,831 B2 | 8/2012 | Kuki et al. | |
| 11,020,372 B2* | 6/2021 | Deleyrolle | A61K 31/26 |
| 2009/0143433 A1 | 6/2009 | Hendrix | |
| 2009/0252796 A1 | 10/2009 | Mazed et al. | |
| 2011/0014137 A1 | 1/2011 | Talalay et al. | |
| 2013/0280357 A1 | 10/2013 | Coy | |
| 2013/0287871 A1 | 10/2013 | Coy | |
| 2013/0310457 A1 | 11/2013 | Ramesh | |
| 2014/0193480 A1 | 7/2014 | McWherter et al. | |
| 2014/0275235 A1 | 9/2014 | Deleyrolle et al. | |
| 2014/0350105 A1 | 11/2014 | D'Agostino et al. | |
| 2015/0118306 A1 | 4/2015 | Cornblatt et al. | |
| 2016/0279094 A1 | 9/2016 | Deleyrolle et al. | |
| 2018/0133194 A1 | 5/2018 | Deleyrolle et al. | |

FOREIGN PATENT DOCUMENTS

| | | | |
|---|---|---|---|
| JP | H1149793 | 2/1999 | |
| JP | 2007-153834 | 6/2007 | |
| WO | WO 2012/092916 | 7/2012 | |
| WO | WO 2012/092917 | 7/2012 | |
| WO | WO 2012/113572 | 8/2012 | |
| WO | WO 2012/122295 | 9/2012 | |
| WO | WO 2012/142511 | 10/2012 | |
| WO | WO-2012159085 A2 * | 11/2012 | A61K 31/05 |
| WO | WO 2013/186570 | 12/2013 | |
| WO | WO 2014/008366 | 1/2014 | |
| WO | WO 2014/168736 | 10/2014 | |

(Continued)

OTHER PUBLICATIONS

Yunos et al. Anticancer Research, 2011, vol. 31, pp. 1131-1140 (Year: 2011).*

(Continued)

*Primary Examiner* — James D. Anderson
(74) *Attorney, Agent, or Firm* — Timothy H. Van Dyke; Wolter, Van Dyke, Davis, PLLC

(57) ABSTRACT

The current invention is directed to a treatment of a proliferative disease comprising administering to a subject in need of such treatment, a composition comprising epigallocatechin-3-gallate (EGCG), curcumin, glucosinolates and, optionally Daikon radish sprout, alone or in combination with providing a ketogenic diet or a modified ketogenic diet to the subject. The invention also provides a composition comprising medium chain triglycerides, Epigallocatechin-3-gallate, curcumin, compositions comprising glucosinolates and/or derivatives thereof, such as glucoraphanin and its breakdown product sulforaphane, (SFN) (which are found at high levels in broccoli sprouts or sprouts of other cruciferous vegetables), and, optionally Daikon radish sprout.

14 Claims, 39 Drawing Sheets

(56) References Cited

FOREIGN PATENT DOCUMENTS

| WO | WO 2014/184246 | 11/2014 |
|---|---|---|
| WO | WO 2015/034812 | 3/2015 |
| WO | WO 2016/210405 | 12/2016 |

OTHER PUBLICATIONS

Kondo et al. Int. J. Clin. Oncol., 2013, vol. 18, pp. 380-388 (Published Online Feb. 15, 2012) (Year: 2013).*
Cramer et al. British Journal of Nutrition, 2012, vol. 107, pp. 1333-1338 (Year: 2012).*
Boado, R.J., et al., "Gene expression of GLUT3 and GLUT1 glucose transporters in human brain tumors," *Molecular Brain Research*, 1994, vol. 27, pp. 51-57.
Deleyrolle, L.P., et al., "Evidence for label-retaining tumour-initiating cells in human glioblastoma," *Brain*, 2011, vol. 134, pp. 1331-1343.
Fotovati, A., et al., "YB-1 Bridges Neural Stem Cells and Brain Tumor-Initiating Cells via Its Roles in Differentiation and Cell Growth," *Cancer Research*, 2011, vol. 71, No. 16, pp. 5569-5578.
Gao, Y., et al., "Inhibition of Y-box binding protein-1 slows the growth of glioblastoma multiforme and sensitizes to temozolomide independent $O_6$-methylguanine-DNA methyltransferase," *Molecular Cancer Therapeutics*, Dec. 2009, vol. 8, No. 12, pp. 3276-3284.
Kohsaka, S., et al., "STAT3 Inhibition Overcomes Temozolomide Resistance in Glioblastoma by Downregulating MGMT Expression," *Molecular Cancer Therapeutics*, 2012, vol. 11, No. 6, pp. 1289-1299.
Le Calvé, B., et al., "Long-term In Vitro Treatment of Human Glioblastoma Cells with Temozolomide Increases Resistance In Vivo through Up-regulation of GLUT Transporter and Aldo-Keto Reductase Enzyme AKR1C Expression," *Neoplasia*, 2010, vol. 12, No. 9, pp. 727-739.
Redon, C.E., et al., "Tumors induce complex DNA damage in distant proliferative tissues in vivo," *PNAS*, Oct. 19, 2010, vol. 107, No. 42, p. 17992-17997.
Sherry, M.M., et al., "STAT3 is Required for Proliferation and Maintenance of Multipotency in Glioblastoma Stem Cells," *Stem Cells*, 2009, vol. 27, pp. 2383-2392.
Siebzehnrubl, F.A., et al., "The ZEB1 pathway links glioblastoma initiation, invasion and chemoresistance," *EMBO Molecular Medicine*, 2013, vol. 5, pp. 1196-1212.
Written Opinion in International Application No. PCT/US2014/023934, dated Aug. 26, 2014, pp. 1-9.
Farooqi, A. A et al. "Shattering the underpinnings of neoplastic architecture in LNCaP: synergistic potential of nutraceuticals in dampening PDGFR/EGFR signaling and cellular proliferation" *Journal of Experimental Therapeutics and Oncology*, 2011, pp. 201-206, vol. 9, No. 3.
Otto, C. et al. "Growth of human gastric cancer cells in nude mice is delayed by a ketogenic diet supplemented with omega-3 fatty acids and medium-chain triglycerides" *BMC Cancer*, Apr. 30, 2008, pp. 1-12, vol. 8, No. 122.
Baranano, K. W. et al. "The Ketogenic Diet: Uses in Epilepsy and Other Neurologic Illnesses" *Current Treatment Options in Neurology*, Nov. 2008, pp. 410-419, vol. 10, No. 6.
Papi, A. et al. "Cytotoxic and Antioxidant Activity of 4-Methylthio-3-butenyl Isothiocyanate from *Raphanus sativus* L (Kaiware Daikon) Sprouts" *Journal of Agricultural and Food Chemistry*, 2008, pp. 875-883, vol. 56, No. 3.
Li, Y. et al. "Implications of cancer stem cell theory for cancer chemoprevention by natural dietary compounds" *Journal of Nutritional Biochemistry*, 2011, pp. 799-806, vol. 22.
Office Action for U.S. Appl. No. 14/197,897, dated Oct. 20, 2016, pp. 1-16.
Basnet, P. et al. "Curcumin: An Anti-Inflammatory Molecule from a Curry Spice on the Path to Cancer Treatment" *Molecules*, 2011, pp. 4567-4598, vol. 16.

Navarro-Peran, E. et al. "The anti-inflammatory and anti-cancer properties of epigallocatechin-3-gallate are mediated by folate cycle disruption, adenosine release and NF-κB suppression" *Inflammation Research*, 2008, pp. 472-478, vol. 57.
Cheung, K. L. et al. "Synergistic Effect of Combination of Phenethyl Isothiocyanate and Sulforaphane or Curcumin and Sulforaphane in the Inhibition of Inflammation" *Pharmaceutical Research*, Jan. 2009, pp. 224-231, vol. 26, No. 1.
"Low-Carbohydrate, High-Protein Diets May Reduce Both Tumor Growth Rates and Cancer Risk" *Science Daily*, Jun. 14, 2011, pp. 1-3, obtained from internet on Apr. 20, 2012: http://www.sciencedaily.com/releases/2011/06/110614115037.htm.
Chan, A. "Low-Carb, High-Protein Diet Slows Cancer Growth in Mice, Study Finds" *Huffington Post*, Jun. 14, 2011, pp. 1-2, obtained from internet on Apr. 20, 2012: http://www.huffingtonpost.com/2011/06/14/low-carb-high-protein-die_n_876645.html.
Dowling, R. J. et al. "Understanding the benefit of metformin use in cancer treatment" *BMC Medicine*, 2011, pp. 1-6, vol. 9, No. 33.
Zhou, W. et al. "The calorically restricted ketogenic diet, an effective alternative therapy for malignant brain cancer" *Nutrition & Metabolism*, 2007, pp. 1-15, vol. 4, No. 5.
Klement, R. J. et al. "Is there a role for carbohydrate restriction in the treatment and prevention of cancer?" *Nutrition & Metabolism*, 2011, pp. 1-16, vol. 8, No. 75.
Ho, V. W. et al. "A Low Carbohydrate, High Protein Diet Slows Tumor Growth and Prevents Cancer Initiation" *Cancer Research*, Jul. 1, 2011, pp. 4484-4493, vol. 71.
Universitatsklinikum Wurzburg, "Information on a ketogenic (low carbohydrate / high fat + protein) diet for cancer patients", 2009, pp. 1-31, obtained from http://www.frauenklinik.uni-wuerzburg.de/forschung/ketogenic english.htm.
Tisdale, M. J. et al. "Reduction of weight loss and tumour size in a cachexia model by a high fat diet" *Br. J. Cancer*, 1987, pp. 39-43, vol. 56.
Stan, S. D. et al. "Bioactive Food Components and Cancer Risk Reduction" *Journal of Cellular Biochemistry*, 2008, pp. 339-356, vol. 104.
Kozluca, O. et al. "Prevention of doxorubicin induced cardiotoxicity by catechin" *Cancer Letters*, 1996, pp. 1-6, vol. 99.
Lee, W.-L. et al. "Phytoagents for Cancer Management: Regulation of Nucleic Acid Oxidation, ROS, and Related Mechanisms" *Oxidative Medicine and Cellular Longevity*, 2013, pp. 1-22, vol. 2013, Article ID 925804.
Gaona-Gaona, L. et al. "Protective effect of sulforaphane pretreatment against cisplatin-induced liver and mitochondrial oxidant damage in rats" *Toxicology*, 2011, pp. 20-27, vol. 286.
Seyfried, T. N. et al. "Targeting energy metabolism in brain cancer: review and hypothesis" *Nutrition & Metabolism*, 2005, pp. 1-9, vol. 2, No. 30.
Waseem, M. et al. "Mitochondrial dysfunction mediated cisplatin induced toxicity: Modulatory role of curcumin" *Food and Chemical Toxicology*, 2013, pp. 334-342, vol. 53.
Nebeling, L. C. et al. "Effects of a ketogenic diet on tumor metabolism and nutritional status in pediatric oncology patients: two case reports" *J. Am Coll Nutr*, Apr. 1995, pp. 202-208, vol. 14, No. 2.
Du, G.-J. et al. "Epigallocatechin Gallate (EGCG) is the Most Effective Cancer Chemopreventive Polyphenol in Green Tea" *Nutrients*, 2012, pp. 1679-1691, vol. 4.
Lao, C. D. et al. "Dose escalation of a curcuminoid formulation" *BMC Complementary and Alternative Medicine*, Mar. 17, 2006, pp. 1-4, vol. 6, No. 10.
Nebeling, L. C. et al. "Implementing a ketogenic diet based on medium-chain triglyceride oil in pediatric patients with cancer" *Journal of the American Dietetic Association*, Jun. 1995, pp. 693-697, vol. 95, No. 6.
Shapiro, T. A .et al. "Chemoprotective Glucosinolates and Isothiocyanates of Broccoli Sprouts: Metabolism and Excretion in Humans" *Cancer Epidemiology, Biomarkers & Prevention*, May 2001, pp. 501-508, vol. 10.
Bachstetter, A. D. et al. "Spirulina Promotes Stem Cell Genesis and Protects against LPS Induced Declines in Neural Stem Cell Proliferation" *PLoS One*, May 2010, pp. 1-11, vol. 5, Issue 5, e10496.

(56) References Cited

OTHER PUBLICATIONS

Kelsey, N. A. et al. "Nutraceutical Antioxidants as Novel Neuroprotective Agents" *Molecules*, Nov. 3, 2010, pp. 7792-7814, vol. 15.

Maalouf, M. et al. "The neuroprotective properties of calorie restriction, the ketogenic diet, and ketone bodies" *Brain Research Reviews*, 2009, pp. 293-315, vol. 59.

Martuscello, R. T. et al. "A Supplemental High-Fat Low-Carbohydrate Diet for the Treatment of Glioblastoma" *Clinical Cancer Research*, Dec. 2, 2015, pp. 2482-2495, vol. 22, No. 10.

Seyfried, T. N. et al. "Targeting Energy Metabolism in Brain Cancer with Restricted Diets" *Glioblastoma*, Sep. 18, 2009, pp. 341-363.

Jeong et al. "Modulation of AP-1 by Natural Chemopreventive Compounds in Human Colon HT-29 Cancer Cell Line" Pharmaceutical Research, 2004, vol. 21, No. 4, pp. 649-660.

Fusimi, K. "Can Simian Virus 40 be the factor of human tumor outbreaks?", *Tiss. Cult. Res. Commun.*, 1997, vol. 16, pp. 181-187, summary.

Biao, J. Health Caring with Daikon Radish, Nov. 30, 2010; in Chinese.

Biao, J. Health Caring with Daikon Radish, Nov. 30, 2010; English translation of relevant portion.

Office Action dated Sep. 10, 2018; Chinese Patent Application No. 201480028215.2.

Riken, K. "Discovery of a novel gene allowing brassica vegetables to make cancer-preventing components,—New way to develop health-functional vegetables", Press release graspable in 60 seconds, DNA Research Institute, Apr. 10, 2007; in Japanese.

Riken, K. "Discovery of a novel gene allowing brassica vegetables to make cancer-preventing components,—New way to develop health-functional vegetables", Press release graspable in 60 seconds, DNA Research Institute, Apr. 10, 2007; English translation of relevant portion.

Office Action dated Oct. 23, 2018; Japanese Patent Application No. 2016-501388.

Office Action dated Nov. 13, 2018; U.S. Appl. No. 14/197,897.

Chung, M-Y. et al. "Molecular mechanisms of chemopreventive phytochemicals against gastroenterological cancer development" *World J. Gastroenterol.*, 2013, 19(7):984-993.

Schmitz, K. et al. "'Disease modifying nutricals' for multiple sclerosis" *Pharmacology & Therapeutics*, 2015, 148:85-113.

Office Action dated Jan. 29, 2019; U.S. Appl. No. 15/078,590.

Khalife, S. et al. "Molecular targets of natural health products in arthritis" *Arthritis Research & Therapy*, 2011, vol. 13, p. 102 (3 pages).

Kong, J-S. et al. "Inhibition of Synovial Hyperplasia, Rheumatoid T Cell Activation, and Experimental Arthritis in Mice by Sulforaphane, a Naturally Occurring Isothiocyanate" *Arthritis & Rheumatism*, 2010, pp. 159-170, vol. 62, No. 1.

Illustration, Well-understandable agriculture technology innovation, Agriculture can be industrialized and adaptable to IT (Information Technology) this far., Oct. 27, 2011, first edition, first printing, pp. 68-69 (additionally cited literature, showing well-known technology).

Office Action dated Dec. 17, 2019; Japanese Patent Application No. 2018-093204, pp. 1-6.

Li, Y. and Tollefsbol, T. "Impact on DNA methylation in cancer prevention and therapy by bioactive dietary components" *Curr. Med. Chem.*, 2010, 17(20):2141-2151.

Davidson, R. et al. "Sulforaphane Represses Matrix-Degrading Proteases and Protects Cartilage From Destruction In Vitro and In Vivo" *Arthritis & Rheumatism*, 2013, 65(12):3130-3140.

Davidson, R. et al. "Isothiocyanates are detected in human synovial fluid following broccoli consumption and can affect the tissues of the knee joint" *Scientific Reports*, 2017, 7:3398 (10 pages).

Fahey, J. et al. "Broccoli sprouts: An exceptionally rich source of inducers of enzymes that protect against chemical carcinogens" *Proc. Natl. Acad. Sci. USA*, 1997, 94:10367-10372.

Thysen, S. et al. "Targets, models and challenges in osteoarthritis research" *Disease Models & Mechanisms*, 2015, 8:17-30.

Sporn, M. and Harris, E. "Proliferative diseases" *Am. J. Med.*, 1981, 70(6):1231-1235, abstract.

Vyas, D. et al. "Chemotherapy-enhanced inflammation may lead to the failure of therapy and metastasis" OncoTargets and Therapy, 2014, 7:1015-1023.

Agerbirk, N. et al. "Glucosinolate structures in evolution" *Phytochemistry*, 2012, 77:16-45.

\* cited by examiner

REGULATION OF CANCER USING NATURAL COMPOUNDS AND/OR DIET

CROSS-REFERENCE TO RELATED APPLICATIONS

This application is a divisional of U.S. application Ser. No. 14/775,751, filed Sep. 14, 2015, which is the U.S. national stage application of International Patent Application No. PCT/US2014/023934, filed Mar. 12, 2014, which claims the benefit of U.S. Provisional Application Ser. No. 61/784,386, filed Mar. 14, 2013, the disclosures of which are hereby incorporated by reference in their entirety, including all figures, tables and amino acid or nucleic acid sequences.

Due to a shift in most cancer cells from oxidative phosphorylation to aerobic glycolysis (known as the Warburg effect) cancer can be viewed as a metabolic disease where energy flux is shifted from a highly efficient method of generating energy (36 molecules of ATP from 1 molecule of glucose) to an inefficient method (4 molecules of ATP from one molecule of glucose). The result is that cancer cells expend an enormous amount of glucose to survive and multiply. While controversy exists as to the relationship between the Warburg effect and altered signaling pathways, the combined reliance of tumor cells for excessive amounts of glucose and signaling pathway alterations suggest that targeting these two related phenomena may provide better outcomes in cancer treatment.

Most cancer treatments employ the use of toxic chemicals aimed at killing cancerous cells. While these treatments are highly effective, unfortunately, they have similar effects on normal, non-cancerous cells as well. The key to developing an effective and well-tolerated chemotherapy regime is to balance the positive tumor killing effects of the compounds with the toxic side effects. The use of non-toxic compounds that are able to target altered signaling pathways and influence energy flux may provide an effective and tolerable treatment. An additional advantage of using non-toxic approach is the ability to apply multiple agents simultaneously with reduced chances of cumulative toxicity. The current invention provides treatment of proliferative disorders that target altered signaling pathways and energy flux in cancerous cells.

BRIEF SUMMARY OF THE INVENTION

The current invention provides a treatment of a proliferative disease comprising, administering to a subject in need of a treatment against a proliferative disease, a composition comprising one or more natural products (compounds) and, optionally, simultaneously providing to the subject a low carbohydrate diet. In certain embodiments of the invention, the subject consumes (or is provided) a modified ketogenic diet (mKD) or a ketogenic diet (KD). Thus, the current invention also provides a therapy for a subject in need of a treatment against a proliferative disorder, the therapy comprising administering to a subject consuming a mKD or KD diet a composition comprising one or more natural compounds (component(s)) selected from, epigallocatechin-3-gallate (EGCG), curcumin, compositions comprising glucosinolates and/or derivatives thereof, such as glucoraphanin and/or sulforaphane (SFN) (as found in broccoli sprouts or sprouts of other cruciferous vegetables), and, optionally, Daikon radish sprout, a Daikon radish sprout extract or a powder of said extract or the Daikon radish sprout. In another aspect of the invention, the method of treating a proliferative disorder comprises administering one or more component(s) selected from, epigallocatechin-3-gallate (EGCG), curcumin, compositions comprising glucosinolates and/or derivatives thereof, such as glucoraphanin and/or SFN (derived from sources such as broccoli sprouts, sprouts of other cruciferous vegetables or cruciferous vegetables themselves) and, optionally, Daikon radish sprout, a Daikon radish sprout extract or a powder of said extract or the Daikon radish sprout, and, optionally, simultaneously providing a low carbohydrate, mKD or KD diet.

Another aspect of the invention provides methods that attenuate/reducing the loss or the proliferative ability of neural stem cells (NSC) or their progeny [collectively called precursor cells] of the CNS in a subject developing a tumor or having a tumor or in a subject having a neurodegenerative disease or disorder, such as Parkinson's disease (PD), Alzheimer's disease (AD), stroke, Amyotrophic lateral sclerosis (ALS), Acute disseminated encephalomyelitis (ADEM) and Neuromyelitis optica (NMO) or that which is associated to aging or age-related cognitive decline. Thus, various embodiments of this aspect of the invention provide methods of attenuating/reducing the loss in activity of precursor cells or a loss in the number of precursor cells in the CNS in a subject developing a tumor or having a tumor or in a subject having a neurodegenerative disease or disorder or a age related reduction in CNS function, comprising administering to a subject a composition comprising one or more natural compounds (component(s)) selected from, epigallocatechin-3-gallate (EGCG), curcumin, compositions comprising glucosinolates and/or derivatives thereof, such as glucoraphanin and/or sulforaphane (SFN) (such as broccoli sprouts, sprouts of other cruciferous vegetables or cruciferous vegetables themselves), and, optionally, Daikon radish sprout, a Dailon radish sprout extract or a powder of said extract or the Daikon radish sprout and, optionally, simultaneously providing a low carbohydrate, mKD or KD diet.

The current invention also provides a composition comprising one or more of the following natural compounds (components): EGCG, curcumin, compositions comprising glucosinolates and/or derivatives thereof, such as SFN and/or glucoraphanin (optionally in the form of broccoli sprouts, the sprouts of other cruciferous vegetables or cruciferous vegetables themselves), and Daikon radish sprout, a Dailon radish sprout extract or a powder of said extract or the Daikon radish sprout and, optionally, medium chain triglycerides (MCT).

BRIEF DESCRIPTION OF DRAWINGS

FIG. 10A) Patient derived hGB cells were serially passed in culture for 5 passages under a variety of treatment conditions. Cells were treated with EGCG (8 µM), curcumin (0.5 µM, SFN (2.5 µM) or their combination (NP). NP had the greatest growth inhibitory effect. *, *p<0.05, p<0.001 compared to control, ###p<0.001 compared to NP, Linear regression. FIG. 10B) The rate of tumor propagating cell aka cancer stem cell (CSC) expansion (Kll) is directly correlated to the probability CSCs undergo self-renewing symmetric division and can be calculated by taking the natural logarithm of the fold expansion and dividing by the passage time (Deleyrolle et al., 2011). Human GB cells were cultured in the neurosphere assay over 5 passages during which CSC expansion rate was evaluated. Only SFN or NP treated groups demonstrated significant decrease of CSCs self-renewing symmetric division rate compared to control. Also NP exhibited the greatest effect suggesting a unique synergistic effect. *, p<0.001 compared to control, ####, p<0.001 compared to NP, 1-way ANOVA.

FIG. 33A) mKD/NP protects neural stem cells from dysregulation related to tumor development. It has been demonstrated that the presence of a tumor can create a chronic inflammatory response sufficient to induce damage and cellular dysregulation in tissues distant from the tumor site (Redon et al., 2010). We demonstrated that development of a tumor mass following subcutaneous implant of hGB cells in the right flank of NOD/SCID animals downregulated neural stem cell activity (based on BrdU incorporation) in area related to cognition (e.g. hippocampus). Animals treated with mKD/NP did not demonstrate any decrease in NSC activity compared to the non-tumor bearing group. These results demonstrate a protective effect of mKD/NP on NSC activity. FIG. 33B) hNSC were plated at 20K cells per 100 ul of medium and cultured in the neurosphere assay for 14 days. Starting 2 days post plating, the cells were daily treated with EGCG (8 µM), Curcumin (0.5 µM), sulforaphane (SFN, 2.5 µM) or a combination of all three NP. After 14 days in culture, MTT assay was performed to measure cell viability. Only the combination of the 3 natural products (NP) exhibited a significant effect compared to control. Cells treated with NP displayed a 70% increase in cell viability compared to controls or each individual component. ***, p<0.0001, compared to NP, 1-way ANOVA. These data demonstrate that NP treatment increases survival of NSCs.

enhances the effect of mKD/NP. NOD/SCID animals were inoculated with 1M hGB cells in the right flank. Tumor progression was monitored by measuring tumor volume 3 times per week using a caliper. Treatments were initiated when a palpable mass was identified [approximately 65 mm$^3$]. Animals treated with mKD/NP containing DRSP demonstrated a significant slower tumor progression compared to controls or animals treated with mKD/NP not containing DRSP (*, ***, p<0.05, p<0.001, Two-way ANOVA).

Treatments:

Control: 55% carbohydrate, 30% protein, 15% fat.

mKD/NP.001=10% carbohydrate, 60% Fat (half coming from MCT, Neobee 598), 30% Protein+Natural Products (NP) containing SFN (25 mg/kg; BSP100%), Curcumin (1200 mg/kg), EGCG (1200 mg/kg).

mKD/NP.002=10% carbohydrate, 60% Fat (half coming from MCT, Neobee 598), 30% Protein+Natural Products (NP) containing SFN (25 mg/kg; BSP95%/DRSP5%), Curcumin (1200 mg/kg), EGCG (1200 mg/kg).

Figure 35:
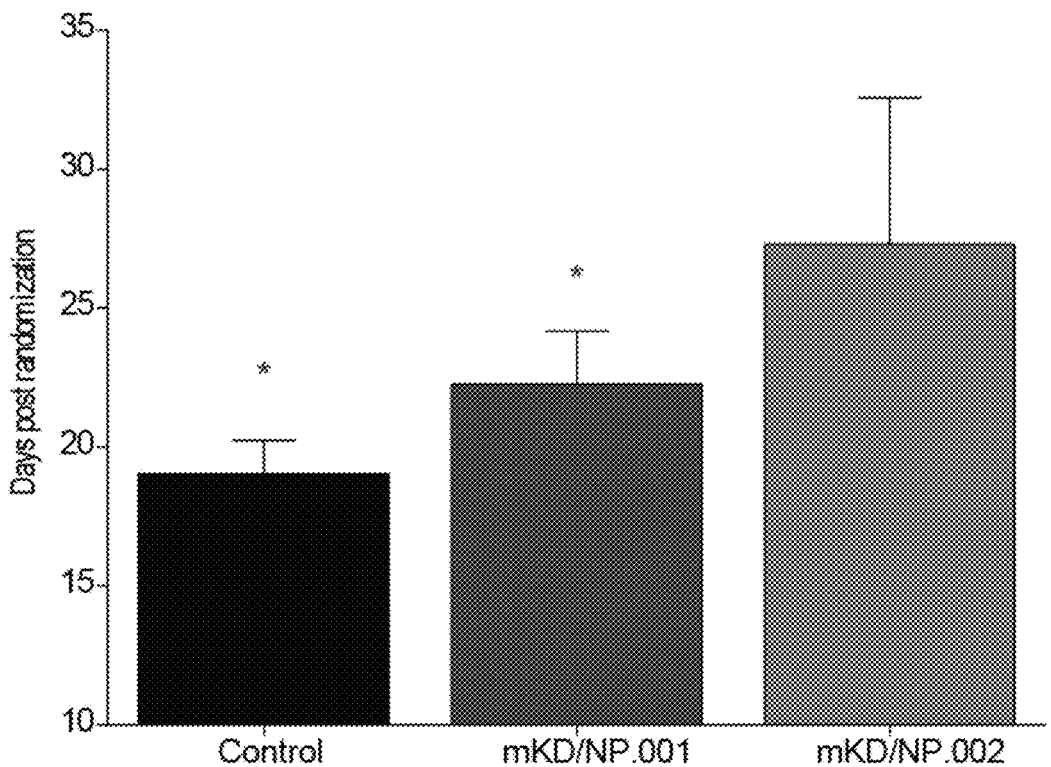

FIG. 35: Optimization mKD/NP—Progression free survival. NOD/SCID animals were inoculated with 1M hGB cells in the right flank. Tumor volume was calculated 3 times per week and the time from a barely palpable tumor [approximately 65 mm$^3$] to a tumor of a significant size [300 mm$^3$] was calculated. Treatments were initiated when a palpable mass was identified [approximately 65 mm$^3$]. Animals treated with mKD/NP.002 (containing DRSP) demonstrated a significant increase of tumor progression free survival time (time during which tumor volume is maintained lower than 300 mm) compared to controls or animals treated with mKD/NP.001 (not containing DRSP). *, p<0.05, F-test, compared to mKD/NP.002.

Figure 36:
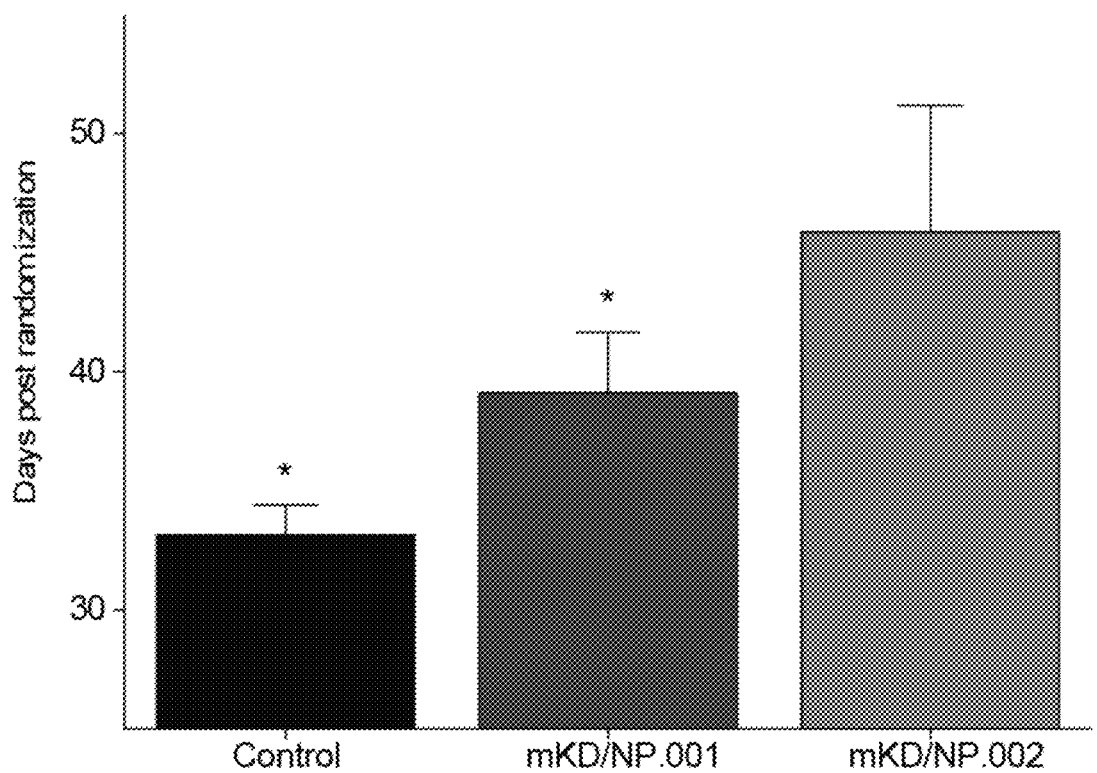

FIG. 36: Optimization mKD/NP—overall survival. NOD/SCID animals were inoculated with 1M hGB cells in the right flank. Tumor volume was monitored 3 times per week. Treatments were initiated when a palpable mass was identified [approximately 65 mm$^3$]. Animals were sacrificed when they reached endpoint (1500 mm$^3$). The average time to reach endpoint volume (i.e. overall survival time) was then compared. Animals treated with mKD/NP.002 (containing DRSP) demonstrated a significant increase of mean survival compared to controls or animals treated with mKD/NP.001 (not containing DRSP). *, p<0.05, F-test, compared to mKD/NP.002.

Figure 37A:
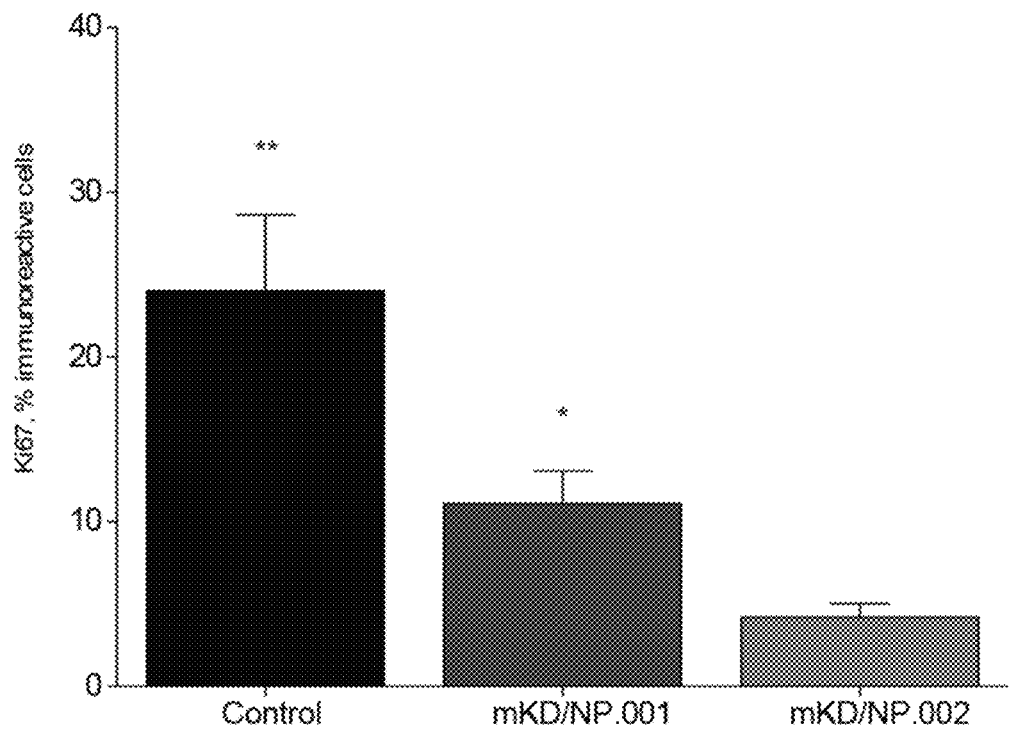
Figure 37B:
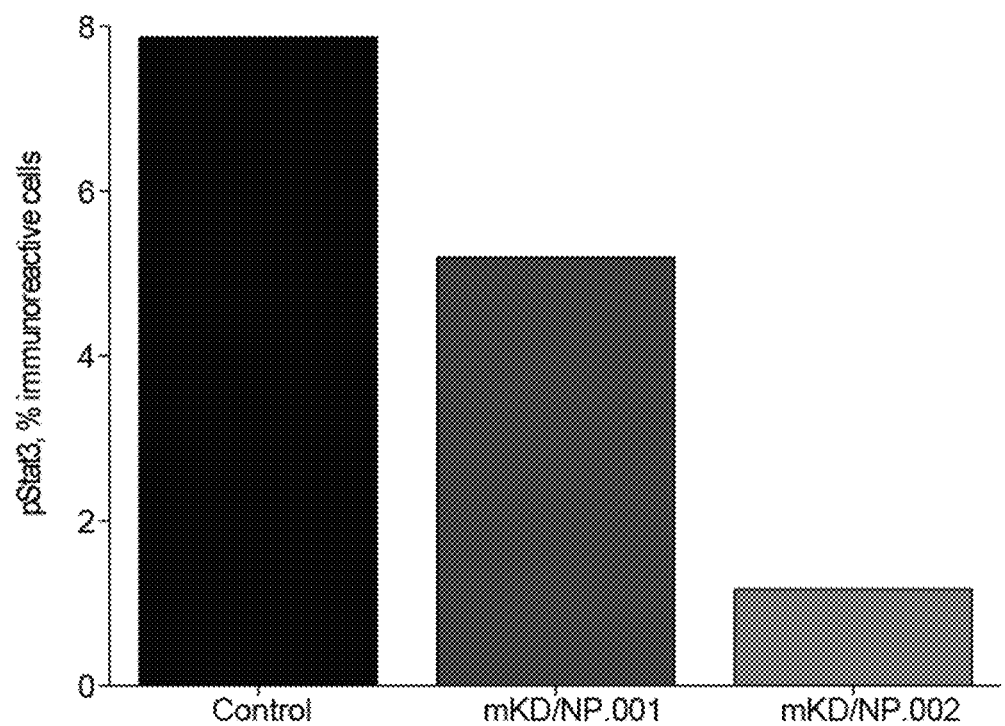

FIGS. 37A-37B: Optimization mKD/NP—Ki67 and pStat3. NOD/SCID animals were inoculated with 1M hGB cells in the right flank. Tumor volume was monitored 3 times per week. Treatments were initiated when a palpable mass was identified [approximately 65 mm$^3$]. Animals were sacrificed when they reached endpoint (1500 mm$^3$) and the tumors were harvested and prepared to quantify tumor cell proliferation using Ki67 and pStat3 labeling. (FIG. 37A) The percentage of immunoreactive cells was quantified using flow cytometry. Animals treated with mKD/NP.002 (containing DRSP) demonstrated a significant decrease of proliferation compared to controls or animals treated with mKD/NP.001 (not containing DRSP). *, **, p<0.05, p<0.001, t-test, compared to mKD/NP.002. (FIG. 37B) Stat3 activation (via phosphorylation) is required for proliferation of cancer cells in general and in Glioblastoma (Sherry et al., 2009). Targeting Stat3 is thus a potential target for cancer therapy. mKD/NP is able to inhibit the phosphorylation of Stat3 compared to controls. This effect is potentiated with mKD/NP.002 when DRSP is included in the treatment as noted above.

Figure 38:
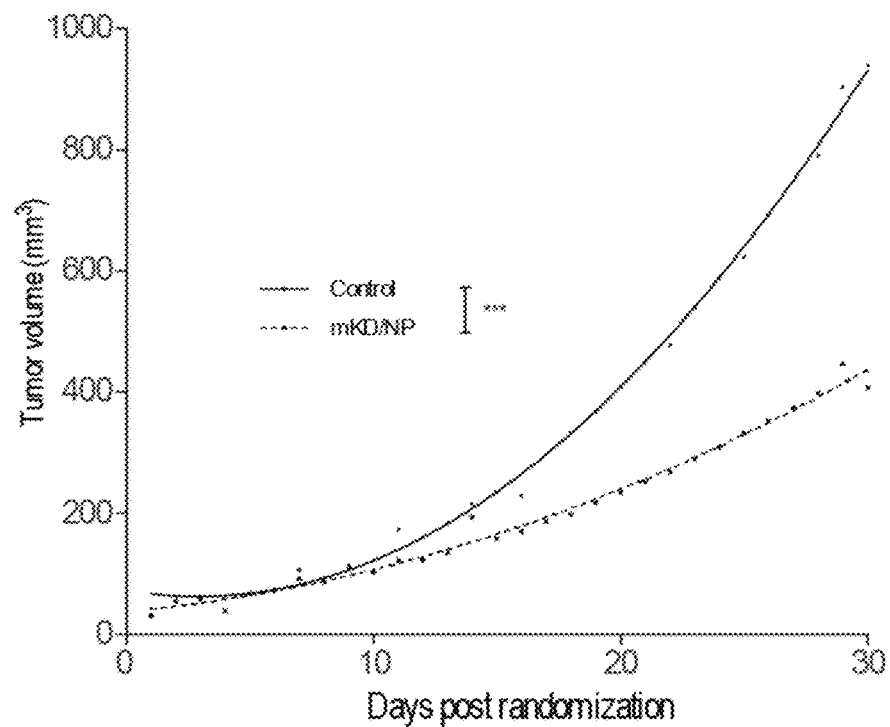

FIG. 38: Effect of mKD/NP on colon cancer—tumor progression. NOD/SCID animals were inoculated with 2M of colorectal adenocarcinoma cells (HT-29) in the right flank. Tumor progression was monitored by measuring tumor volume 3 times per week using a caliper. Treatments were initiated when a palpable mass was identified [approximately 65 mm$^3$]. Animals were sacrificed when they reached endpoint (1000 mm$^3$). Animals treated with mKD/NP demonstrated a significant slower tumor progression compared to controls (***, p<0.0001, two-way ANOVA).

Figure 39:
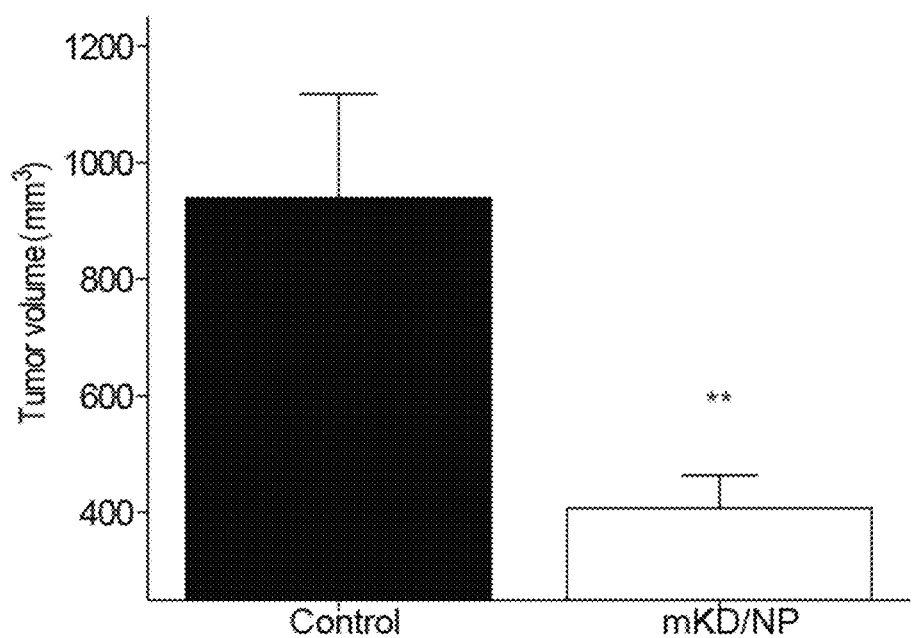

FIG. 39: Effect of mKD/NP on colon cancer—tumor volume. NOD/SCID animals were inoculated with 2M of colorectal adenocarcinoma cells (HT-29) in the right flank. Tumor progression was monitored by measuring tumor volume 3 times per week using a caliper. Treatments were initiated when a palpable mass was identified [approximately 65 mm$^3$]. Tumor volume was compared 30 days post treatment initiation. On average, animals treated with mKD/NP demonstrated a significant lower tumor volume compared to controls (**p<0.01, t-test).

Figure 40:
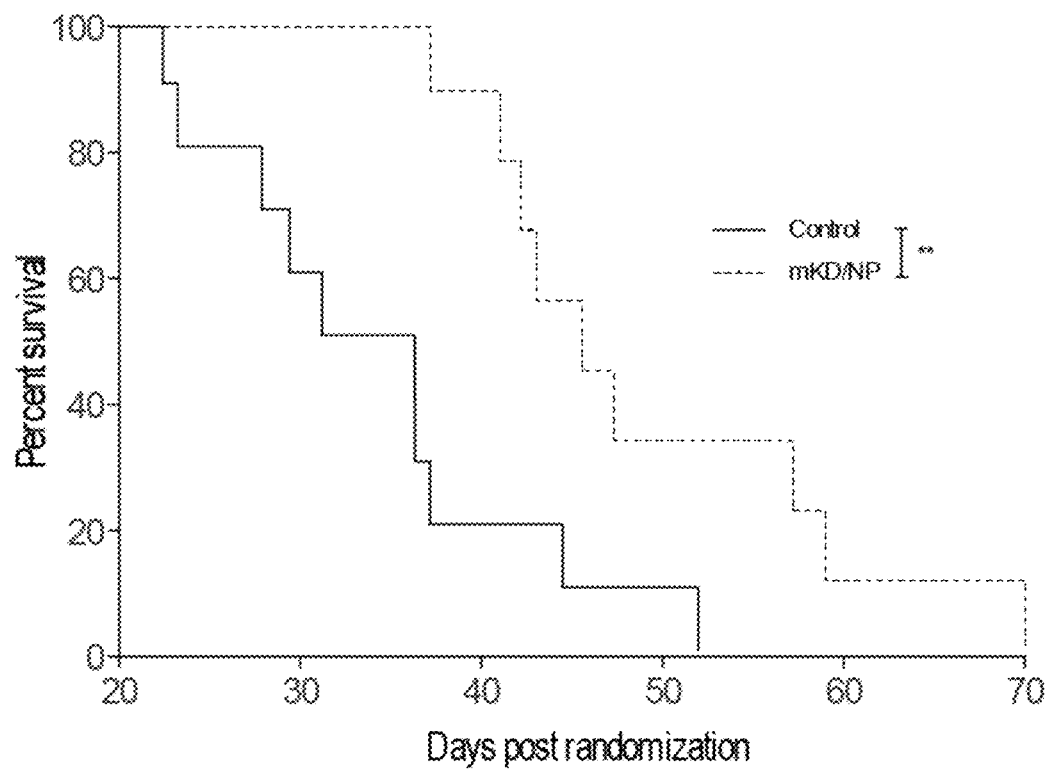

FIG. 40: Effect of mKD/NP on colon cancer—KM curve. NOD/SCID animals were inoculated with 2M of colorectal adenocarcinoma cells (HT-29) in the right flank. Tumor progression was monitored by measuring tumor volume 3 times per week using a caliper. Treatments were initiated when a palpable mass was identified [approximately 65 mm$^3$]. Animals were sacrificed when they reached endpoint (1000 mm$^3$). The fraction of animals living as a function of time is represented using Kaplan-Meier survival curves. Animals treated with mKD/NP demonstrated a significant improvement over controls (**p<0.01, Log rank test).

Figure 41:
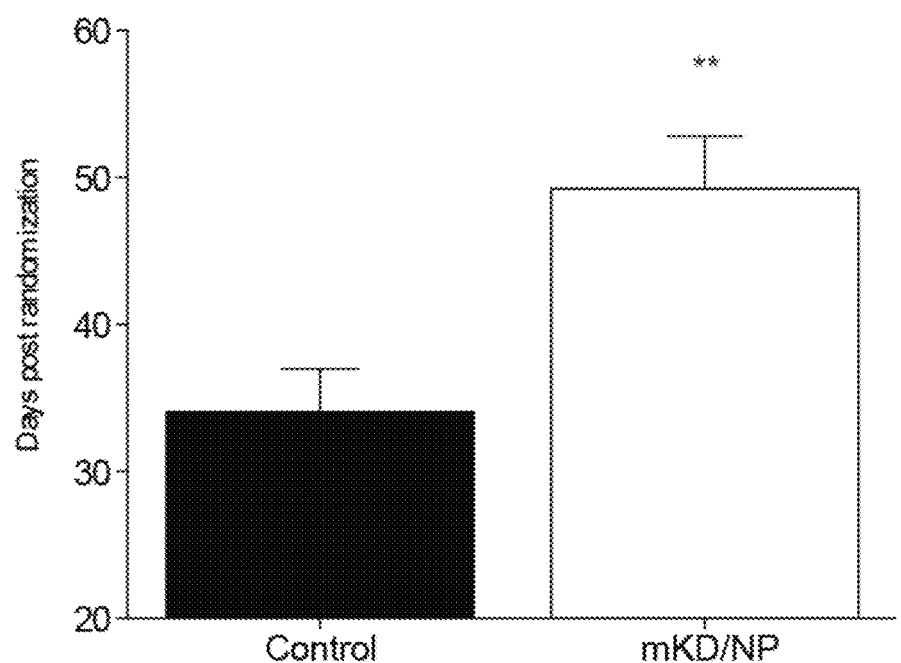

FIG. 41: Effect of mKD/NP on colon cancer—overall survival. NOD/SCID animals were inoculated with 2M of colorectal adenocarcinoma cells (HT-29) in the right flank. Tumor progression was monitored by measuring tumor volume 3 times per week using a caliper. Treatments were initiated when a palpable mass was identified [approximately 65 mm$^3$]. Animals were sacrificed when they reached endpoint (1000 mm$^3$). The average time to reach endpoint volume (i.e. overall survival time) was then compared. Animals treated with mKD/NP demonstrated a significant increase of overall survival compared to controls (**, p<0.01, t-test). These data demonstrate that mKD/NP is an effective treatment for colon cancer.

Figure 42:
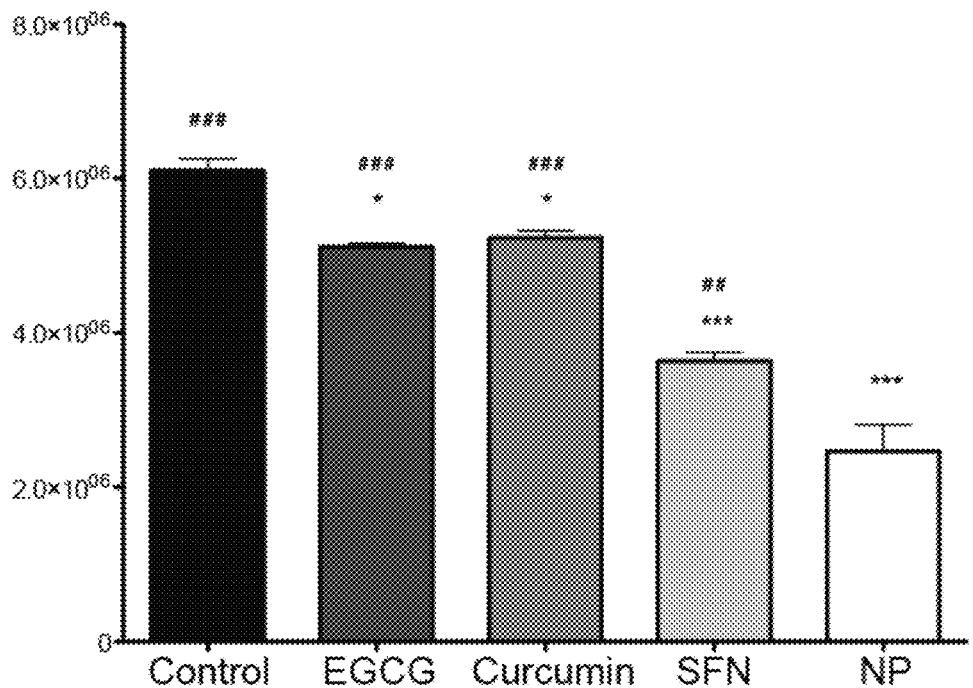

FIG. 42: Effect of NP on colon cancer cells (in vitro). Colorectal adenocarcinoma cells (HT-29) were treated daily with EGCG (8 μM), Curcumin (0.5 μM) and sulforaphane (2.5 μM). Once the control cultures became confluent, a cell count was performed. All individual compounds exhibited a significant reduction in cell number. The combination of the three natural products together (NP) demonstrated the strongest effect. *, ***, p<0.05, p<0.001, compared to control, ##, ####, p<0.01, p<0.001, compared to NP, 1-way ANOVA.

Figure 43:
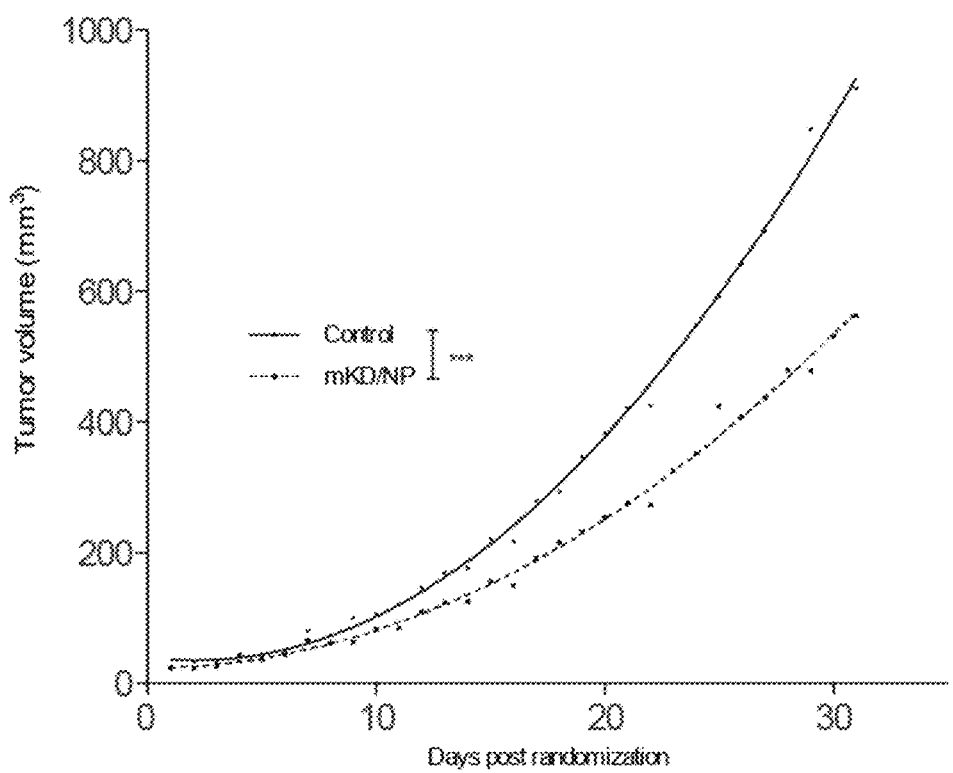

FIG. 43: Effect of mKD/NP on lung cancer—tumor progression. NOD/SCID animals were inoculated with 2M of lung carcinoma cells (A549) in the right flank. Tumor progression was monitored by measuring tumor volume 3 times per week using a caliper. Treatments were initiated when a palpable mass was identified [approximately 65 mm$^3$]. Animals were sacrificed when they reached endpoint (1000 mm$^3$). Animals treated with mKD/NP demonstrated a significant slower tumor progression compared to controls (***p<0.0001, two-way ANOVA).

Figure 44:
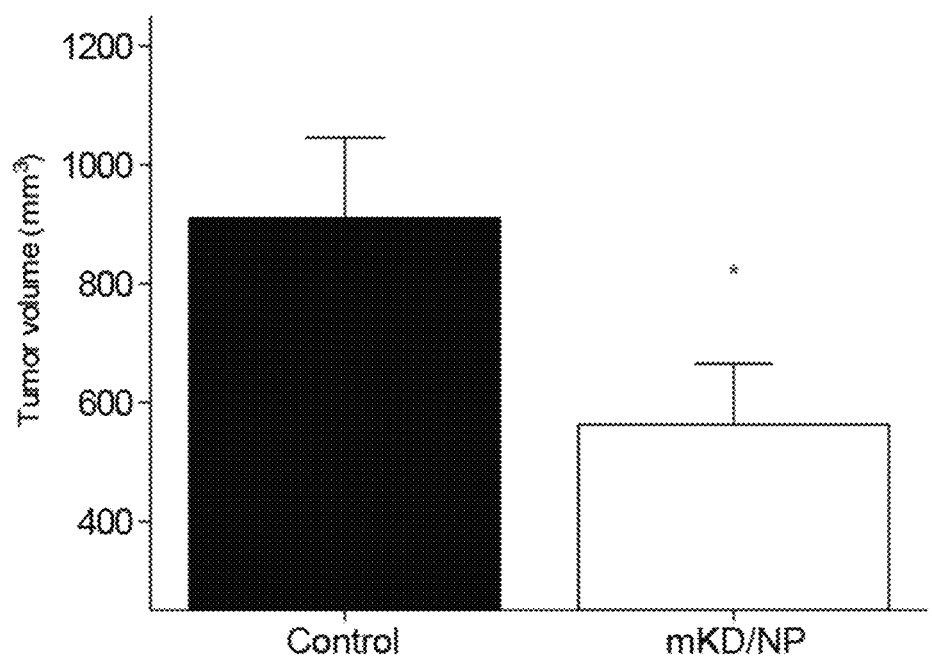

FIG. 44: Effect of mKD/NP on lung cancer—tumor volume. NOD/SCID animals were inoculated with 2M of lung carcinoma cells (A549) in the right flank. Tumor volume was measured 3 times per week and treatments were initiated when a palpable mass was identified [approximately 65 mm$^3$]. Tumor volume was compared 31 days post treatment initiation. Animals treated with mKD/NP demonstrated a significant lower tumor volume compared to controls (*, p<0.05, t-test).

Figure 45:
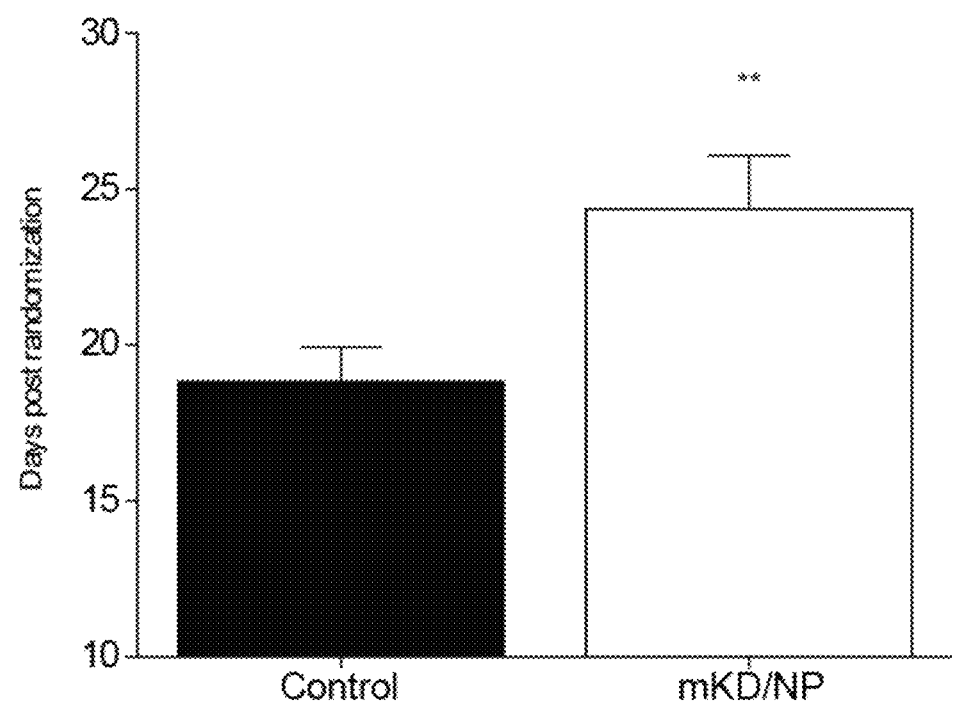

FIG. 45: Effect of mKD/NP on lung cancer—tumor progression free survival. NOD/SCID animals were inoculated with 2M of lung carcinoma cells (A549) in the right flank. Tumor volume was calculated 3 times per week and the time from a barely palpable tumor [approximately 65 mm$^3$] to a tumor of a significant size [300 mm$^3$] was calculated. Treatments were initiated when a palpable mass was identified [approximately 65 mm$^3$]. Animals treated with mKD/NP demonstrated a significant increased progression free survival time (time during which tumor volume is maintained lower than 300 mm$^3$) compared to controls (**, p<0.01, t-test).

Figure 46:
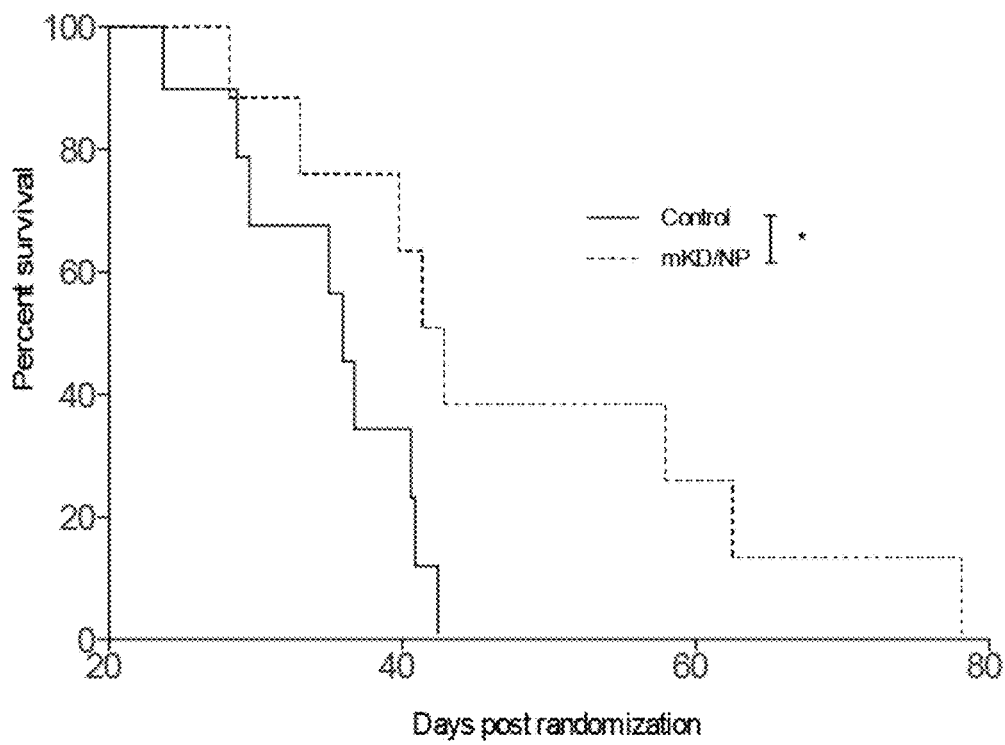

FIG. 46: Effect of mKD/NP on lung cancer—KM curve. NOD/SCID animals were inoculated with 2M of lung carcinoma cells (A549) in the right flank. Tumor progression was monitored by measuring tumor volume 3 times per week using a caliper. Treatments were initiated when a palpable mass was identified [approximately 65 mm$^3$]. Animals were sacrificed when they reached endpoint (1000 mm$^3$). The fraction of animals living as a function of time is represented using Kaplan-Meier survival curves. Animals treated with mKD/NP demonstrated a significant improvement over controls (*, p<0.05, Log rank test).

Figure 47:
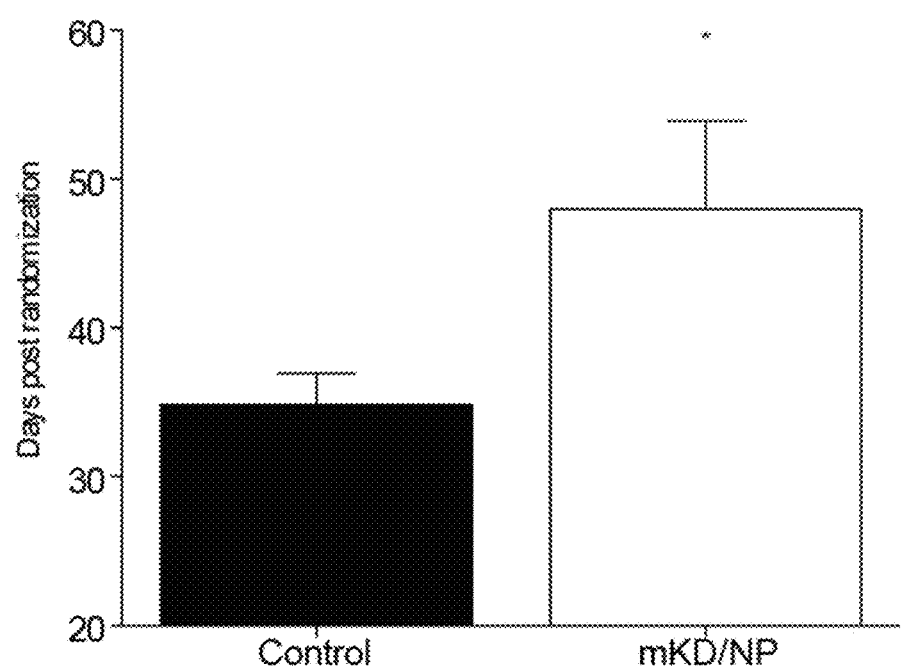

FIG. 47: Effect of mKD/NP on lung cancer—overall survival. NOD/SCID animals were inoculated with 2M of lung carcinoma cells (A549) in the right flank. Tumor volume was monitored 3 times per week using a caliper. Treatments were initiated when a palpable mass was identified [approximately 65 mm$^3$]. Animals were sacrificed when they reached endpoint (1000 mm$^3$). The average time to reach endpoint volume (i.e. overall survival time) was then compared. Animals treated with mKD/NP demonstrated a significant increased overall survival compared to controls (*p<0.05, t-test). These data demonstrate that mKD/NP is an effective treatment for lung cancer.

Figure 48:
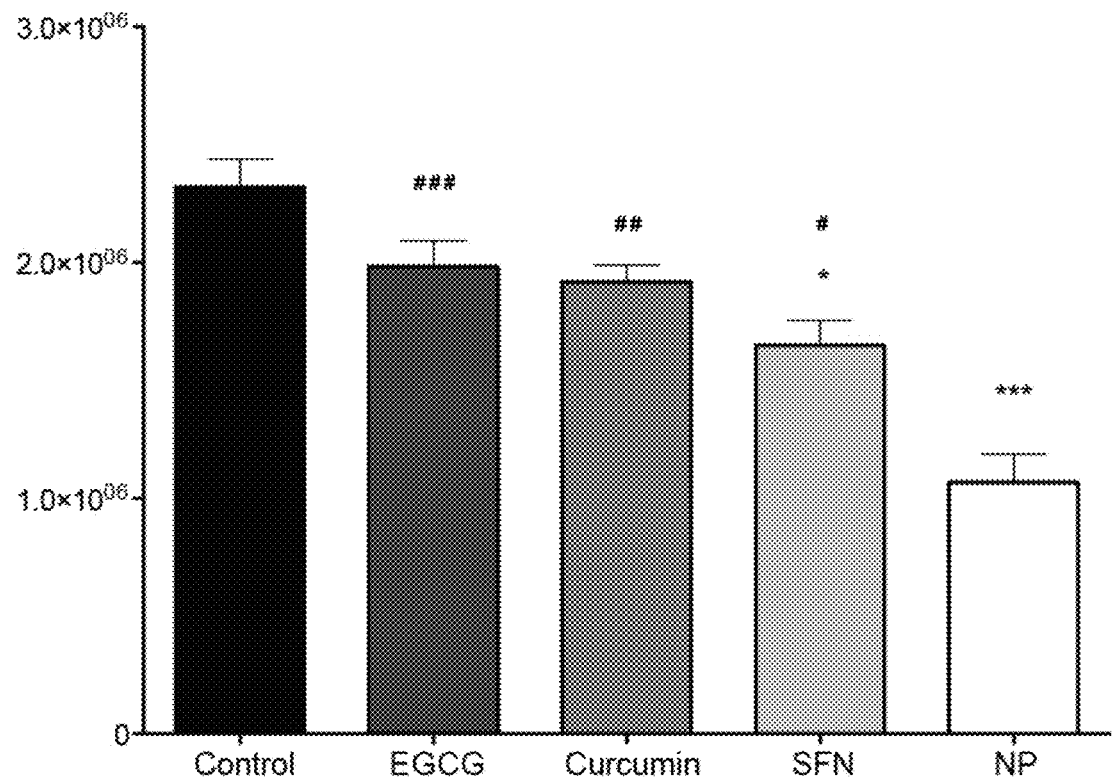

FIG. 48: Effect of NP on lung cancer cells (In vitro). Lung carcinoma cells (A549) were treated daily with EGCG (8 μM), Curcumin (0.5 μM) and sulforaphane (2.5 μM). Once the control cultures became confluent a cell count was performed. Individually EGCG and Curcumin do not show a statistically significant effect in reducing cell numbers while SFN does. This effect is potentiated when all three compounds (NP) are used together. *, ***, p<0.5, p<0.001, compared t control, #, ##, ###, p<0.05, p<0.01, p<0.001, compared to NP, 1-way ANOVA.

Figure 49:
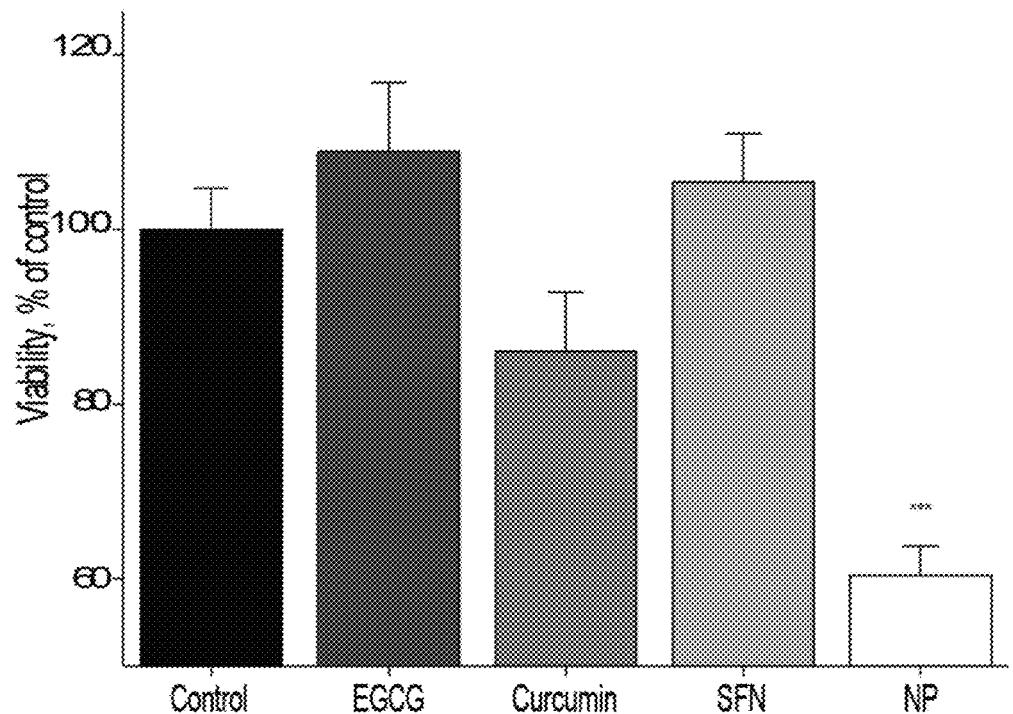

FIG. 49: Effect of NP on breast cancer cell viability. Human breast cancer cells (ZR751) were treated daily with EGCG (8 μM), Curcumin (0.5 μM) or SFN (2.5 μM) individually or in combination (NP). Once the control cultures became confluent, cell viability was measured using MTT assay. Individually, none of the natural product showed statistically significant effect compared to controls while their combination (NP) did. ***, p<0.001, compared to control, 1-way ANOVA.

Figure 50:
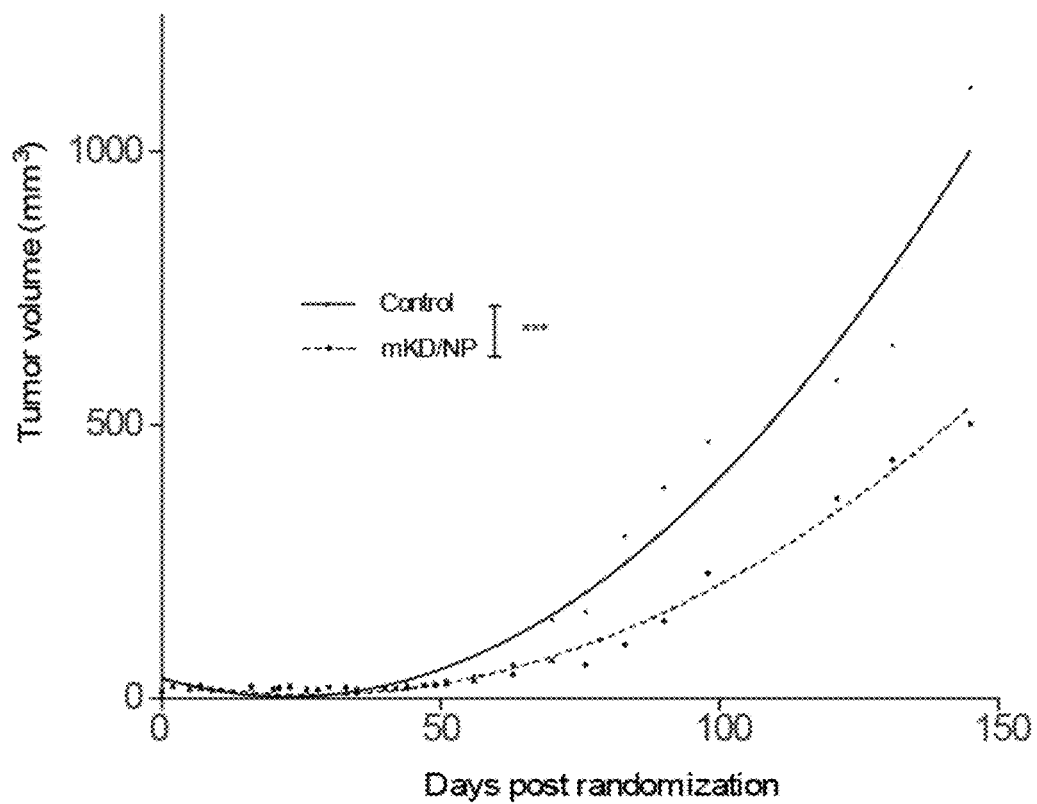

FIG. 50: Effect of mKD/NP on breast cancer—tumor progression. NOD/SCID animals were inoculated with 2M of Breast cancer cells (ZR751) in the right flank. Tumor progression was monitored by measuring tumor volume 3 times per week using a caliper. Treatments were initiated when a palpable mass was identified [approximately 65 mm$^3$]. Animals were sacrificed when they reached endpoint (1000 mm$^3$). Animals treated with mKD/NP demonstrated a significant slower tumor progression compared to controls (***p<0.0001, two-way ANOVA).

Figure 51:
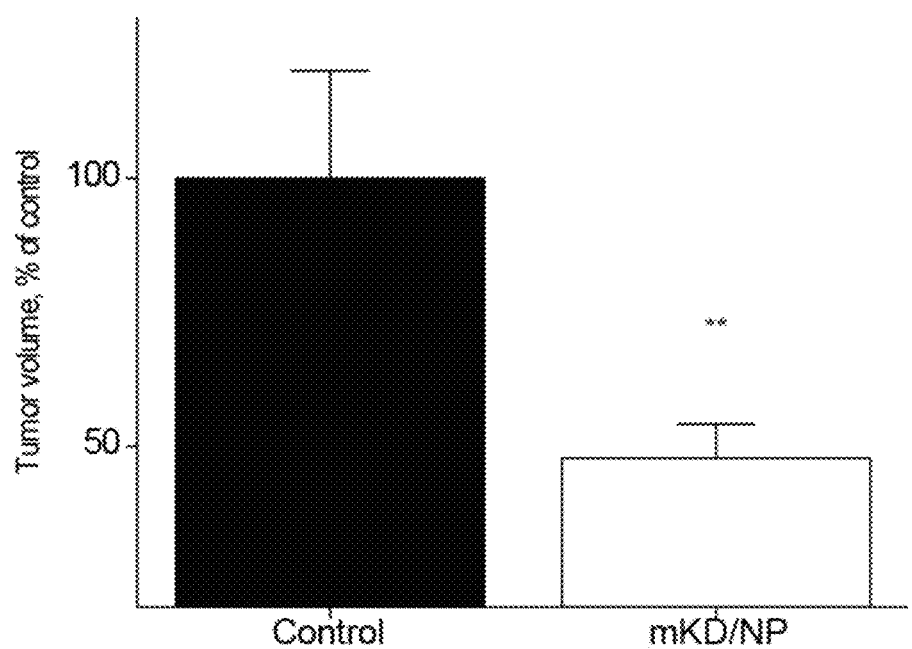

FIG. 51: Effect of mKD/NP on breast cancer—tumor volume (day 70). NOD/SCID animals were inoculated with 2M of Breast cells (ZR751) in the right flank. Tumor volume was monitored 3 times per week using a caliper. Treatments were initiated when a palpable mass was identified [approximately 65 mm$^3$]. Tumor volume was compared 70 days post treatment initiation. Animals treated with mKD/NP demonstrated a significant lower tumor volume compared to controls (**, p<0.01, t-test).

Figure 52:
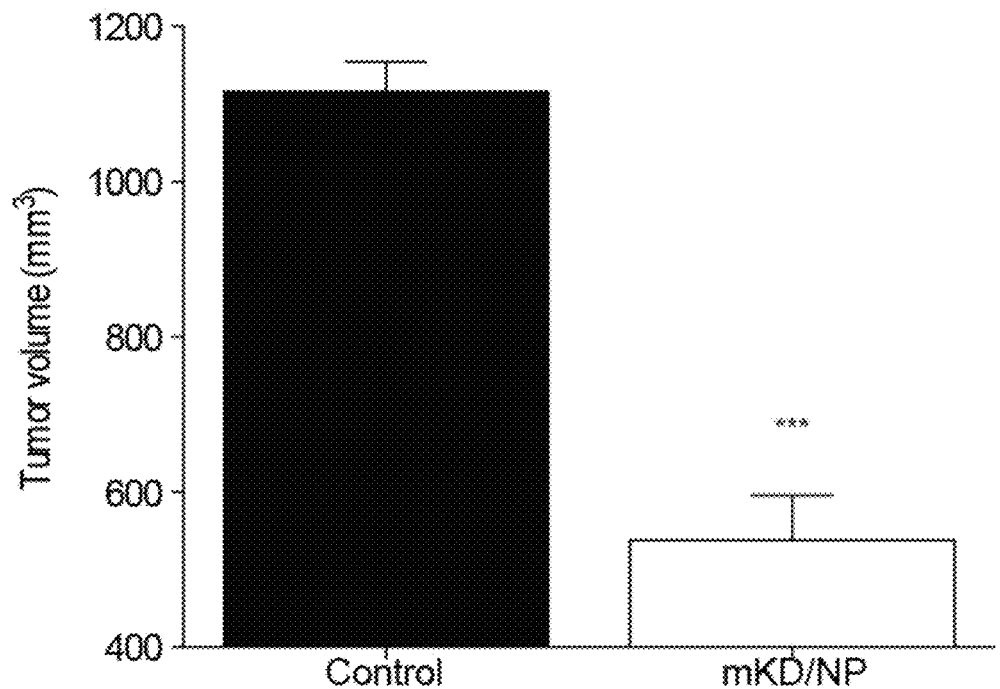

FIG. 52: Effect of mKD/NP on breast cancer—tumor volume (day 145). NOD/SCID animals were inoculated with 2M of Breast cells (ZR751) in the right flank. Tumor volume was monitored 3 times per week using a caliper. Treatments were initiated when a palpable mass was identified [approximately 65 mm$^3$]. Tumor volume was compared 145 days post treatment initiation. Animals treated with mKD/NP demonstrated a significant lower tumor volume compared to controls (**, p<0.01, t-test).

Figure 53:
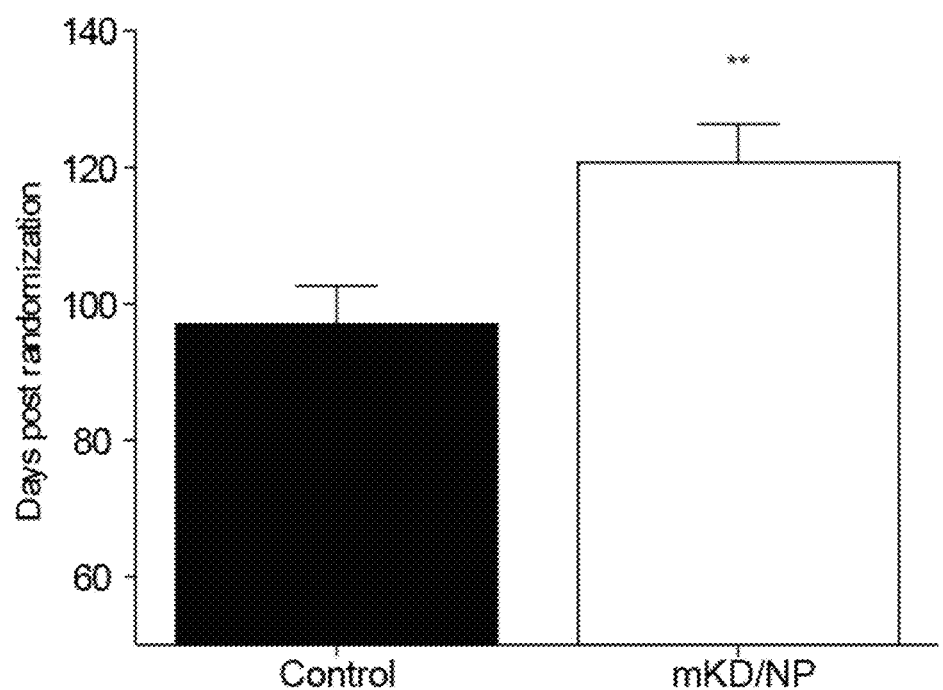

FIG. 53: Effect of mKD/NP on breast cancer—progression free survival. NOD/SCID animals were inoculated with 2M of Breast cells (ZR751) in the right flank. Tumor volume was calculated 3 times per week and the time from a barely palpable tumor [approximately 65 mm$^3$] to a tumor of a significant size [300 mm$^3$] was calculated. Treatments were initiated at palpation [volume approximating 65 mm$^3$] time. Animals treated with mKD/NP demonstrated a significant increased progression free survival time (time during which tumor volume is maintained lower than 300 mm$^3$) compared to controls (**, p<0.01, t-test).

Figure 54:
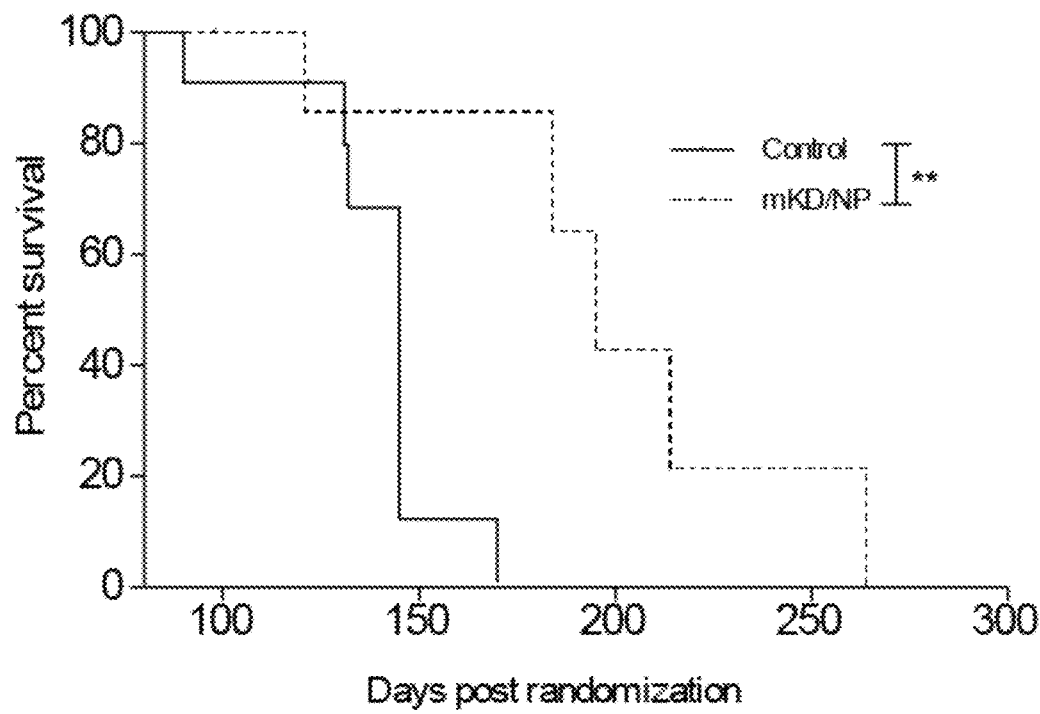

FIG. 54: Effect of mKD/NP on breast cancer—KM curve. NOD/SCID animals were inoculated with 2M of Breast cells (ZR751) in the right flank. Tumor volume was monitored 3 times per week using a caliper. Treatments were initiated when a palpable mass was identified [approximately 65 mm$^3$]. Animals were sacrificed when they reached endpoint (1000 mm$^3$). The fraction of animals living as a function of time is represented using Kaplan-Meier survival curves. Animals treated with mKD/NP demonstrated a significant improvement over controls (**, p<0.01, Log rank test). These data demonstrate that mKD/NP is an effective treatment for breast cancer.

Figure 55:
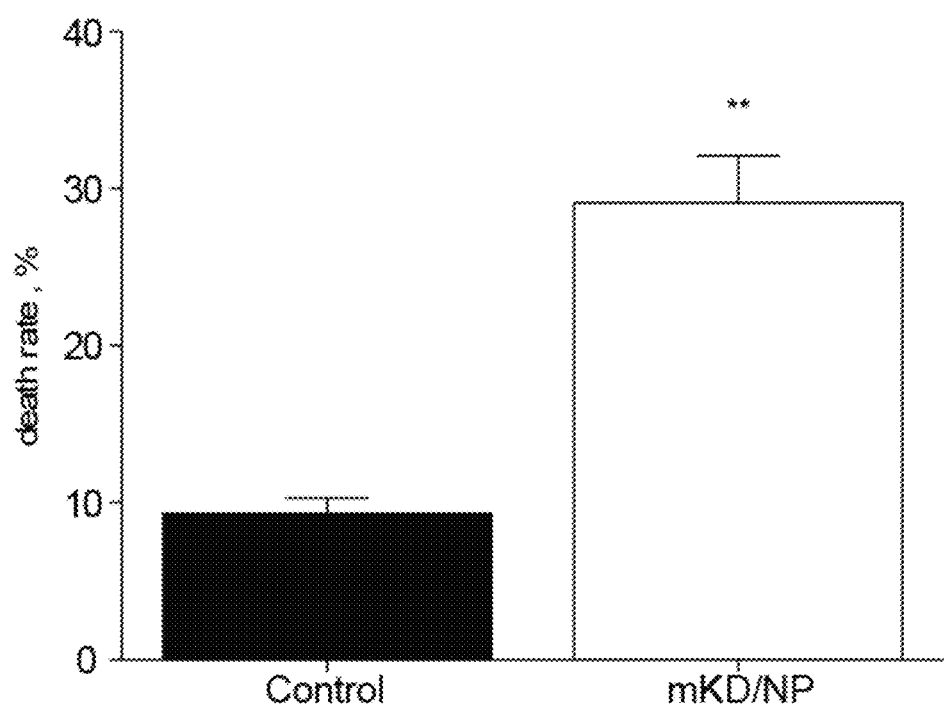

FIG. 55: Effect of mKD/NP on apoptosis of hGB cells (in vivo). NOD/SCID animals were inoculated with 1M hGB cells in the right flank. Tumor volume was monitored 3 times per week using a caliper. Treatments were initiated when a palpable mass was identified [approximately 65 mm$^3$]. Animals were sacrificed when they reached endpoint (1500 mm$^3$) and the tumors were harvested and prepared to quantify tumor cell death using DAPI labeling to identify the SubG1 area indicative of the apoptotic fraction. The percentage of apoptotic cells was quantified using flow cytometry. Animals treated with mKD/NP demonstrated a significant increase in cell death compared to controls (**, p<0.001 t-test). These data indicate that in vivo mKD/NP increases death of hGB cells.

Figure 56:
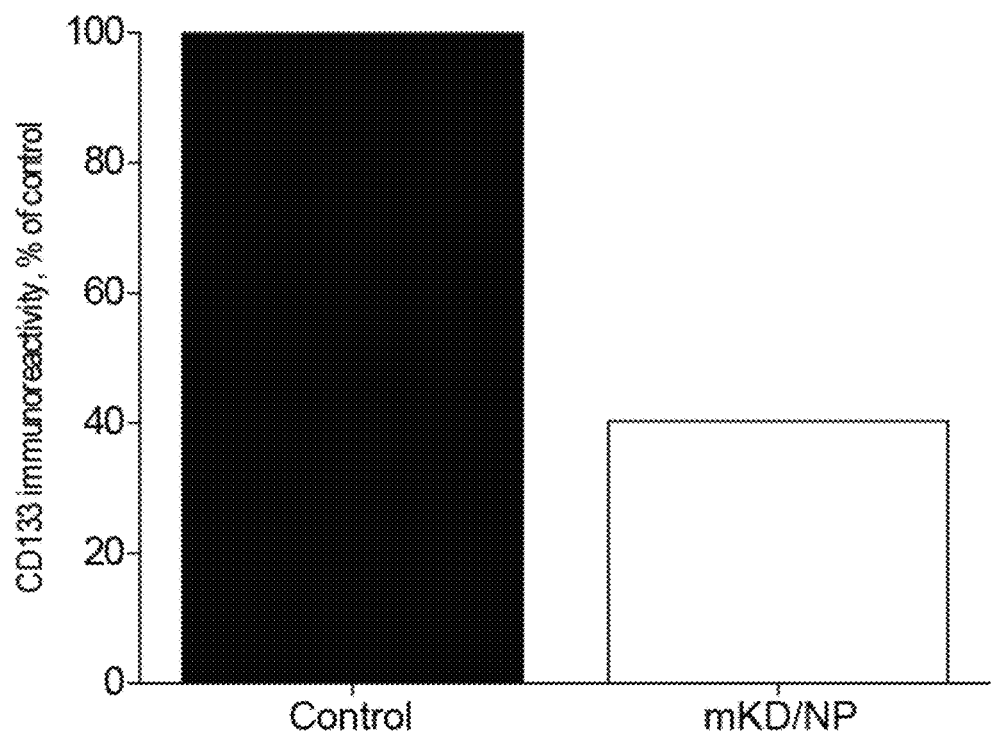

FIG. 56: Effect of mKD/NP on tumor initiating cells (in vivo). NOD/SCID animals were inoculated with 1M hGB cells in the right flank. Tumor volume was monitored 3 times per week using a caliper. Treatments were initiated when a palpable mass was identified [approximately 65 mm$^3$]. Animals were sacrificed when they reached endpoint (1500 mm$^3$) and the tumors were harvested and prepared to quantify tumor cells expressing CD133. CD133 is a marker of tumor initiating cells. The percentage of CD133 immunoreactive cells was quantified using flow cytometry. Sub-Q tumors derived from animals treated with mKD/NP demonstrated a lower amount of CD133+ve cells compared to controls. These data indicate that mKD/NP can target in vivo cancer stem cell (i.e. tumor initiating cells).

Figure 57:
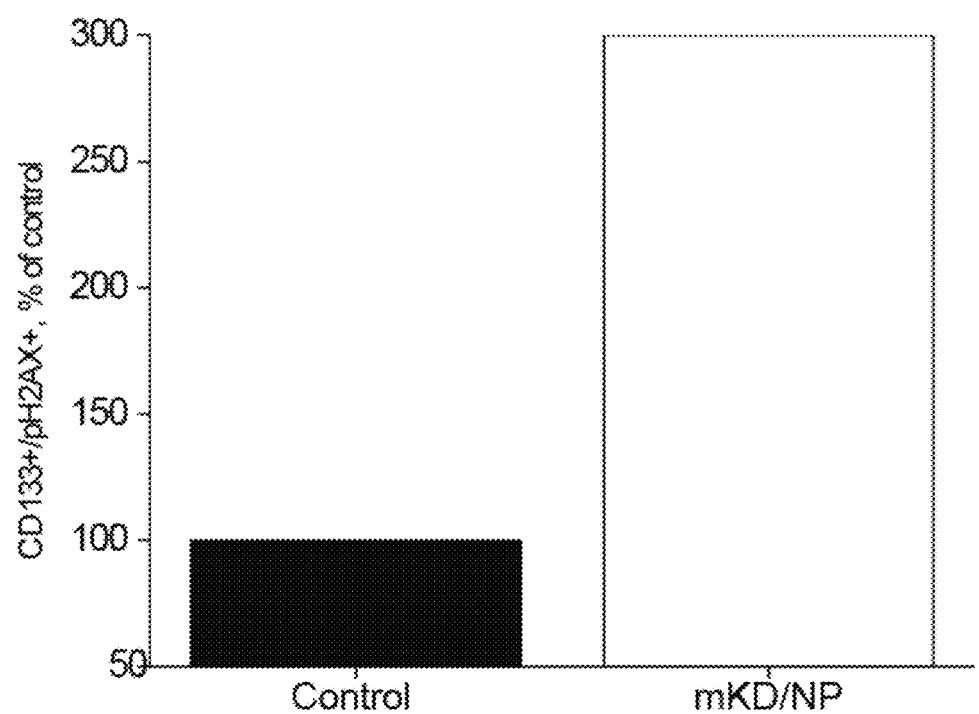

FIG. 57: Effect of mKD/NP on DNA damage in CSC (in vivo). NOD/SCID animals were inoculated with 1M hGB cells in the right flank. Tumor volume was monitored 3 times per week using a caliper. Treatments were initiated when a palpable mass was identified [approximately 65 mm$^3$]. Animals were sacrificed when they reached endpoint (1500 mm$^3$) and the tumors were harvested and prepared to quantify tumor cells colabled with CD133 and the phosphorylated form of H2AX (pH2AX). pH2AX is a marker of DNA double strand breaks. The percentage of CD133/pH2AX double immunoreactive cells was quantified using flow cytometry. Sub-Q tumors derived from animals treated with mKD/NP demonstrated an increase in the number of cancer stem cells (CD133+) exhibiting DNA damages (pH2AX+) compared to controls. These results show that mKD/NP can specifically target in vivo and induce DNA damages in cancer stem cells.

Figure 58A:
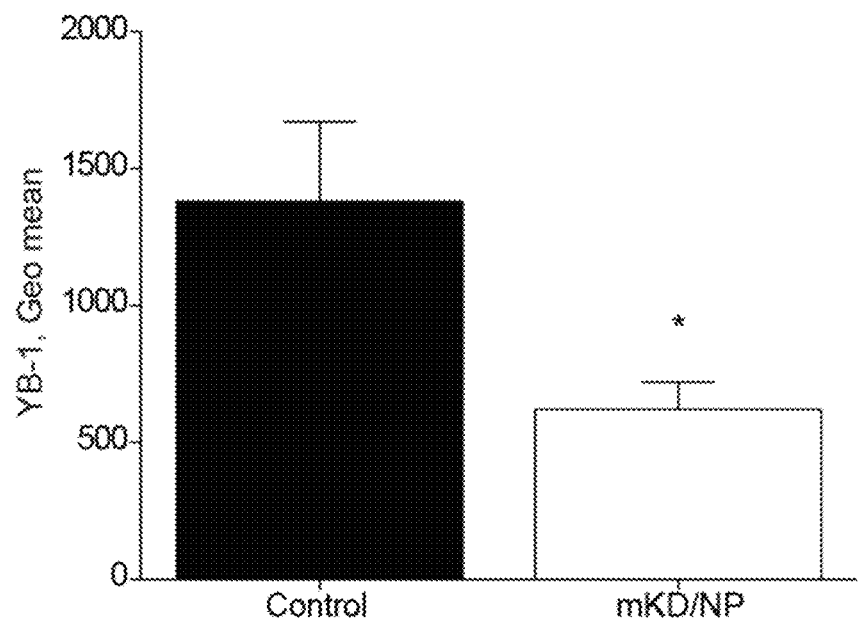
Figure 58B:
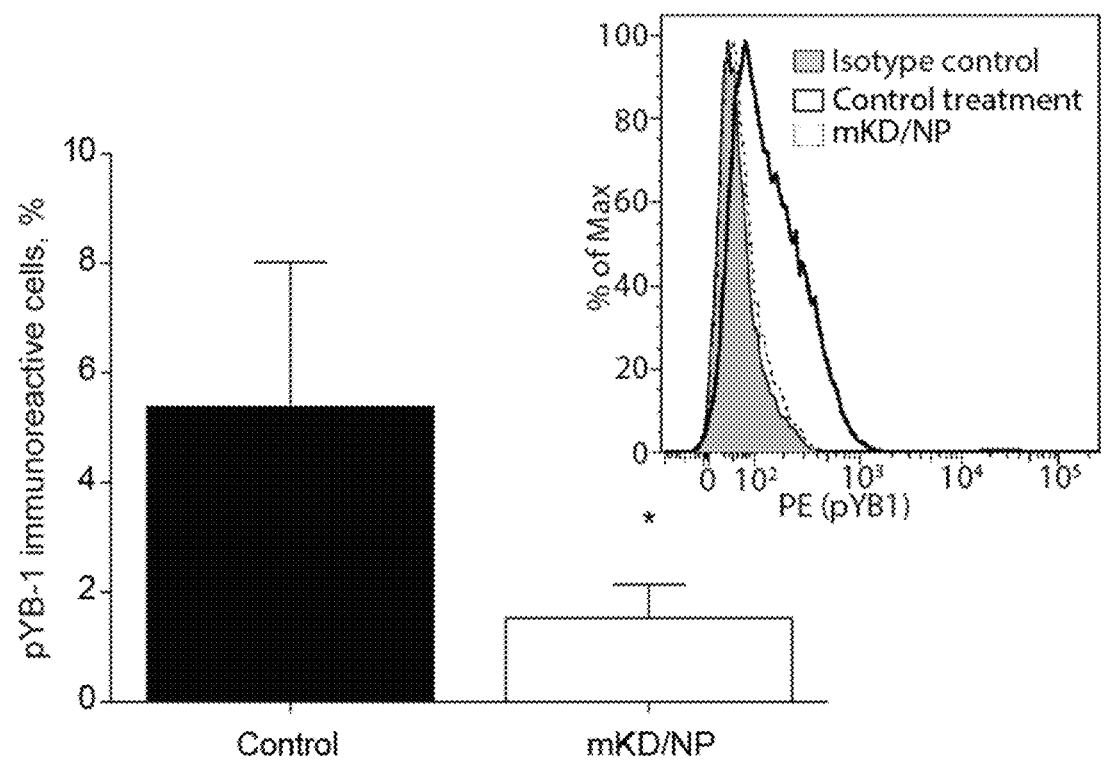

FIGS. 58A-58B: Effect of mKD/NP on YB1 proliferation—MGMT independent sensitization of TMZ resistance (in vivo). NOD/SCID animals were inoculated with 1M hGB cells in the right flank. Tumor volume was monitored 3 times per week using a caliper. Treatments were initiated when a palpable mass was identified [approximately 65 mm$^3$]. Animals were sacrificed when they reached endpoint (1500 mm$^3$) and the tumors were harvested and prepared to quantify by flow cytometry the level of expression and phosphorylation of the Y-box binding protein 1 (YB1). YB-1 is upregulated in many human malignancies including hGB and is implicated in the maintenance of CSCs (Fotovati et al., 2011). Not only is YB-1 critical for hGB maintenance and proliferation but it also plays a role in the mechanism (MGMT independent) of resistance to TMZ by repairing the DNA damages caused by the chemotherapy drug (Gao et al., 2009). Hence, targeting YB-1 represents an appealing approach to inhibit hGB proliferation and to sensitize hGB to TMZ.

Compared to controls, tumor derived from animals treated with mKD/NP demonstrated a significant decrease of YB1 level of expression (FIG. 58A) as well as of phosphorylation (FIG. 58B). *p<0.05, F-test. These results demonstrate that mKD/NP can target the YB-1 pathway, proposing a mechanism by which the treatment is inhibiting tumor cell proliferation and is sensitizing the cells to TMZ via a mechanism independent to MGMT.

Figure 59:
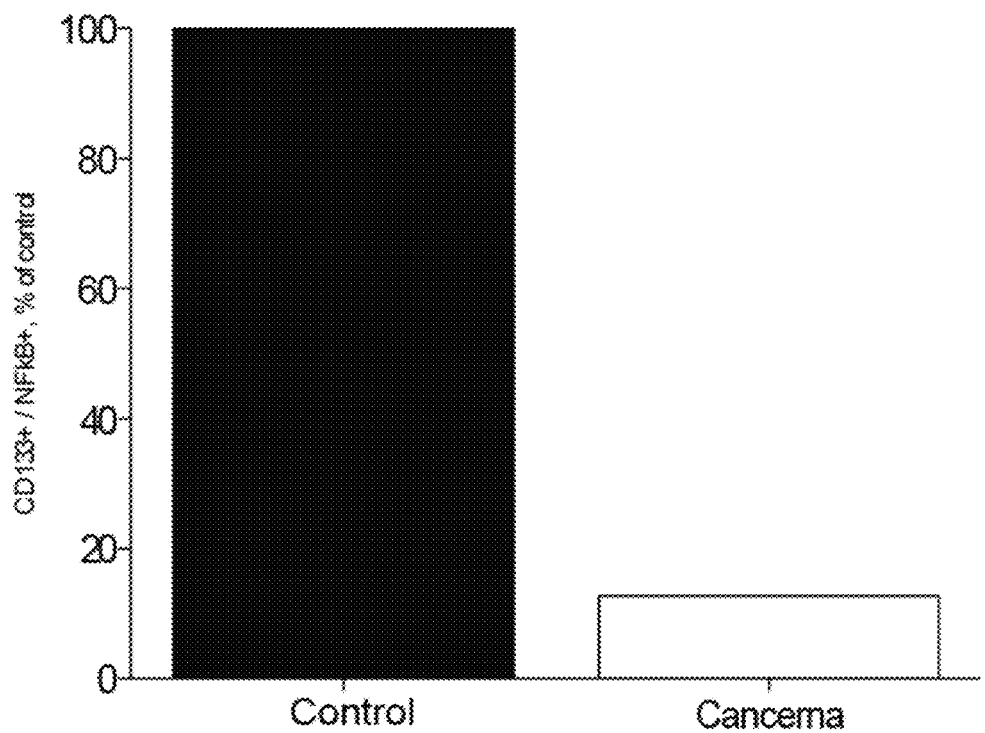

FIG. 59: Effect of mKD/NP on inhibiting chemoresistance in CSC (in vivo). NOD/SCID animals were inoculated with 1M hGB cells in the right flank. Tumor volume was monitored 3 times per week using a caliper. Treatments were initiated when a palpable mass was identified [approximately 65 mm$^3$]. Animals were sacrificed when they reached endpoint (1500 mm$^3$) and the tumors were harvested and prepared to quantify tumor cells co-labeled with CD133 and NFkB. NFkB is an anti-apoptotic effector that also contribute to chemoresistance in hGB (Han et. al., 2004). A) The percentage of CD133/NFkB double immunoreactive cells was quantified using flow cytometry. Tumor derived from animals treated with mKD/NP demonstrated a decrease in the number of cancer stem cells (CD133+) positive for NFkB compared to controls. These results suggest that mKD/NP can target CSCs by inhibiting the anti-apoptotic effector NFkB.

Figure 60:
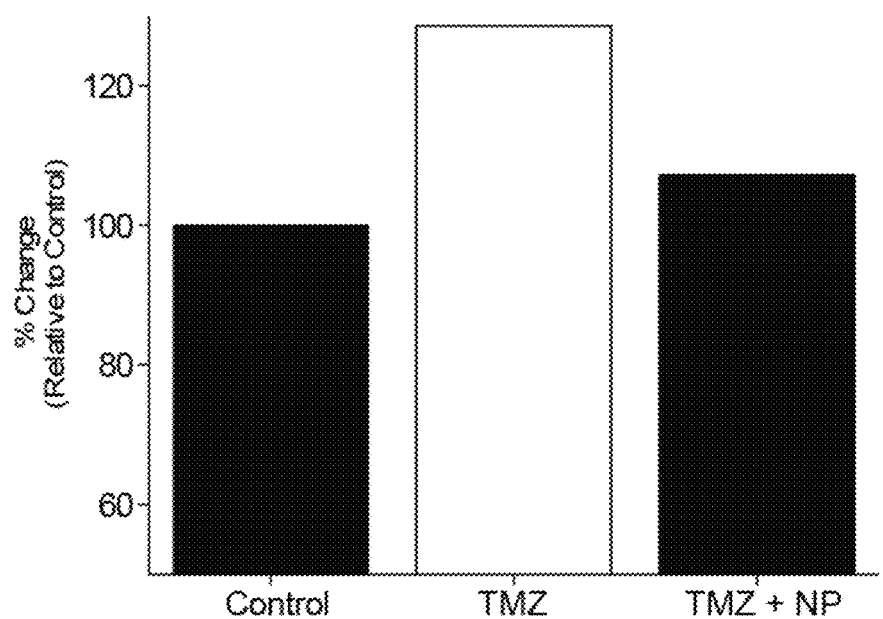

FIG. 60: Effect of mKD/NP on MGMT expression (in vitro). Patient derived GB cells were treated in vitro with TMZ [10 µM] or TMZ [10 µM] & NP (EGCG (8 µM), Curcumin (0.5 µM) and sulforaphane (2.5 µM)). After seven days of treatment cells were harvested and analyzed for expression level of MGMT using flow cytometry. The median fluorescence in the two treated groups were compared relative to the untreated controls. The data indicates that TMZ induces nearly a 30% increase in MGMT expression and that NP is able to attenuate this increase to near control levels.

Figure 61A:
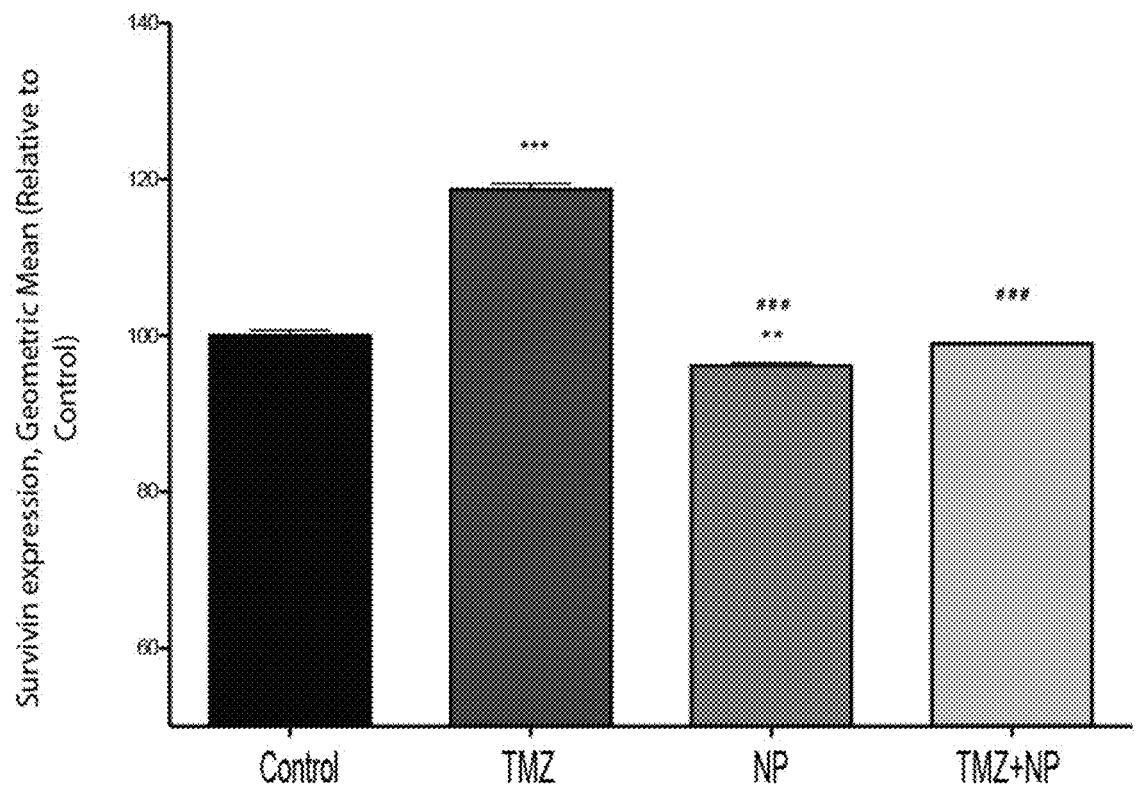
Figure 61B:
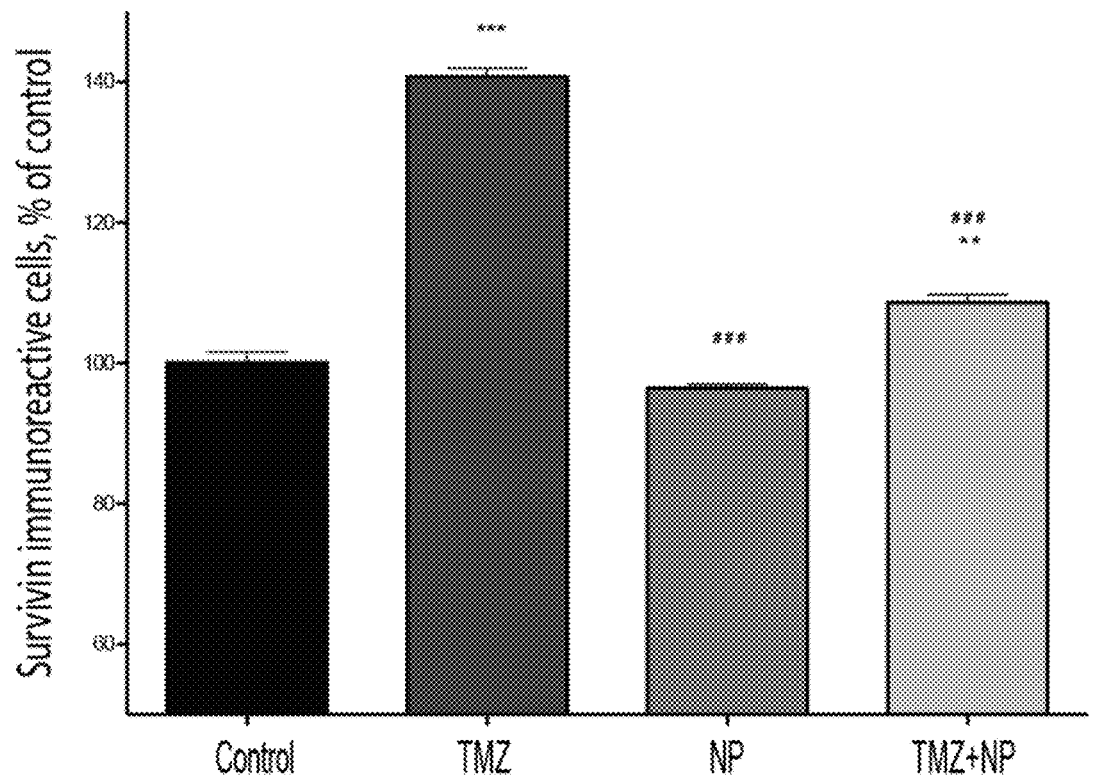

FIGS. 61A-61B: Effect of mKD/NP on surviving expression (in vitro). FIG. 61A) hGB cells were cultured in the neurosphere assay. After 7 days in vitro, the cells were processed for immunolabeling and flow cytometry analysis to access Survivin (a member of the inhibitor of apoptosis for which the overexpression is associated with chemoresistance) level. Expression level of Survivin is increased with TMZ treatment (10 µM, daily treatment for 7 days). This effect is reduced to control levels when TMZ treated cells are also exposed to NP [EGCG (8 µM), Curcumin (0.5 µM) and sulforaphane (2.5 µM), daily treatment for 4-7 days]. FIG. 61B) Similarly, NP reduces the fraction of cells expressing Survivin that is increased when cell are treated with TMZ. , *, compared to control; ####, compared to TMZ. 1-way ANOVA, 2 symbols p<0.01, 3 symbols p<0.0001.

Figure 29:
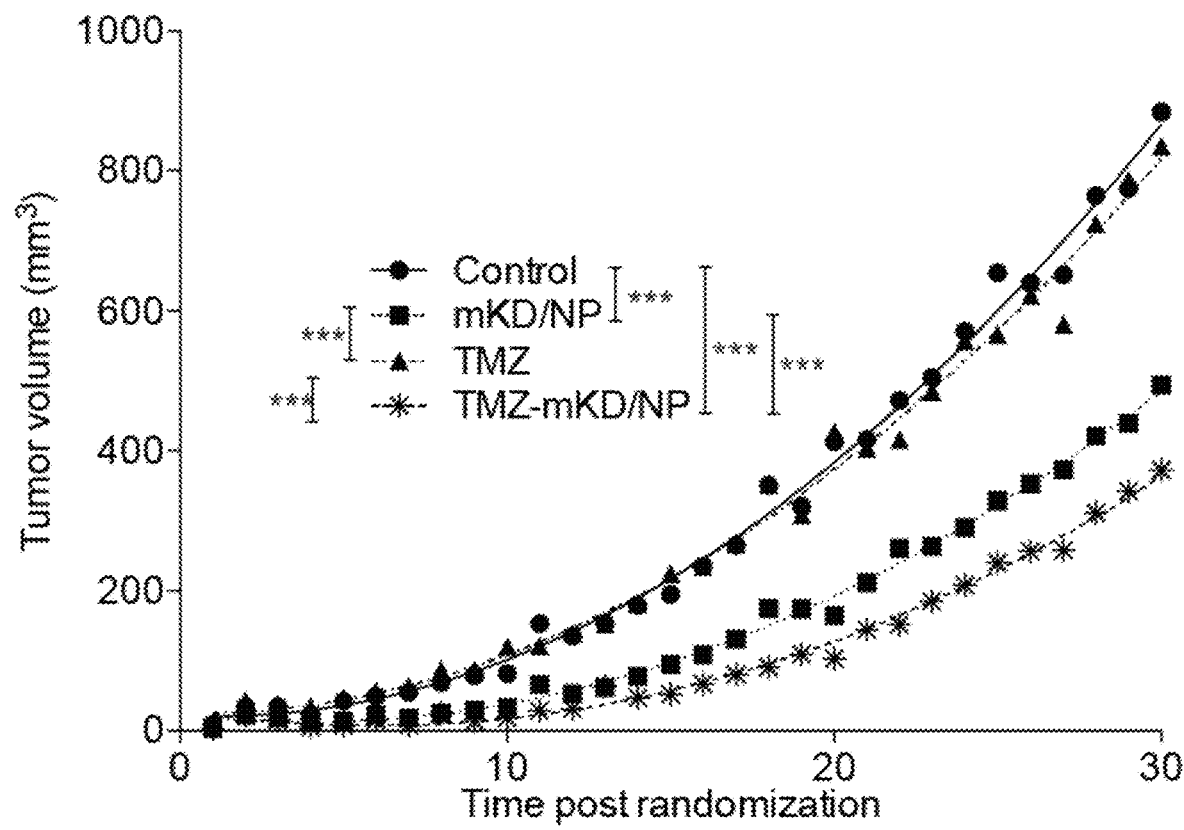
FIG. 29: Effect of mKD/NP on tumor progression of TMZ resistant cells. NOD/SCID animals were inoculated with 1M TMZ unresponsive hGB cells in the right flank. Tumor volume was monitored 3 times per week using a caliper and tumor volume was calculated. Treatments were initiated when a palpable mass was identified [approximately 65 mm$^3$]. Animals treated with mKD/NP demonstrated a significant slower tumor progression compared to controls demonstrating the efficacy of this treatment as a second line therapy after resistance to conventional treatment has been developed. The combination of standard of care (TMZ, 5 mg/kg) with mKD/NP showed a significant decrease of tumor progression compared to control, TMZ and mKD/NP treated groups. This result demonstrates the ability of mKD/NP to re-sensitize cells to conventional treatment after acquired resistance. ***, p<0.0001, two-way ANOVA.
Figure 62A:
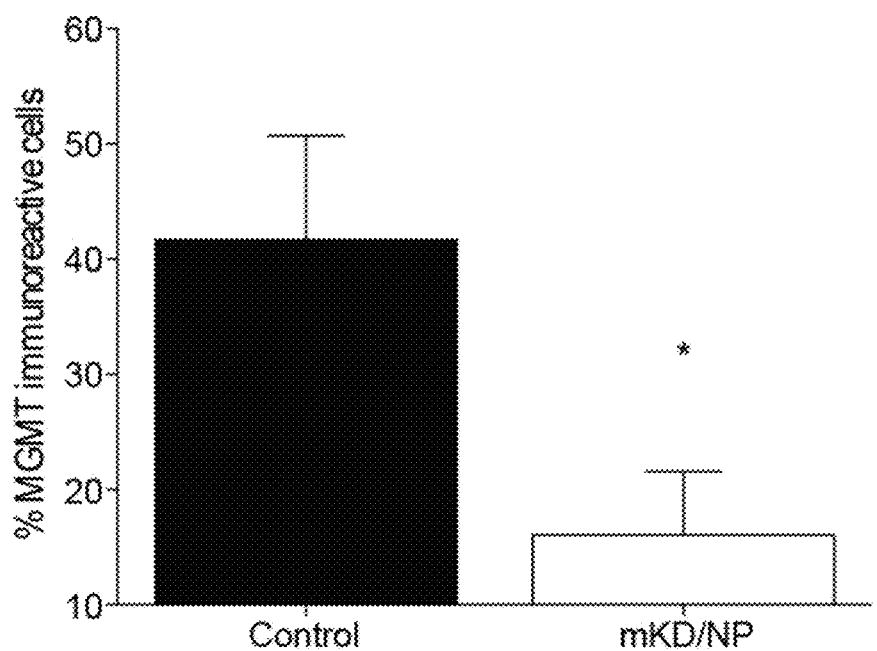
Figure 62B:
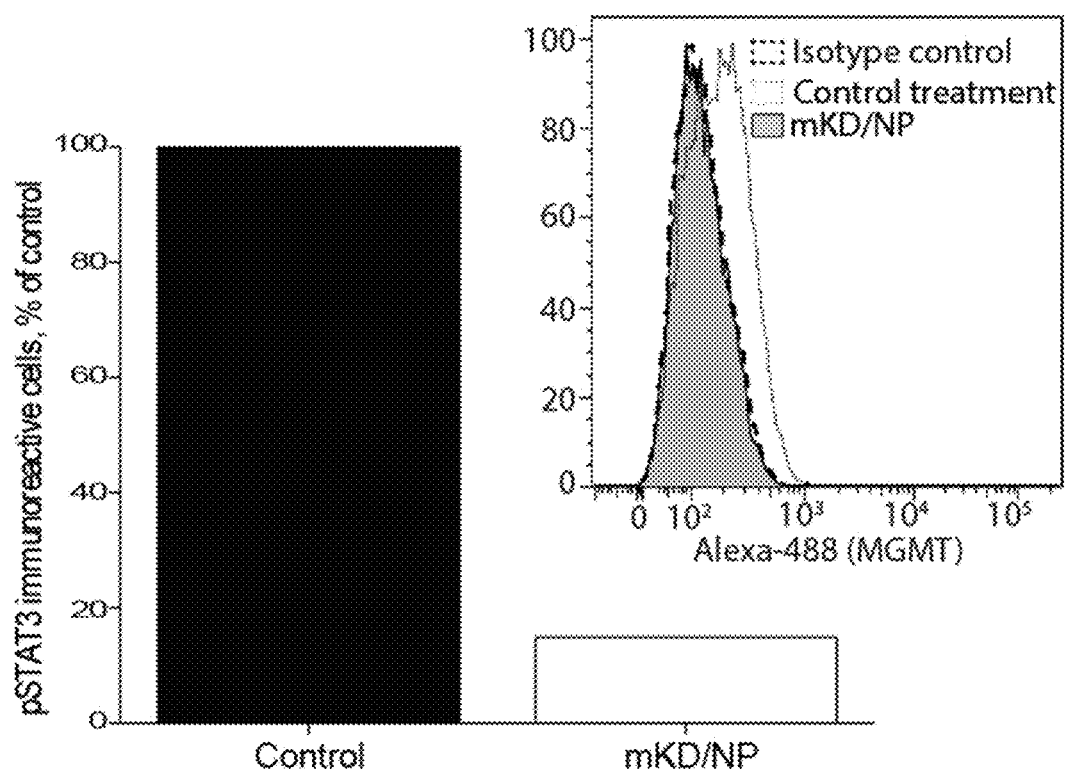

FIGS. 62A-62B: mKD/NP sensitization of tumor cells to TMZ via MGMT dependent mechanism (in vivo). NOD/SCID animals were inoculated with 1M hGB cells in the right flank. Tumor volume was monitored 3 times per week using a caliper. Treatments were initiated when a palpable mass was identified [approximately 65 mm$^3$]. Animals were sacrificed when they reached endpoint (1500 mm$^3$) and the tumors were harvested and prepared to quantify tumor cells expressing MGMT and pSTAT3. FIG. 62A) MGMT provides resistance to TMZ. The percentage of MGMT immunoreactive cells was quantified using flow cytometry. Animals treated with mKD/NP demonstrated a decrease of MGMT+ve cells compared to controls. p<0.05, t-test. FIG. 62B) Phosphorylation of Stat3 has been correlated with TMZ resistance through a mechanism dependent to MGMT (Kohsaka et al., 2012). The ability of mKD/NP to decrease Stat3 activation and MGMT expression provide a potential mechanism by which mKD/NP sensitize tumor cells to TMZ (described in FIG. 29) via a MGMT dependent mechanism.

Figure 63:
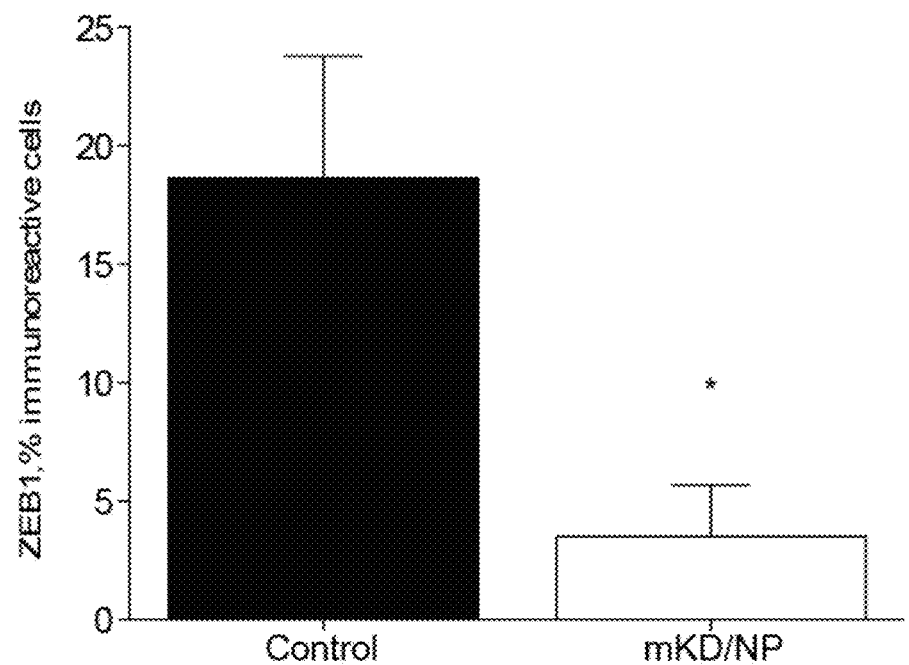

FIG. 63: Effect of mKD/NP on Zeb1 expression (in vivo). NOD/SCID animals were inoculated with 1M hGB cells in the right flank. Tumor volume was monitored 3 times per week using a caliper. Treatments were initiated when a palpable mass was identified [approximately 65 mm$^3$]. Animals were sacrificed when they reached endpoint (1500 mm$^3$) and the tumors were harvested and prepared to quantify tumor cells expressing ZEB1. ZEB1, a marker of tumor initiating cells, is an important candidate molecule for hGB recurrence, a marker of invasive tumor cells and a potential therapeutic target (Siebzehnrubl et al., under review). The percentage of ZEB1 immunoreactive cells was quantified using flow cytometry. Tumors derived from animals treated with mKD/NP demonstrated a significant decrease of ZEB1+ve cells compared to controls (*, p<0.05, t-test).

Figure 64:
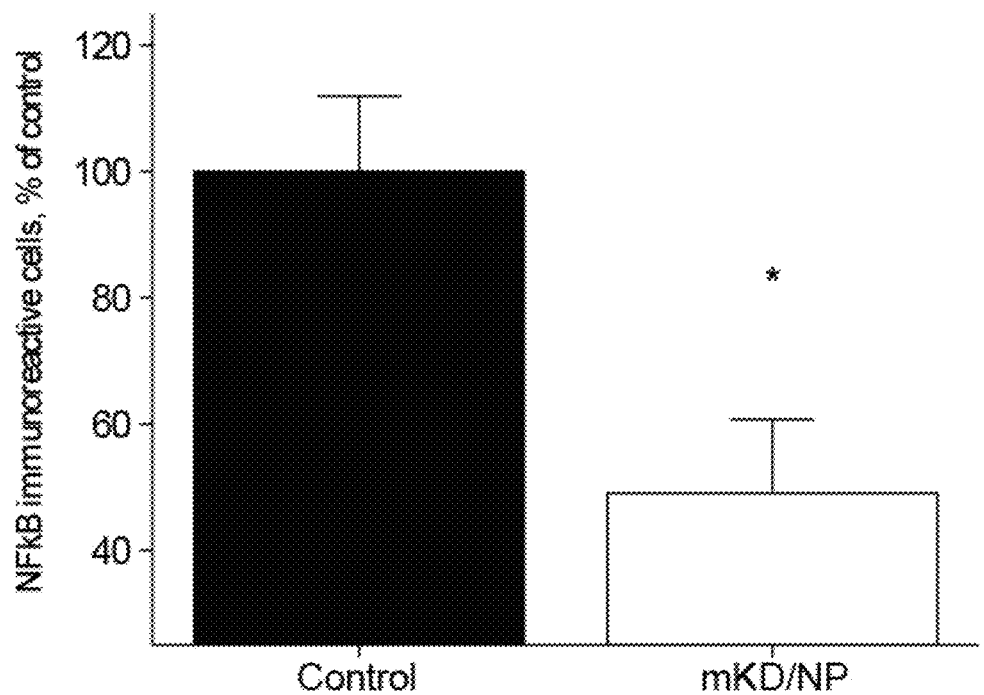

FIG. 64: Effect of mKD/NP on NFkB expression (in vivo). NOD/SCID animals were inoculated with 1M hGB cells in the right flank. Tumor volume was monitored 3 times per week using a caliper. Treatments were initiated when a palpable mass was identified [approximately 65 mm$^3$]. Animals were sacrificed when they reached endpoint (1500 mm$^3$) and the tumors were harvested and prepared to quantify by flow cytometry the percentage of tumor cells expressing NFkB. NFkB is an anti-apoptotic effector that also contribute to chemoresistance in hGB (Han et. al., 2004). Tumors derived from animals treated with mKD/NP demonstrated a significant decrease of NFkB+ve cells compared to controls (*, p<0.05, t-test).

Figure 65:
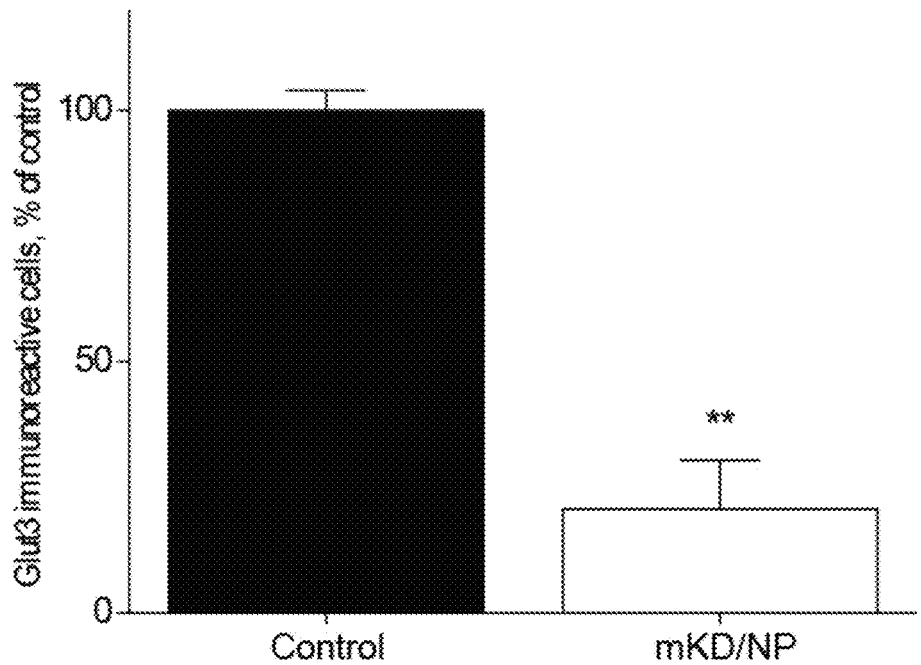

FIG. 65: Effect of mKD/NP on Glut3 expression (in vivo). Many tumor cells display increased level of glucose metabolism compared with normal cells. Glucose uptake is mediated by the glucose transporter (GLUT) family including Glut 3 that has been reported to be upregulated in glioblastoma (Boado et al., 1994) and to participate in the proliferation of tumor cells as well as in the acquired resistance to TMZ (Le Calve et al., 2010). These findings suggest that selective targeting of Glut3 would delay tumor cells proliferation and development of TMZ resistance. NOD/SCID animals were inoculated with 1M hGB cells in the right flank. Tumor volume was monitored 3 times per week using a caliper. Treatments were initiated when a palpable mass was identified [approximately 65 mm$^3$]. Animals were sacrificed when they reached endpoint (1500 mm$^3$) and the tumors were harvested and prepared to quantify by flow cytometry the percentage of tumor cells expressing Glut3. Tumors derived from animals treated with mKD/NP demonstrated a significant decrease of Glut3+ve cells compared to controls (**, p<0.005, t-test).

Figure 66A:
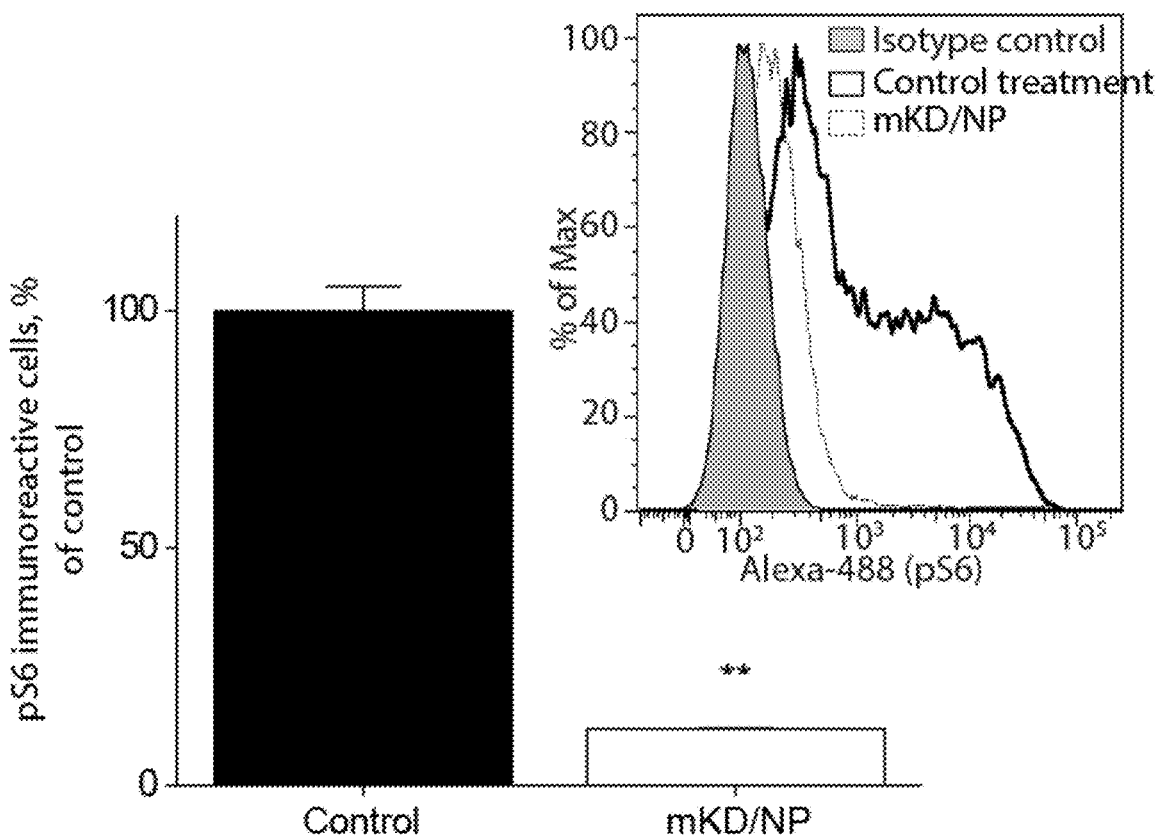
Figure 66B:
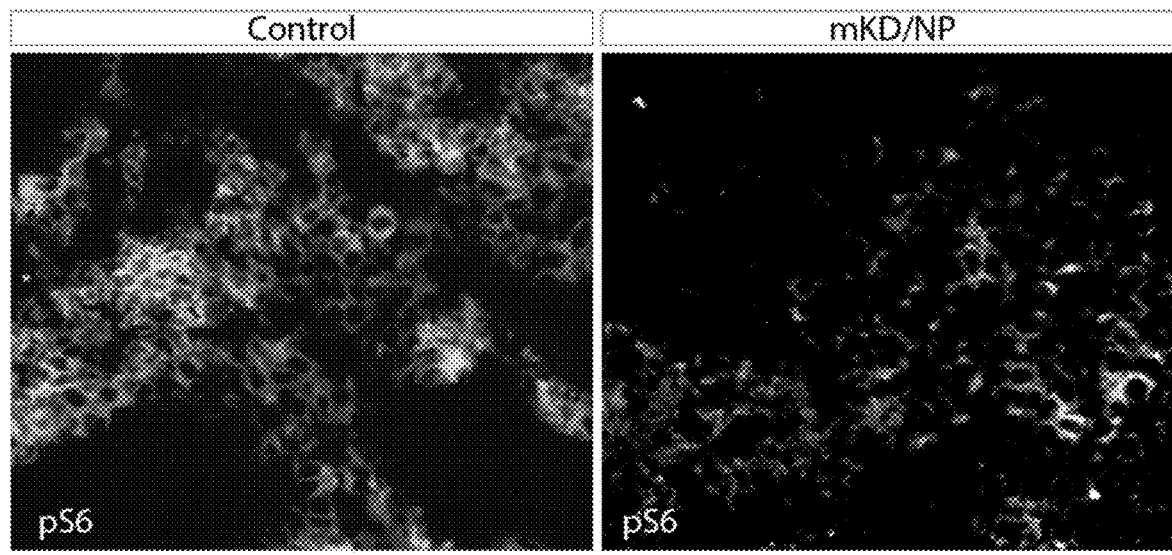
Figure 66C:
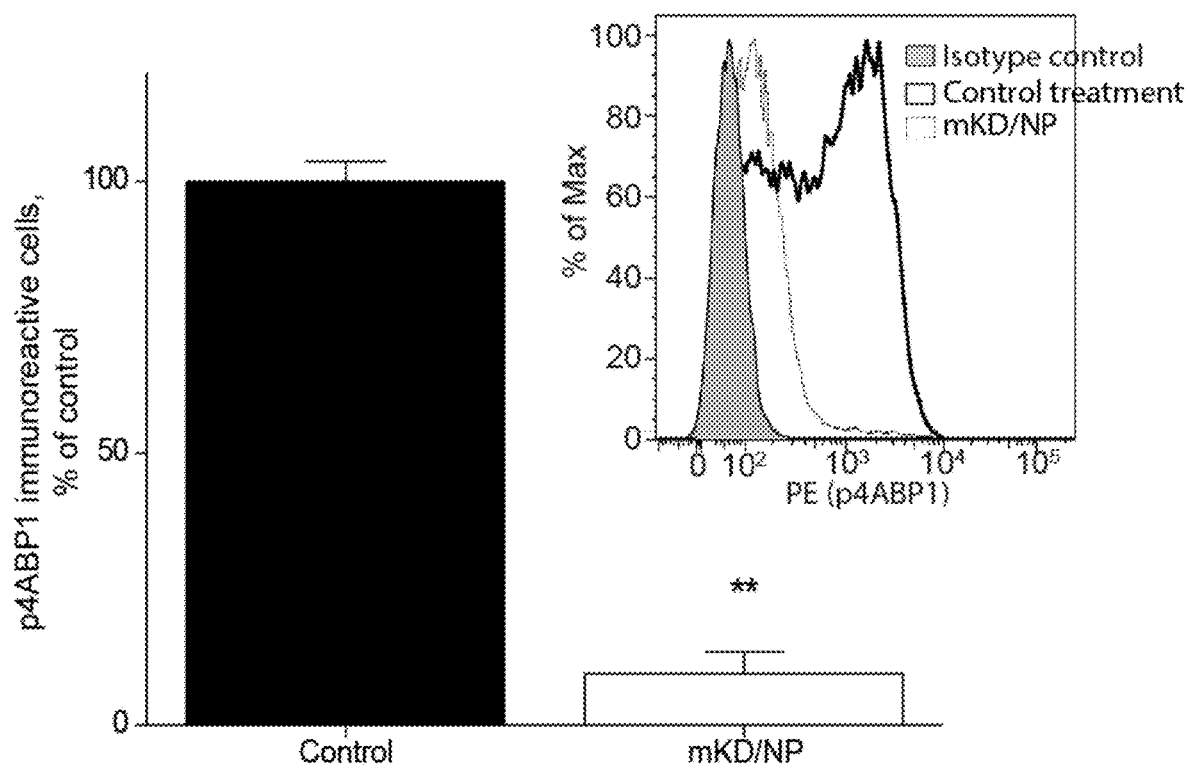
Figure 66D:
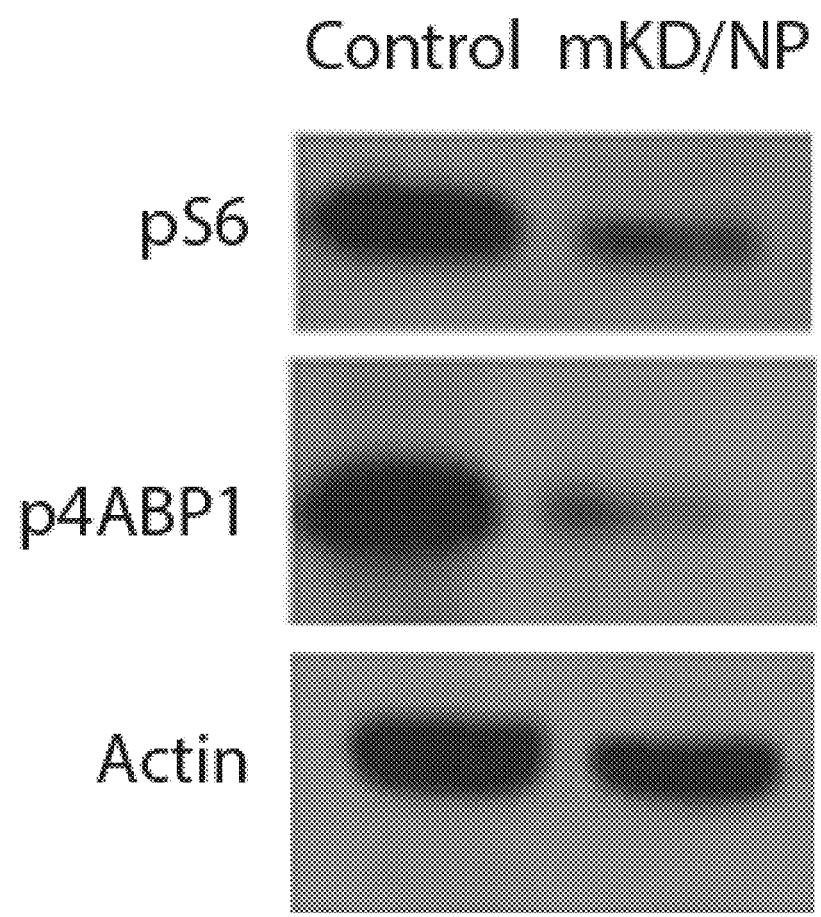

FIGS. 66A-66D: mTor pathway—In Vivo. mTor pathway is activated by growth factors, nutrients, energy and stress signals and is implicated in the control of cell growth, proliferation and survival. Deregulation of mTor pathway (e.g. up regulation of upstream activator such as AKT or downstream effectors such as S6 and 4EBP) has been reported in many cancers. mTor pathway is activated by the PI3K/AKT pathway. mTor activation leads to phosphorylation/activation of S6 and phosphorylation/inactivation of 4EBP, the 2 best characterized downstream effectors of mTor regulating ribosomal biogenesis and proteins synthesis respectively. Therefore mTor is an appealing therapeutic target and mTor pathway inhibitors represent potential candidates for viable therapeutic strategies. FIG. 66A) NOD/SCID animals were inoculated with 1M hGB cells in the right flank. Animals were sacrificed when they reached endpoint (1500 mm$^3$) and the tumors were harvested and prepared to quantify by flow cytometry the percentage of tumor cells expressing p-S6. Animals treated with mKD/NP demonstrated a significant decrease of pS6+ve cells compared to controls. (, p<0.005, t-test). FIG. 66B) Tissue specimens were harvested at endpoint and pS6 immunolabeling was compared between controls and mK/NP treated animals. Micrographs demonstrated a decreased pS6 staining in tumor treated with mKD/NP. FIG. 66C) NOD/SCID animals were inoculated with 1M hGB cells in the right flank. Animals were sacrificed when they reached endpoint (1500 mm$^3$) and the tumors were harvested and prepared to quantify by flow cytometry the percentage of tumor cells expressing p4ABP1. Animals treated with mKD/NP demonstrated a significant decrease of p4ABP1+ve cells compared to controls. (, p<0.005, t-test). FIG. 66D) WB: pS6 & p4EBP. Decreased expression of pS6 and p4ABP1 in the mKD/NP treated tumor was demonstrated by also Western Blot.

DETAILED DESCRIPTION OF THE INVENTION

A typical North American diet provides approximately 50 to 60% of its caloric intake from carbohydrates. As carbohydrates are the main source of glucose and the primary source of energy for glucose stored tumor cells, reducing carbohydrates through dietary restrictions can assist in lowering glucose levels and hence limiting tumor cell access to this fuel source. Thus, one aspect of the disclosed invention pertains to methods of treating a proliferative disorder in a subject comprising the administration, to the subject, of a composition comprising one or more component(s) selected from: epigallocatechin-3-gallate (EGCG); curcumin; glucosinolates and/or derivatives thereof, such as glucoraphanin and/or sulforaphane (SFN) (optionally in the form of broccoli sprouts, the sprouts of other cruciferous vegetables or cruciferous vegetables themselves) and, optionally, Daikon radish (in the form of mature radish, sprouts or powders of the radish, spouts or extracts thereof) alone or in combination with a low carbohydrate diet. The components can be administered individually as separate compositions or in various combinations (e.g., pairs, three-component compositions or a single composition containing all four or five components).

MCTs are fractionated from coconuts or palm kernel oils and are used clinically for patients with malabsorption symptoms. Due to their small molecular size MCT are digested rapidly traveling directly to the liver where they are quickly metabolized and lead to elevated blood ketones levels. Increased ketone and reduced glucose concentrations are the primary physiological effects of a ketogenic diet (for example, a diet composed of 90% fat and 10% proteins/carbohydrates).

EGCG is the most abundant catechin found in green tea. Curcumin is derived from turmeric.

Cruciferous vegetables contain a group of substances known as glucosinolates, which are sulfur-containing chemicals. During digestion, food preparation or chewing the glucosinolates are broken down into a number of biologically active compounds, these include, but are not limited to: indoles, nitriles, thiocyanates, isothiocyanates, Indole-3-carbinol and sulforaphane [SFN].

SFN is a bioactive molecule derived from the conversion of a glucosinolate precursor, glucoraphanin, found in cruciferous vegetables (for example, Brussels sprouts, cabbage, cauliflower, bok choy, kale, collards, Chinese broccoli, broccoli raab, kohlrabi, mustard, turnip, radish, arugula, and watercress). It is found in highest concentration in broccoli sprouts. Effective doses of glucosinolates, such as glucoraphanin and its biologically active breakdown products including SFN can be delivered by consumption of sprouts or sprout powders derived from the aforementioned cruciferous vegetables or plants from the genus *Brassica*. The phrases "composition(s) comprising glucosinolates and/or derivatives thereof, such as glucoraphanin and/or sulforaphane (SFN)" or "composition(s) comprising glucosinolates" or "composition(s) comprising glucoraphanin" or "composition(s) comprising SFN" may comprise one or more powders of mature plants of the genus *Brassica* or mature cruciferous vegetables, consumable vegetative matter of mature plants of the genus *Brassica* or mature cruciferous vegetables, dehydrated or non-dehydrated sprouts of plants of the genus *Brassica* or sprouts of cruciferous vegetables, or powdered sprouts obtained from cruciferous vegetables or from plants of the genus *Brassica*.

In some embodiments, the composition(s) comprising glucosinolates and/or derivatives thereof, such as glucoraphanin and/or sulforaphane (SFN) comprise powders of mature plants of the genus *Brassica* or mature cruciferous vegetables, consumable vegetative matter of mature plants of the genus *Brassica* or mature cruciferous vegetables, powders formed from dehydrated or non-dehydrated sprouts of plants of the genus *Brassica* or sprouts of cruciferous vegetables, or powdered sprouts obtained from cruciferous vegetables or from plants of the genus *Brassica*. As discussed above, powders from one or more cruciferous vegetable or plants from the genus *Brassica* can be combined into a composition comprising glucosinolates and/or derivatives thereof, such as glucoraphanin and/or sulforaphane (SFN). The powders discussed above may be provided in the form of freeze-dried powders. The administration of such powders delivers glucosinolates, including glucoraphanin, a compound subsequently metabolized to SFN by myrosinase, to the subject being treated. Daikon radish can be combined in with the components discussed above into compositions. Where Daikon radish is formulated into a composition comprising the various components discussed herein, it can be provided in the form of a powder (optionally freeze-dried), sprout, mature vegetable or a sprout powder (including dehydrated and/or freeze-dried sprout powders).

The current invention is directed to a treatment of proliferative disorders, for example, cancer. Thus, one aspect of the current invention provides a treatment of a proliferative disorder comprising administering to a subject in need of a treatment for the proliferative disease, a combination of compounds and, optionally, simultaneously providing the subject with a low carbohydrate diet or a modified ketogenic diet or a ketogenic diet. The combination of compounds to be administered to the subject comprise EGCG, curcumin, compositions comprising glucosinolates such as glucoraphanin and breakdown products such as SFN (these can be derived from broccoli sprouts or sprouts of other cruciferous vegetables or plants of the genus *Brassica*), and, optionally, Daikon radish sprout, a Daikon radish sprout extract or a powder of said extract, the Daikon radish or the Daikon radish sprout. These compounds (components) can be administered as a single composition or individually (as separate compositions/components) sequentially or simultaneously. This aspect of the invention can also provide for the restoration of normal cell proliferation for the proliferative disorder being treated. Thus, for various forms of cancer treated in this aspect of the invention, excessive cell proliferation associated with the proliferative disorder can be reduced or attenuated to levels at, or near normal proliferative levels for the particular cell giving rise to the proliferative disorder (e.g. a B-cell if B-cell lymphomas are being treated). Normal or near normal proliferative levels of cells are, generally, known in the art or can be determined by those skilled in the art. Thus, certain embodiments of the invention provide for reducing/attenuating the proliferation cells associated with a proliferative disorder by at least about 50%, 60%, 70%, 80%, 95% or more.

Various other aspects of the invention provide for the use of a composition comprising epigallocatechin-3-gallate, a composition comprising curcumin, and a composition comprising glucosinolates such as glucoraphanin and breakdown products such as SFN, and, optionally, a modified ketogenic diet or a ketogenic diet in subjects for the treatment of a proliferative disorder, decreasing the incidence of a proliferative disease in a subject, slowing the progression of a proliferative disease in a subject, increasing survival in a subject having a proliferative disease, enhancing the effect of conventional therapies for patients with proliferative diseases, sensitizing resistant cells to conventional therapies for patients with proliferative disease, reducing neuronal effects of chemotherapy in a subject treated with a chemotherapeutic regimen or reducing downregulation of neural stem cells (NSC) of the CNS in a subject developing a tumor or having a tumor or in a subject having a neurodegenerative disease or disorder. The compositions described above can be administered separately, separately in two, three or four component compositions or as a combined composition of all the components of the composition (including, optionally, Daikon radish sprouts, extracts thereof and/or powders thereof as described above). Slowing the progression of a proliferative disease in a subject relates to reducing the speed of a proliferative disease to advance overtime and can be measured, for example, as a reduction in increased volume of a tumor. Increasing survival in a subject having a proliferative disease relates to delaying the progression of proliferative diseases, in a subject and leads to an increased in the time of survival of a subject having a proliferative disease. Enhancing the effect of conventional therapies for patients with proliferative diseases relates to combining the disclosed method with conventional therapies used to treat subjects with proliferative diseases. This combination of therapies leads to positive outcomes equal to (additive effect) or greater than (synergistic effect) the individual effect of the conventional treatment and the disclosed method. Sensitizing resistant cells to conventional therapies for patients with proliferative disease relates to the ability of the disclosed method to convert proliferative diseases that were insensitive to conventional treatments used to treat patients with proliferative disease into proliferative diseases that respond to the conventional treatment to which the disease was, previously, unresponsive/refractory. Reducing neuronal effects of chemotherapy relates to reducing or preventing the decline of neural stem and progenitor cell activity observed when a subject undergoes chemotherapy.

The modified ketogenic diet is a diet that contains at least 5% and no more than about 20% carbohydrates (as a function of total caloric intake by the intake by the subject each day) and the balance of the diet for the subject comprises fats and proteins. Thus, the diet can, as a function of total caloric intake each day, contain about 5% to about 20% carbohydrates, about 30% to about 75% fats and about 5% to about 65% proteins. In certain embodiments, the diet can provides between about 8% and about 15% carbohydrates, about 50% to about 70% fats and about 18% to about 42% proteins. In some embodiments, from about 30% to about 70% (e.g., about 30%, about 40%, about 50%, about 60% or about 70%) of the fat content of the subject's diet can be made up of medium chain triglycerides (MCT). Other embodiments provide that MCT make up about 50% of the fat content of the subject's diet.

As a function of total amount of food (grams) based on a daily intake of 2000 kilocalories (and based on the fact that 1 g of carbohydrates provides 4 kilocalories, 1 g of fat provides 9 kilocalories, 1 g of proteins provides 4 kilocalories and 1 g of MCTs provide 6.8 kilocalories) the modified ketogenic diet is a diet that contains at least 25 g and no more than 100 g of carbohydrates and the balance of the diet for the subject comprises fats and proteins. Thus, the diet can, as a function of total grams intake each day, contain about 25 g to 100 g of carbohydrates, about 67 g to about 167 g of fats and about 25 g to about 325 g of proteins. In certain embodiments, the diet can provides between about 40 g and about 75 g of carbohydrates, about 111 g to about 155 g of fats and about 90 g to about 210 g of proteins. In some embodiments, from about 30% to about 70% (e.g., about 30%, about 40%, about 50%, about 60% or about 70%) of the fat content of the subject's diet can be made up of medium chain triglycerides (MCT). This represents from about 40 g to about 165 g of MCTs.

The ketogenic diet (KD) is a diet wherein the carbohydrate content is less than, or equal to, about 5% of the total caloric intake the subject each day and the balance of the diet consists of fats or proteins. Thus, the diet provides, as a function of total caloric intake each day, about 5% or less carbohydrate, about 30% to about 90% fat and about 5% to about 70% protein. In certain embodiments, the diet provides about 3% (or less) carbohydrate, about 57% to about 95% fat, about 5% to about 40% protein. In some embodiments, from about 30% to about 70% (e.g., about 30%, about 40%, about 50%, about 60% or about 70%) of the fat content of the subject's diet can be made up of medium chain triglycerides (MCT). Other embodiments provide that MCT make up about 50% of the fat content of the subject's diet.

In another embodiment of the invention, the treatment comprises providing, to a subject in need of a treatment for a proliferative disorder, a mKD or KD diet and, optionally, administering a composition comprising one or more of EGCG, curcumin, glucosinolates and, optionally, Daikon radish sprout. Various embodiments provide for the administration of a composition comprising EGCG, curcumin and glucosinolates or a composition comprising EGCG, curcumin, glucosinolates and Daikon radish sprout to the subject. In any aspect of the invention, the composition comprising one or more of EGCG, curcumin, compositions comprising glucosinolates such as glucoraphanin and its breakdown product SFN (which are found in high concentrations in broccoli sprouts or sprouts of other cruciferous vegetables or plants of the genus *Brassica*), and Daikon radish sprout or extracts thereof may be provided in the form of a powder or an extract produced from food products where at least one of these compounds are present naturally. Furthermore, compositions administered to a subject can be administered as a combination (e.g., each of EGCG, curcumin, compositions comprising glucosinolates such as glucoraphanin and its breakdown product SFN, and/or Daikon radish sprout in a single composition or each of the components (EGCG, curcumin, compositions comprising glucosinolates such as glucoraphanin and its breakdown product SFN, and Daikon radish sprout) can be provided (e.g., in the form of capsules, caplets tablets, powders, gels or other unit dosage forms) to the subject individually for simultaneous or sequential consumption.

Any of the aforementioned aspects of the invention for the treatment of a proliferative disorder or cancer may further comprise the administration of one or more additional anticancer therapy or therapies. Such therapies include, but are not limited to, radiotherapy, chemotherapy, surgery, immunotherapy, small molecule, kinase inhibition and/or monoclonal antibody therapy (e.g., rituximab for the treatment of B-cell lymphomas). In an embodiment of the invention the additional therapy comprises administration of temozolomide (TMZ).

In various other aspects of the invention, anti-cancer therapy or therapies are administered in addition to (in combination with) the treatment provided by the current invention. Such anti-cancer therapies include, but are not limited to, administering one or more of: Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Adriamycin (Doxorubicin Hydrochloride), Adrucil (Fluorouracil), Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Bendamustine Hydrochloride, BEP, Bevacizumab, Bexarotene, Bexxar (Tositumomab and I 131 Iodine Tositumomab), Bleomycin, Bortezomib, Bosulif (Bosutinib), Bosutinib, Brentuximab Vedotin, Cabazitaxel, Cabozantinib-S-Malate, CAF, Campath (Alemtuzumab), Camptosar (Irinotecan, ydrochloride), Capecitabine, CAPOX, Carboplatin, CARBOPLATIN-TAXOL, Carfilzomib, CeeNU (Lomustine), Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, Cosmegen (Dactinomycin), Crizotinib, CVP (COP), Cyclophosphamide, Cyfos (Ifosfamide), Cytarabine, Cytarabine, Liposomal, Cytosar-U (Cytarabine), Cytoxan (Cyclophosphamide), Dacarbazine, Dacogen, (Decitabine), Dactinomycin, Dasatinib, Daunorubicin Hydrochloride, Decitabine, Degarelix, Denileukin, iftitox, Denosumab, DepoCyt (Liposomal Cytarabine), DepoFoam (Liposomal Cytarabine), Dexrazoxane hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRINOX, FOLFOX, Folotyn (Pralatrexate), FU-LV, Fulvestrant, Gardasil (Recombinant HPV Quadrivalent Vaccine), Gefitinib, Gemcitabine Hydrochloride, GEMCITABINE-CISPLATIN, Gemtuzumab Ozogamicin, Gemzar (Gemcitabine, ydrochloride), Gleevec (Imatinib Mesylate), Glucarpidase, Halaven (Eribulin Mesylate), Herceptin (Trastuzumab), HPV Bivalent Vaccine, Recombinant, HPV Quadrivalent Vaccine (Recombinant), Hycamtin (Topotecan Hydrochloride), Ibritumomab Tiuxetan, ICE, Iclusig (Ponatinib Hydrochloride), Ifex (Ifosfamide), Ifosfamide, Ifosfamidum (Ifosfamide), Imatinib Mesylate, Imiquimod, Inlyta (Axitinib), Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Keoxifene (Raloxifene Hydrochloride), Kepivance (Palifermin), Kyprolis (Carfilzomib), Lapatinib Ditosylate, Lenalidomide, Letrozole, Leucovorin Calcium, Leukeran (Chlorambucil), Leuprolide Acetate, Levulan (Aminolevulinic (Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Marqibo (Vincristine Sulfate Liposome), Matulane (Procarbazine Hydrochloride), Mechlorethamine Hydrochloride, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitozytrex (Mitomycin C), MOPP, Mozobil (Plerixafor), Mustargen (Mechlorethamine hydrochloride), Mutamycin (Mitomycin C), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nolvadex (Tamoxifen Citrate), Nplate (Romiplostim), Ofatumumab, Omacetaxine, Mepesuccinate, Oncaspar (Pegaspargase), Ontak (Denileukin Diftitox), Oxaliplatin, Paclitaxel, Paclitaxel Albumin-stabilized Nanoparticle Formulation, Palifermin, Palonosetron Hydrochloride, Panitumumab, Paraplat (Carboplatin), Paraplatin (Carboplatin), Pazopanib Hydrochloride, Pegaspargase, Pemetrexed Disodium, Perjeta (Pertuzumab), Pertuzumab, Platinol (Cisplatin), Platinol-AQ (Cisplatin), Plerixafor, Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Raloxifene hydrochloride, Rasburicase, R-CHOP, R-CVP, Recombinant HPV Bivalent Vaccine, Recombinant HPV, Quadrivalent Vaccine, Regorafenib, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Sipuleucel-T, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Synovir (Thalidomide), Synribo (Omacetaxine Mepesuccinate), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Toposar (Etoposide), Topotecan Hydrochloride, Toremifene, Torisel (Temsirolimus), Tositumomab and I 131 Iodine Tositumomab, Totect (Dexrazoxane Hydrochloride), Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELOX, Xgeva (Denosumab), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoledronic Acid, Zolinza (Vorinostat), Zometa (Zoledronic Acid), and Zytiga (Abiraterone Acetate).

In certain aspects of the invention the proliferative disease to be treated by the current invention is not glioblastoma. However, the treatment of the current invention provides a meaningful treatment for a wide variety of other proliferative disorders. For example, the treatment provided by the current invention appears to be effective and non-toxic in preclinical models, which included brain, breast, colon, and lung cancer. Thus, the proliferative disorders that can be treated with the treatment of current invention include, but are not limited to, Acute Lymphoblastic Leukemia, Acute Myeloid Leukemia, Adrenocortical Carcinoma, AIDS-Related Cancers, AIDS-Related Lymphoma, Anal Cancer, Appendix Cancer, Astrocytoma, Cerebellar Astrocytoma, Basal Cell Carcinoma, Bile Duct Cancer, Extrahepatic Bladder Cancer, Bladder Cancer, Bone Cancer, Osteosarcoma and Malignant Fibrous Histiocytoma, Embryonal Tumors, Cerebral Astrocytoma, Ependymoblastoma, Medulloblastoma, Medulloepithelioma, Pineal Parenchymal Tumors of Intermediate Differentiation, Supratentorial Primitive Neuroectodermal Tumors and Pineoblastoma, Visual Pathway and Hypothalamic cancer, Brain and Spinal Cord Tumors, Breast Cancer, Bronchial Tumors, Burkitt Lymphoma, Carcinoid Tumor, Gastrointestinal Cancer, Carcinoma of Head and Neck, Central Nervous System Lymphoma, Cervical Cancer, Chronic Lymphocytic Leukemia, Chronic Myelogenous Leukemia, Chronic Myeloproliferative Disorders, Colorectal Cancer, Cutaneous T-Cell Lymphoma, Endometrial Cancer, Ependymoblastoma, Ependymoma, Esophageal Cancer, Ewing Family of Tumors, Extracranial Germ Cell Tumor, Extrahepatic Bile Duct Cancer, Eye Cancer, Intraocular Melanoma, Retinoblastoma, Gallbladder Cancer, Gastric (Stomach) Cancer, Gastrointestinal Carcinoid Tumor, Gastrointestinal Stromal Tumor (GIST), Extracranial Germ Cell Tumor, Germ Cell Tumor, Extragonadal Germ Cell Tumor, Ovarian Cancer, Gestational Trophoblastic Tumor, Hairy Cell Leukemia, Head and Neck Cancer, Hepatocellular (Liver) Cancer, Hepatocellular (Liver) Cancer, Hodgkin Lymphoma, Hypopharyngeal Cancer, Intraocular Melanoma Islet Cell Tumors (Endocrine Pancreas), Kaposi Sarcoma, Kidney (Renal Cell) Cancer, Kidney Cancer, Laryngeal Cancer, Chronic Lymphocytic Leukemia, Chronic Leukemia, Myelogenous Leukemia, Lip and Oral Cavity Cancer, Lung Cancer, Non-Small Cell Lung Cancer, Small Cell Lymphoma, Cutaneous T-Cell Lymphoma, Non-Hodgkin Lymphoma, Macroglobulinemia, Waldenström, Malignant Fibrous Histiocytoma of Bone and Osteosarcoma, Medulloblastoma, Medulloepithelioma, Melanoma, Intraocular Merkel Cell Carcinoma, Mesothelioma, Metastatic Squamous Neck Cancer with Occult Primary, Mouth Cancer, Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Myelogenous Leukemia, Multiple, Myeloproliferative Disorders, Nasal Cavity and Paranasal Sinus Cancer, Nasopharyngeal Cancer Neuroblastoma, Non-Small Cell Lung Cancer, Oral Cancer, Oral Cavity Cancer, Lip and Oropharyngeal Cancer, Osteosarcoma and Malignant Fibrous Histiocytoma of Bone, Ovarian Epithelial Cancer, Ovarian Germ Cell Tumor, Ovarian Low Malignant Potential Tumor, Pancreatic Cancer, Pancreatic Cancer, Islet Cell Tumors, Papillomatosis, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Primary Central Nervous System Lymphoma, Prostate Cancer, Rectal Cancer, Renal Cell (Kidney) Cancer, Renal Pelvis and Ureter Cancer, Transitional Cell Cancer, Respiratory Tract Carcinoma Involving the NUT Gene on Chromosome 15, Retinoblastoma, Rhabdomyosarcoma, Salivary Gland Cancer, Sarcoma, Ewing Family of Tumors Sarcoma, Kaposi Sarcoma, Soft Tissue Sarcoma, Uterine Sezary Syndrome, Skin Cancer (Nonmelanoma), Skin Carcinoma, Merkel Cell, Small Cell Lung Cancer, Small Intestine Cancer, Squamous Cell Carcinoma, Squamous Neck Cancer with Occult Primary Cancer, Supratentorial Primitive Neuroectodermal Tumors, T-Cell Lymphoma, Mycosis Fungoides and Sezary Syndrome, Testicular Cancer, Throat Cancer, Thymoma and Thymic Carcinoma, Thyroid Cancer, Transitional Cell Cancer of the Renal Pelvis and Ureter, Gestational Trophoblastic Tumor, Carcinoma of Unknown Primary Site, Urethral Cancer, Uterine Cancer, Endometrial Uterine Sarcoma, Vaginal Cancer, Vulvar Cancer, Waldenström Macroglobulinemia, and Wilms Tumor.

A further aspect of the invention provides a composition comprising MCT, ECGC, curcumin, and compositions comprising glucosinolates and/or derivatives thereof, such as glucoraphanin and/or sulforaphane (SFN) in the form of a powder, drink, emulsion, gel, or mixture thereof. An even further aspect of the invention provides a composition comprising MCT, ECGC, curcumin, compositions comprising glucosinolates and/or derivatives thereof, such as glucoraphanin and/or sulforaphane (SFN), and Daikon radish sprout or extracts of ECGC, curcumin, compositions comprising glucosinolates and/or derivatives thereof, such as glucoraphanin and/or sulforaphane (SFN), and Daikon radish thereof in the form of a capsule, tablet, powder, drink, emulsion, gel, or mixture thereof. A subject in need of a treatment for a proliferative disease or sparing of NSC downregulation may ingest the composition provided by the current invention either directly or by mixing it with other foods or drinks, for example, water, fruit juice, yogurt, soups, stews, pasta, etc. Further, the composition (or individual components) can also be incorporated into other food products, for example, cake, cookies, cereal bars, etc.

All patents, patent applications, provisional applications, and publications referred to or cited herein are incorporated by reference in their entirety, including all Figures and tables, to the extent they are not inconsistent with the explicit teachings of this specification.

Following are examples, which illustrate procedures for practicing the invention. These examples should not be construed as limiting. All percentages are by weight or by calories and all solvent mixture proportions are by volume unless otherwise noted.

Example 1: The Modified Ketogenic Diet [mKD] Alters Glucose and Ketone Levels to the Same Extent as the Ketogenic Diet [KD]

NOD-SCID animals were placed on a KD or mKD or mKD+EDP for two weeks. The compositions of the diets are as follows (expressed as percentage of calories):

Control diet: Is a standard mouse chow and is composed of 55% carbohydrate, 30% protein, 15% fat.

KD: 92% Fat, 3% carbohydrate, 5% protein.

mKD: 10% carbohydrate, 60% Fat (half coming from medium chain triglycerides [MCT, Neobee 598]), 30% Protein.

NP diet: 55% carbohydrate, 30% protein, 15% fat+Sulforaphane (SFN; 25 mg/kg; BSP95%/DRSP5%), Curcumin (1200 mg/kg), EGCG (1200 mg/kg).

mKD/NP: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg).

Ten animals, in each dietary group, were placed on the modified diet for 2 weeks at which point tail tip method was used to collect blood via the following protocol: "Using a 50 mL conical (or mouse restrainer) place a non-anesthetized mouse gently inside grasping the mouse by the tail. Place the mouse's tail on a hard surface. Using a scalpel cut off less than 1 mm of the tip of the tail. Place your fingers at the base of the tail and gently squeeze upward running your fingers from base to tip of the tail. One to two drops of blood (5-10 µL) will appear at the tip of the tail. Using a dry gauze wipe away first few drops of blood and repeat steps until desired amount of blood is collected (should be dark, whole blood, clear [plasma like] blood will give you an inconsistent blood reading). Place the mouse back into the cage and monitor for excess bleeding."

Figure 1:
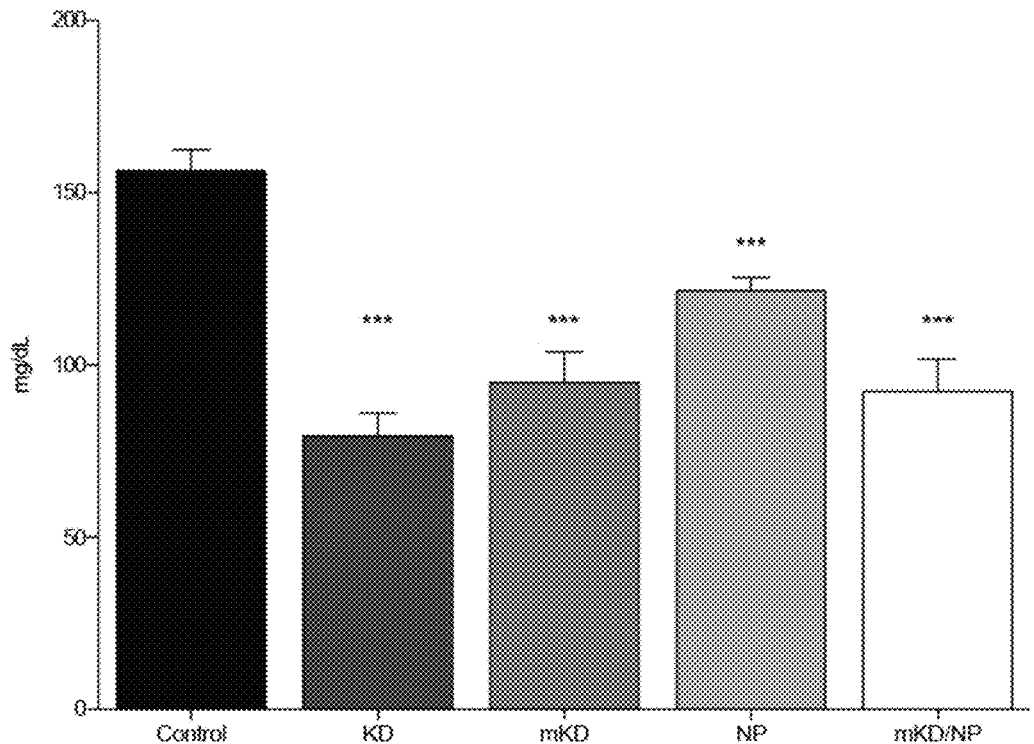
FIG. 1: Effect of mKD on blood glucose levels. Blood glucose level was compared between animals that were fed respectively for 2 weeks with the different diets [control, ketogenic diet (KD), modified ketogenic diet (mKD) or mKD/NP]. Glucose level was similar between the KD, mKD, Natural Products (NP) and mKD/NP groups, which were significantly decreased compared to control. *, ***, compared to control, p<0.01, 0.001, 1-way ANOVA. Treatments composition is as follow: Control (55% carbohydrate, 30% protein, 15% fat), KD (92% Fat, 3% carbohydrate, 5% protein), mKD=10% carbohydrate, 60% Fat (half coming from MCT, Neobee 598), 30% Protein, Natural Products (NP) [55% carbohydrate, 30% protein, 15% fat+SFN (25 mg/kg; BSP95%/DRSP5%), Curcumin (1200 mg/kg), EGCG (1200 mg/kg)], mKD/NP=mKD+Natural Products (NP).
Figure 2:
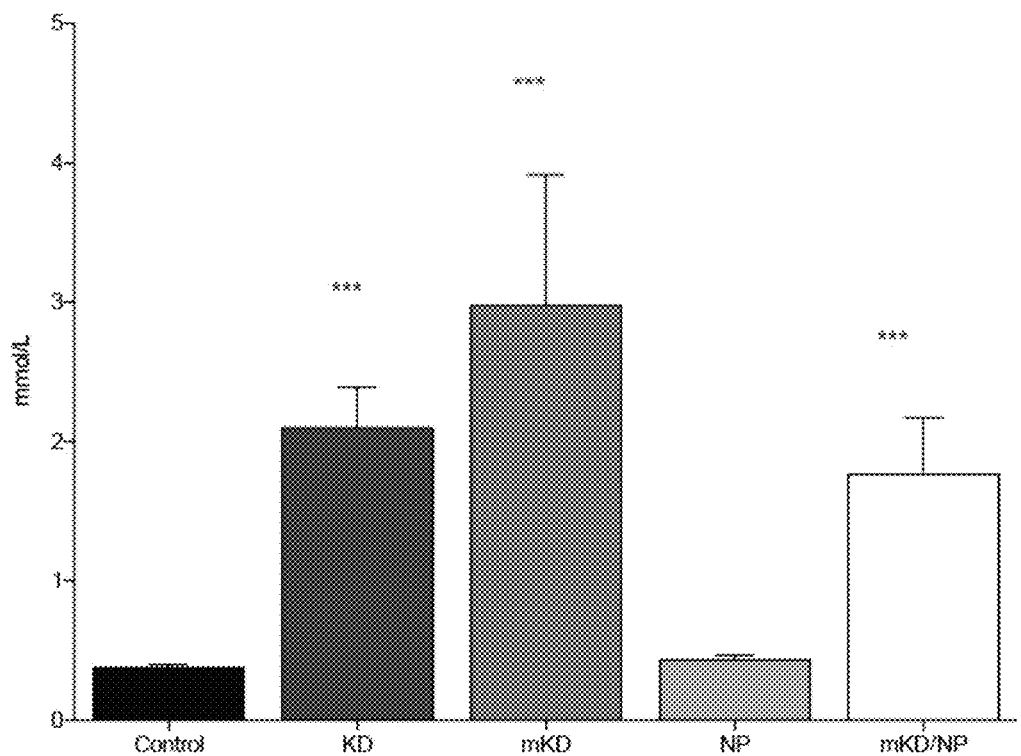
FIG. 2: Effect of mKD on blood ketone levels. Blood ketones levels was compared between animals that were fed respectively for 2 weeks with the different diets [control, ketogenic diet (KD), modified ketogenic diet (mKD) or mKD/NP]. Ketones level was similar between the KD, mKD, Natural Products (NP) and mKD/NP groups, which were significantly decreased compared to control. ***, compared to control, p<0.001, 1-way ANOVA. Treatments composition is as follow: Control (55% carbohydrate, 30% protein, 15% fat), KD (92% Fat, 3% carbohydrate, 5% protein), mKD=10% carbohydrate, 60% Fat (half coming from MCT, Neobee 598), 30% Protein, Natural Products (NP) [55% carbohydrate, 30% protein, 15% fat+SFN (25 mg/kg; BSP95%/DRSP5%), Curcumin (1200 mg/kg), EGCG (1200 mg/kg)], mKD/NP=mKD+Natural Products (NP).

Blood samples were analyzed with Precision Xtra blood glucose/ketone monitor and expressed in mg/dl and mmol for glucose and ketones, respectively. With regards to glucose levels, all 4 experimental diets resulted in a significant reduction in glucose [FIG. 1, $p<0.001$]. Similarly, ketone levels were elevated in all the dietary groups except for the NP diet [FIG. 2, $p<0.001$]. These data demonstrate that the mKD and mKD/NP diet is able to mimic the two key physiological features of the KD, a significant reduction in glucose and a significant increase in ketones.

Example 2: The mKD/NP Diet is Safe and has No Signs of Toxicity

Figure 3:
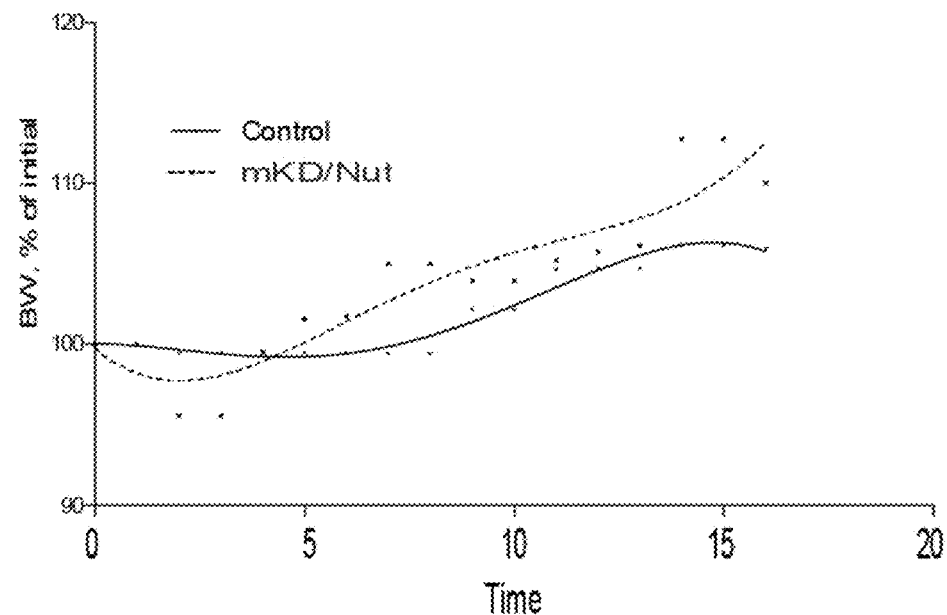
FIG. 3: Effect of mKD/NP on body weight. Toxicity of mKD/NP was assessed by monitoring body weight over 16 days. Over the course of the study the mKD/NP treated animals did not lose weight and even shown and increased body weight compared to control animals. p<0.005, Linear regression.

The vast majority of cancer therapeutics has dose-limiting toxic side effects that impact not only a patient's well-being but it also results in suspended treatments and reduced dosages that can impact treatment efficacy. One of the best indicators of overall health in a rodent is its body weight [this is true in human patients as well]. NOD-SCID animals received 1M GB cells [patient derived lines] into the right flank. Animals were monitored 3 times per week for signs of tumor formation. Once a tumor was identified [by palpation & approximately 65 $mm^3$]] animals were randomly assigned to 1 or 2 groups: [1] Control diet or [2] mKD/NP diet. Body weight was monitored 3 times per week. FIG. 3 depicts percentage change in body weight till the first control animal reached endpoint [16 days]. While the mKD/NP group initially lost weight over the first few days [due to adjusting to a new diet], they quickly recovered the lost weight and continued to gain weight at a significantly greater rate than the control group [$p<0.005$, linear regression, GraphPad].

When animals reached endpoint blood was collected via intracardiac or retro-orbital puncture and blood samples were sent to Comprehensive Clinical Pathology Services, LLC for the following analysis:

[1] Alkaline phosphatase [ALP]—liver, bones and pancreas function test

[2] Alanine transaminase [ALT]—liver function test

[3] Aspartate animotransferase [AST]—liver function test

[3] Creatinine—kidney function test

Figure 4:
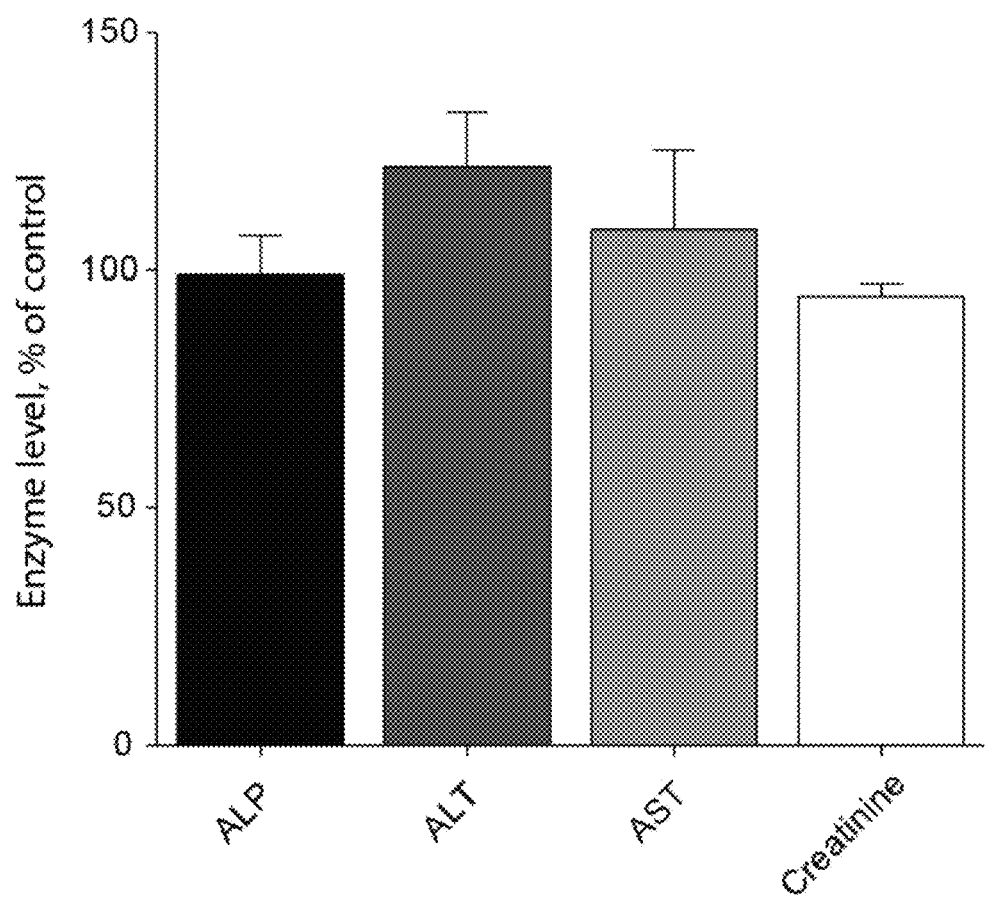
FIG. 4: Toxicology—Blood tests. Toxicity was assessed after 4 weeks of treatment (mKD/NP) via plasma measurements of the following analytes (Comparative Clinical Pathology Services, LLC): creatinine (kidney), alanine transaminase (ALT, liver), aspartate aminotransferase (AST, liver), and alkaline phosphatase (ALP, pancreas). No difference was observed between mKD/NP treated animals compared to controls. p>0.1, 1-sample t-test.

FIG. 4 reveals no statistically significant differences in liver, kidney, bones and pancreas function between the control and mKD/NP feed animals. Together, FIGS. 3 and 4, support the conclusion that mKD/NP diet is safe and has no noted toxic side effects.

Example 3: Comparison of Safety Between Standard of Care [SOC] Vs. mKD/NP

Figure 5:
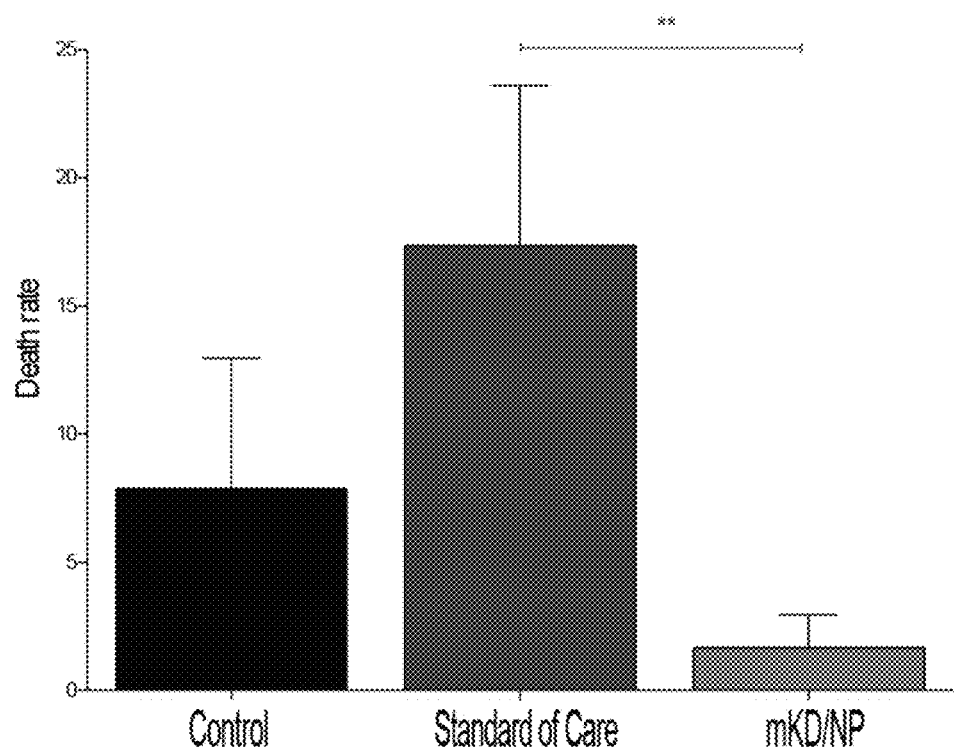
FIG. 5: Non-Tumor Death—TMZ vs. mKD/NP. Mortality rate unrelated to tumor was monitored during the course of treatments. Compared to conventional therapy (Temozolomide [TMZ], 20 mg/kg), mKD/NP treatment decreased mortality by 10 fold. **, p<0.01, t-test.

The first line chemotherapy for high grade gliomas is temozolomide [TMZ], which is an oral alkylating agent that damages DNA and triggers cell death. While TMZ is an effective chemotherapy agent it also has significant toxicity. Using the same subcutaneous model as noted in example 2, at the time of tumor presentation animals were randomly assigned to one of three groups: [1] control diet, no treatment; [2] control diet, SOC [TMZ, 20 mg/kg three times/week]; [3] mKD/NP diet. We analyzed the number of animals that died as a result of non-tumor related causes and noted that SOC treatment resulted in an increase in mortality compared to the untreated controls [FIG. 5]. A similar increase in mortality was not seen in the mKD/NP group, where the death rate was not statistically different than the controls but was significantly lower than the SOC group.

Figure 6:
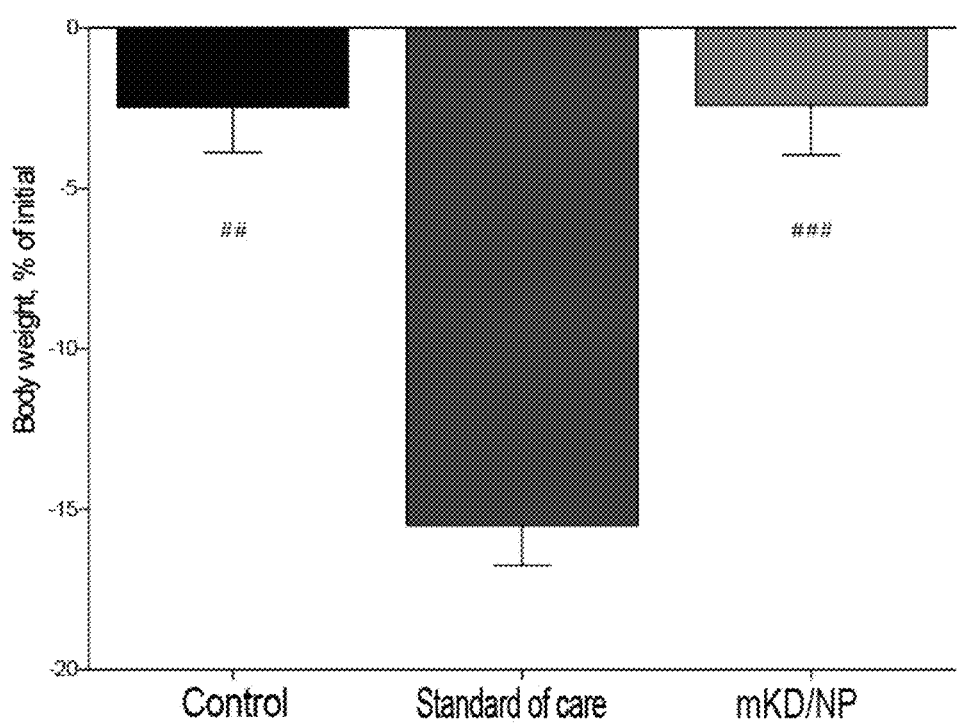
FIG. 6: Body weight—TMZ vs. mKD/NP. Toxicity/safety of mKD/NP was compared to standard of care (TMZ, 20 mg/kg) by monitoring body weight after 4 days of treatment. No difference was observed between control and mKD/NP treated animals (p>0.05, 1-way ANOVA) whereas animals treated with conventional treatment showed significant loss of body weight compared to control and mKD/NP. ##, ###, p<0.001, p<0.0001, 1-way ANOVA, compared to TMZ.

While receiving SOC treatment, body weight was measured and not surprisingly was significantly reduced in the SOC group relative to the control and mKD/NP treated animals [FIG. 6]. It is important to note that mKD/NP treatment was as effective as SOC [see example 11]. Hence, these data teach that mKD/NP has no adverse effects on overall health [as defined by body weight] and does not directly affect mortality, unlike SOC that affects overall health and results in increased mortality.

Example 4: Natural Products [NP] Provide Effective Cancer Treatment

Patient derived hGB cells were cultured under defined conditions using established protocols that allow the tumor cells to retain both their phenotypic and genotypic properties in vitro. hGB cell lines were treated with the following NPs:

[1] EGCG-8 µM

[2] Curcumin-0.5 µM

[3] SFN-2.5 µM

[4] a combination of all three NPs

Figure 7:
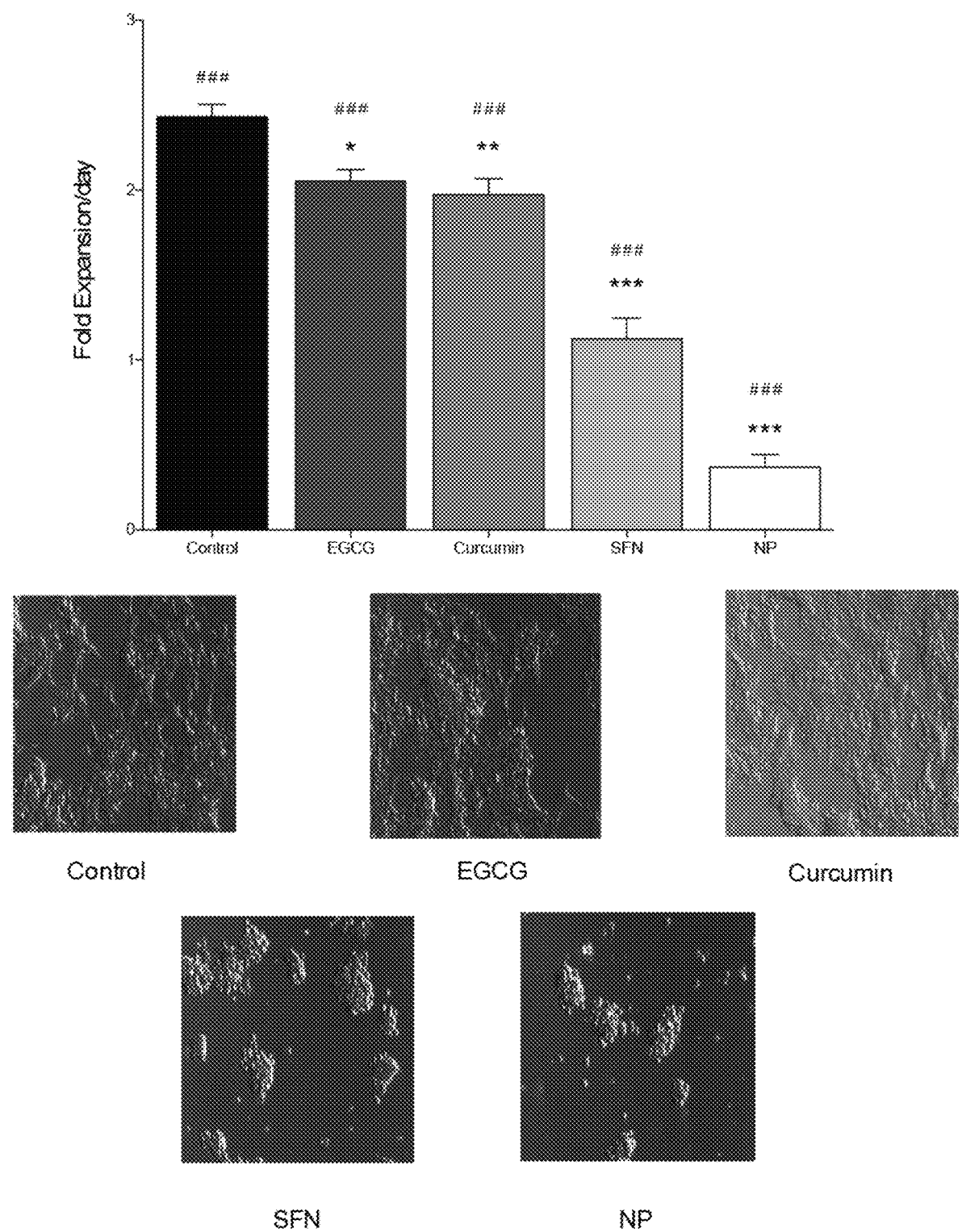
FIG. 7: NP in vitro-Fold Expansion. Primary human GBM stem cell lines were treated daily for 4 out of 5 days in culture with EGCG (8 µM), Curcumin (0.5 µM) and sulforaphane (2.5 µM) or a combination of all three NPs (E+C+S). Cells were passed after 5-7 days and cell counts were performed. All individual compounds exhibited a significant reduction in mean daily fold expansion of GB cells. The combination of the three natural products (NP) together demonstrated the strongest effect. The synergistic effect of the combination suggests that each component of NP is affecting non-overlapping mechanisms. *, ***, p<0.01, p<0.01, p<0.0001, 1-way ANOVA, compared to control. # # #, p<0.001, 1-way ANOVA, compared to NP. Micrographs show cultures after 4 days of exposure to the different treatments.

Each of the NPs resulted in a significant reduction in the overall number of cells that were produced relative to the control cultures [FIG. 7]. However, the simultaneous application of all three NPs resulted in a synergistic effect with regards to reducing the production of new cells. These data support the hypothesis that each of the NPs exert their effect by different mechanisms.

One million hGB cells were implanted into the right flank of NOD-SCID mice, and at the time that a palpable tumor was identified the animals were randomized into one of 5 groups:

[1] Control diet

[2] Control diet+EGCG [1200 mg/kg]

[3] Control diet+Curcumin [1200 mg/kg]

[4] Control diet+SFN [25 mg/kg; BSP95%/DRSP5%]

[5] Control diet+EGCG/Curcumin/SFN [same concentrations as group 2-4]

Figure 8:
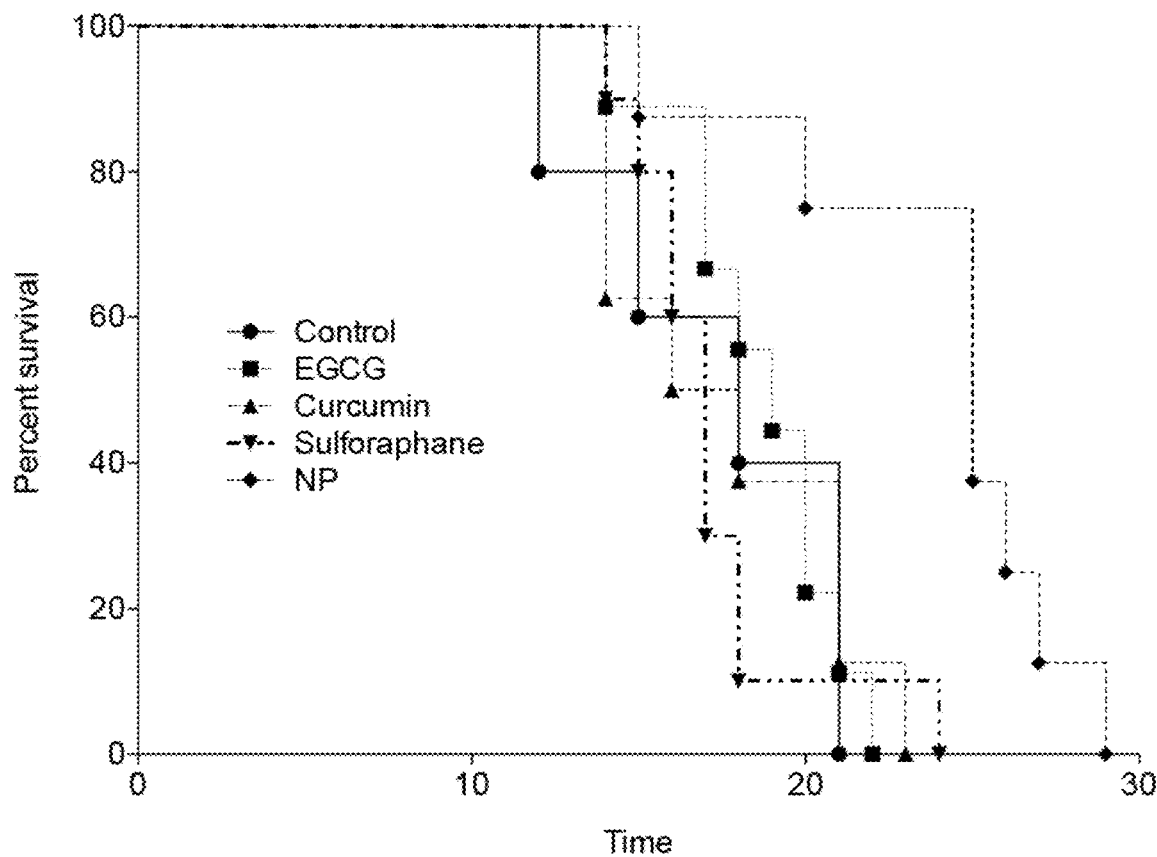
FIG. 8: Kaplan-Meier (KM) survival curves—Individual NPs vs. Combination. NOD/SCID animals were inoculated with 1M hGB cells in the right flank. Tumor progression was followed using calipers by recording 2 measurements of tumor diameter and converting this into a volume using the following formula: $(4/3)\pi R^3$. For spheroid tumors the two measurements were averaged to determine the diameter of the sphere. In the case of ellipsoid tumors (i.e. prolate or oblate spheroid mass) the formula used was: $(4/3)\pi *(d/2)*(d/2)^2$. In this case the second measurement "$d^2$" would count twice and "d" only once. For prolate spheroids, the long measurement occurs once while the short measurement occurs twice. Conversely, for the oblate spheroid tumors, the long measurement occurs twice while the short one occurs only once. Following this criteria, tumor volume was tracked over time. Treatments were initiated when a palpable mass was identified [approximately 65 mm$^3$]. Animals were sacrificed when they reached endpoint (tumor volume of 1700 mm$^3$). The fraction of animals living as a function of time is represented using Kaplan-Meier survival curves. Animals treated with NP demonstrated a significant improvement over controls or animals treated with individual component (*, **, p<0.05, p<0.005, Log rank test).

Animals were kept on their respective diets till tumors reached endpoint [1500 mm3] and they were killed. Kaplan Meier survival curves were generated using GraphPad. While groups 2-4 did not live longer than the control animals, those treated with all three natural products [Group 5] did live significantly longer [FIG. 8]. These data support the synergistic actions of combining the three NPs and their effect on reducing tumor progression and enhancing lifespan.

Together the data teaches that our unique combination of NPs has an synergistic effect in vitro but a synergistic action in vivo, indicating that this particular combination produces an unexpected anti-cancer effect and as such is defined as a unique polymolecular botanical drug.

Figure 9A:
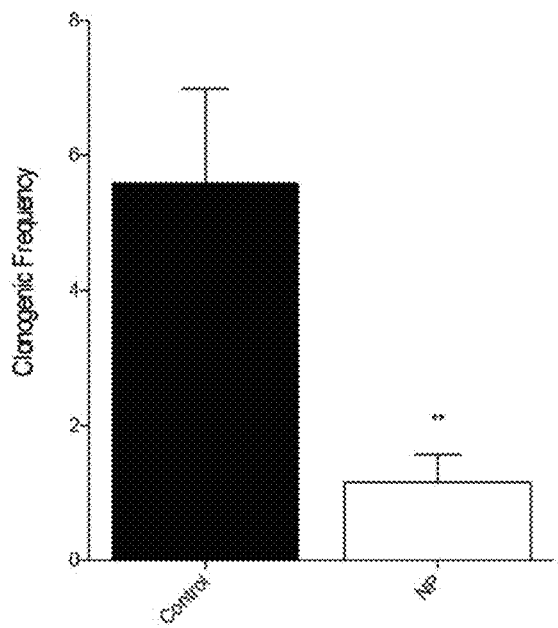
FIGS. 9A-9B: NP—Effect on cancer stem cells (CSCs). Patient derived GB cell lines cultured in defined medium were treated with NP. After 5-7 days in culture, spheres were harvested, dissociated into single cells suspension and plated at low density in 96 well plates in control conditions. Seven to ten days later the number of spheres was counted (FIG. 9A: clonogenic frequency) and sized (FIG. 9B). This assay is able to access the effects of treatment on the sphere forming cells (i.e clonogenic frequency in FIG. 9A) and on the proliferative potential of each of the clones (FIG. 9B). Exposure of human GB cells to NPs for 7 days in vitro results in a significant reduction in the clonogenic frequency and the proliferative ability of the clones. **, p<0.01, t-test.
Figure 9B:
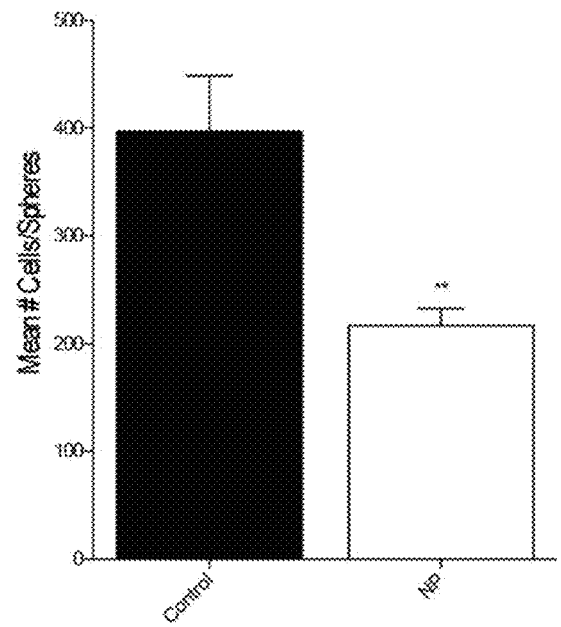

Example 5: Natural Products [NPs] Target the Proliferating Tumor Cells and Cancer Stem Cells Patient derived hGB cells were cultured for 5-7 days in the presence of the following NPs:

[1] EGCG-8 µM; [2] curcumin-0.5 µM; [3] Sulforaphane-2.5 µM. Cells were then dissociated into a single cell suspension and plated at a low density in 96 well plates together with control nutrient growth medium [NeuroCult+EGF]. At this stage cells were no longer exposed to NPs. After being cultured for 7-10 days in the 96 well plates, the number of spheres was counted [to determine the clonogenic frequency] and the spheres were sized [to determine the proliferative capacity of each clone forming cell]. Cells in 96-well plates were first fixed with a 4% paraformaldehyde solution containing 0.2% Triton-X and 1:1000 dilution of DAPI. Fluorescent images were taken and the number of spheres and their size quantitated using Macnification. Data was exported to excel and statistical analysis done in GraphPad. FIG. 9 details the results of this experiment and demonstrates the ability of our NP combination to reduce the pool of proliferating clone forming precursor cells and to reduce the proliferative ability of the clones. As cancer is a disease defined by the uncontrolled growth of clonogenic cancer cells, the ability of our NPs to reduce the number of clones and to reduce the proliferative potential of the existing clones points to the novelty and utility of our findings.

In a second experiment [FIG. 10], patient derived hGB cells were serially passed in culture while being treated with the following NPs:

[1] EGCG-8 µM

[2] Curcumin-0.5 µM

[3] SFN-2.5 µM

[4] A combination of all three NPs

Figure 10A:
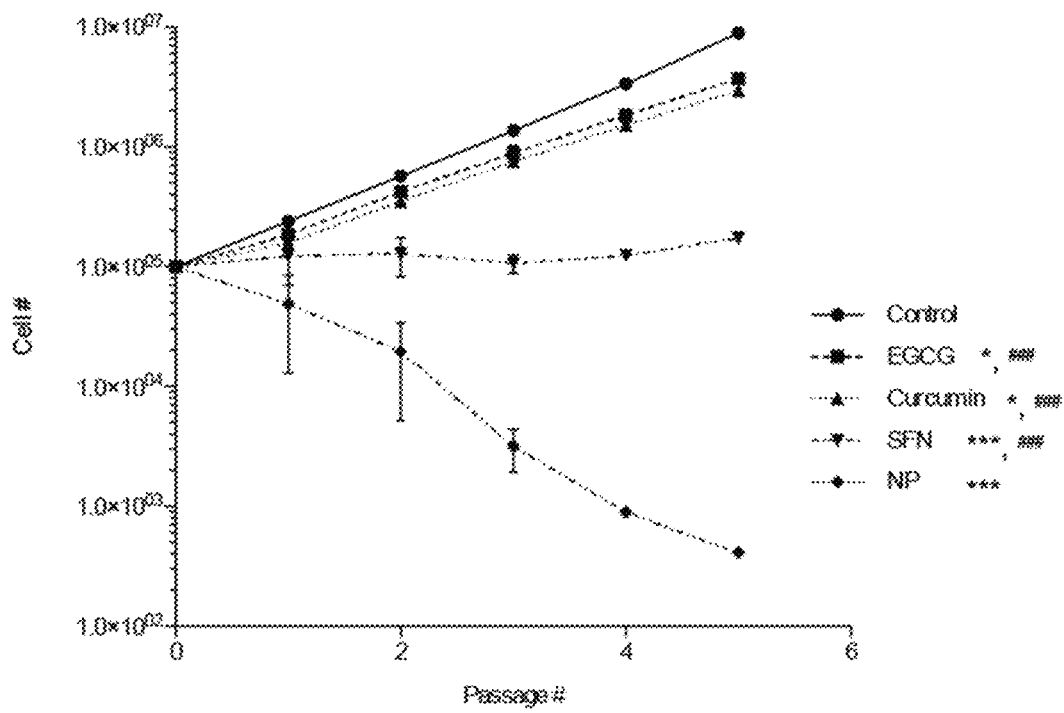
FIGS. 10A-10B: NP—Effect CSCs. NP targets tumor-propagating cell in vitro.
Figure 10B:
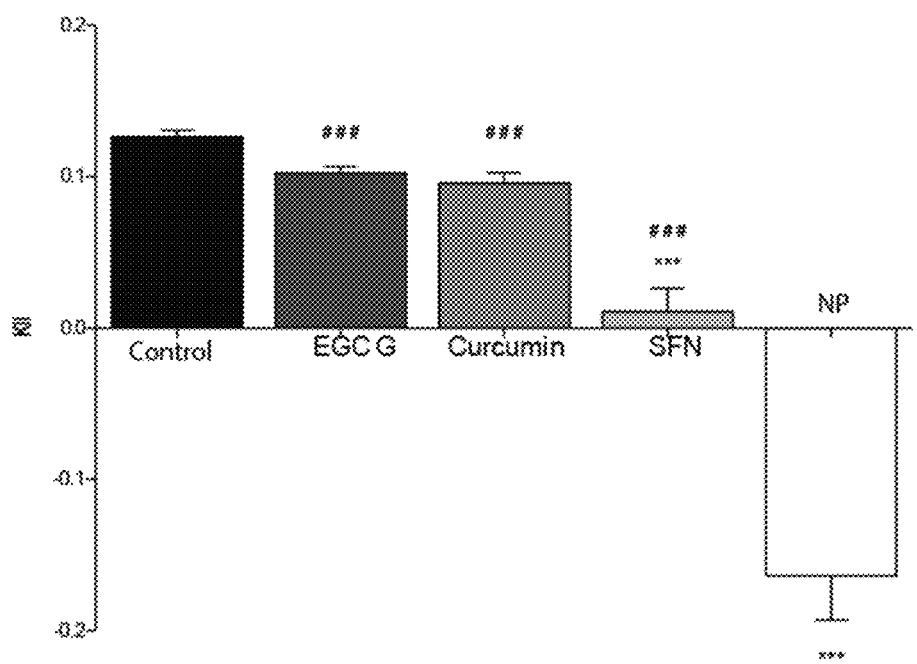
Figure 11:
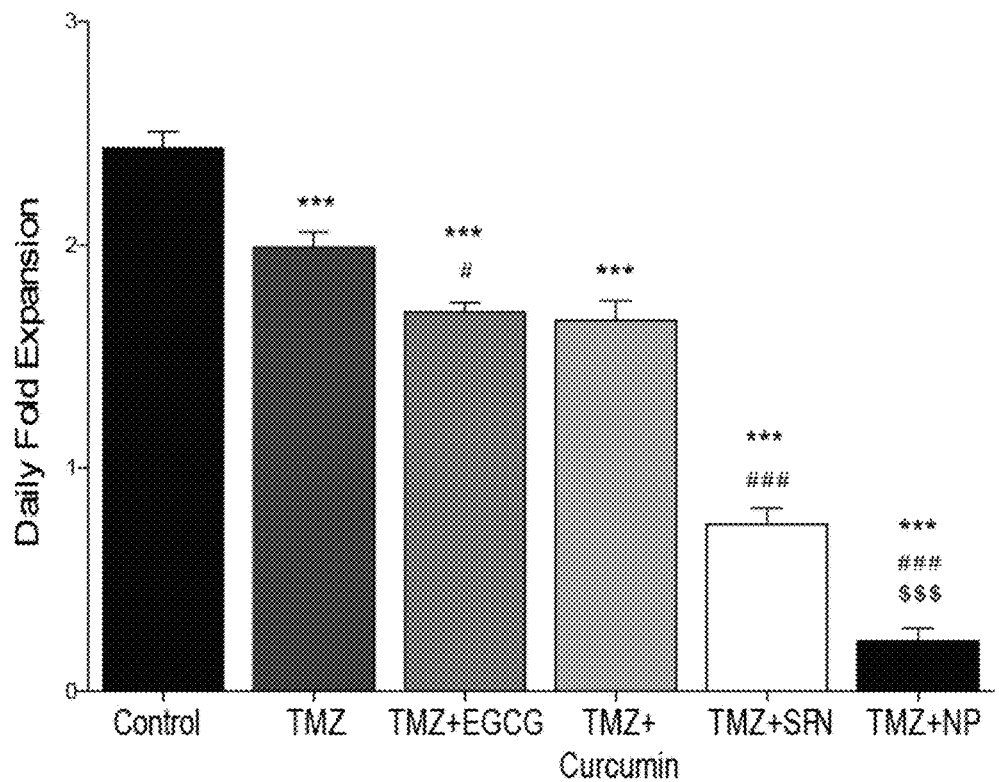
FIG. 11: Daily fold expansion—Effect of NP and TMZ in vitro. Primary human GB stem cell lines were treated daily for 4 out of 5 days in culture TMZ alone or in combination with EGCG (8 µM), Curcumin (0.5 µM), sulforaphane (2.5 µM) or a combination of all three (NP). Cells were passed after 5-7 days and cell counts performed. The addition of EGCG, curcumin or SFN to TMZ treatment resulted in a significant reduction in the mean daily fold expansion of hGB cells compared to control. However, NP had the greatest effect demonstrating synergistic effect. The stars (*) are compared to control, # to TMZ alone and $ to the different combinations of TMZ with each of the individual natural products. 1 symbol, p<0.05, 3 symbols, p<0.001, 1-way ANOVA.

FIG. 10A demonstrates the ability of each NP on its own to reduce the slope of the growth curve compared to the control cultures. The combination of all three NPs produced an unexpected synergistic effect. Applying an algorithm that we have recently developed and published on, the data derived from this serial passage experiment allows us to interrogate and measure the effect of treatment on the cancer stem cell population. When expressed as a Kll value [the probability of a cancer stem cell undergoing a symmetric cell division over a defined period of time] we can see that each of our NPs are able to target the expansion of the cancer stem cells. Strikingly, the combination of our three NPs has a statistically significant effect on reducing symmetric cancer stem cell divisions relative to the control or any of the NPs use on their own [FIG. 10B].

Together these data demonstrate the ability of our NP combination to target and reduce the clonogenic population in a fairly aggressive solid tissue tumor and to be able to reduce the proliferative ability of the clones. It is important to note that the reduced proliferation was observed when the cells were no longer exposed to the NPs [FIG. 9]. This would suggest that a brief exposure to our NPs might have a lasting effect on tumor cell proliferation. In addition, the capability of our NP combination to target the cancer stem cell population is extremely important and relevant as it is this population, which is going to be responsible for therapeutic resistance and recurrence.

Example 6: Natural Products [NPs] Work Synergistically with Conventional Chemotherapy Standard of care [SOC] for many solid tissue cancers involves the use of chemotherapy, which for many advanced or high grade tumors provides marginal benefit. Patient derived hGB cells were grown in culture and treated daily with the conventional drug temozolomide [TMZ, 20 µM] only or in combination with the following NPs:

[1] EGCG-8 µM

[2] Curcumin-0.5 µM

[3] SFN-2.5 µM

[4] a combination of all three NPs

After 5-7 days in culture cells were counted and the mean daily fold expansion calculated. While SOC drug TMZ had a statistically significant effect on reducing the expansion of the tumor cells the addition of EGCG or SFN enhanced this effect, with SFN demonstrating the greatest effect. However, the combination of all three NPs, together with TMZ, had the greatest effect with there being a statistically significant reduction compared to all groups. These results demonstrate that our unique NP combination is capable of enhancing the therapeutic efficacy of SOC TMZ by 8 fold.

Example 7: The Modified Ketogenic Diet [mKD] is Safe, Nutritionally Sufficient and as Effective as the Ketogenic Diet [KD] as a Cancer Treatment NOD-SCID animals were placed on one of the following diets:

[1] Control diet: Is a standard mouse chow and is composed of 55% carbohydrate, 30% protein, 15% fat.

[2] KD: 92% Fat, 3% carbohydrate, 5% protein.

[3] mKD: 10% carbohydrate, 60% Fat (half coming from medium chain triglycerides [MCT, Neobee 598]), 30% Protein.

Figure 12:
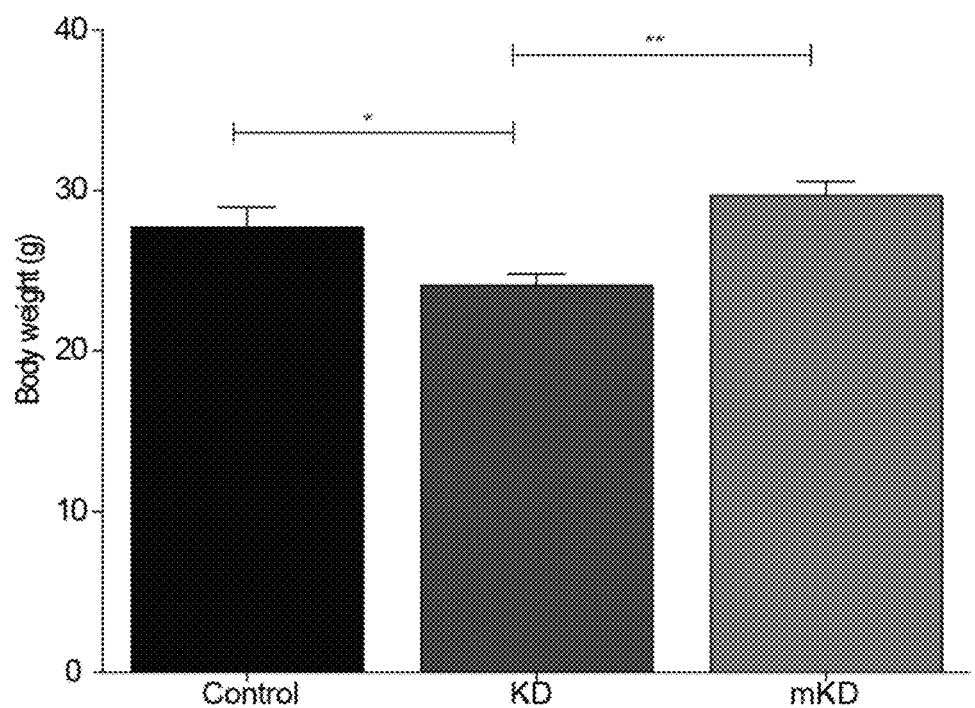
FIG. 12: Effect of mKD on body weight—24 day treatment. Toxicity and nutritional sufficiency of mKD were assessed by monitoring body weight. Animals fed with a KD demonstrated a significant weight loss compared to controls whereas mKD treated group did not show weight loss over the course of 24 days of treatment and exhibited a body weight similar to controls. *, **, p<0.05, p<0.005, 1-way ANOVA.

Body weight was measured 24 days after treatment began and while the KD group exhibited a significant decrease in body weight, the mKD treated animals maintained their body weight relative to the control diet animals [FIG. 12]. This supports the notion that the mKD is nutritionally sufficient to support normal health.

Figure 13:
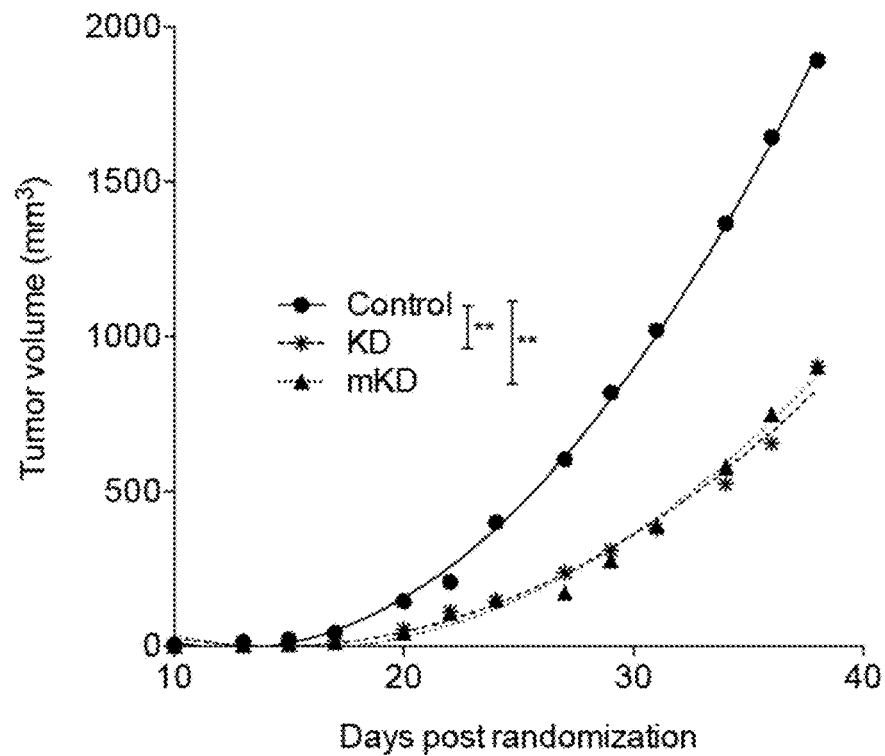
FIG. 13: Effect of mKD on tumor volume progression. NOD/SCID animals were inoculated with 1M hGB cells in the right flank. Tumor dimensions were monitored 3 times per week using calipers and volume was calculated. Treatments were initiated when a palpable mass was identified [approximately 65 mm$^3$]. Animals were sacrificed when they reached endpoint (1700 mm$^3$). Animals treated with KD or mKD showed similar tumor progression and demonstrated a significant slower progression compared to controls (**, p<0.005, two-way ANOVA).
Figure 14:
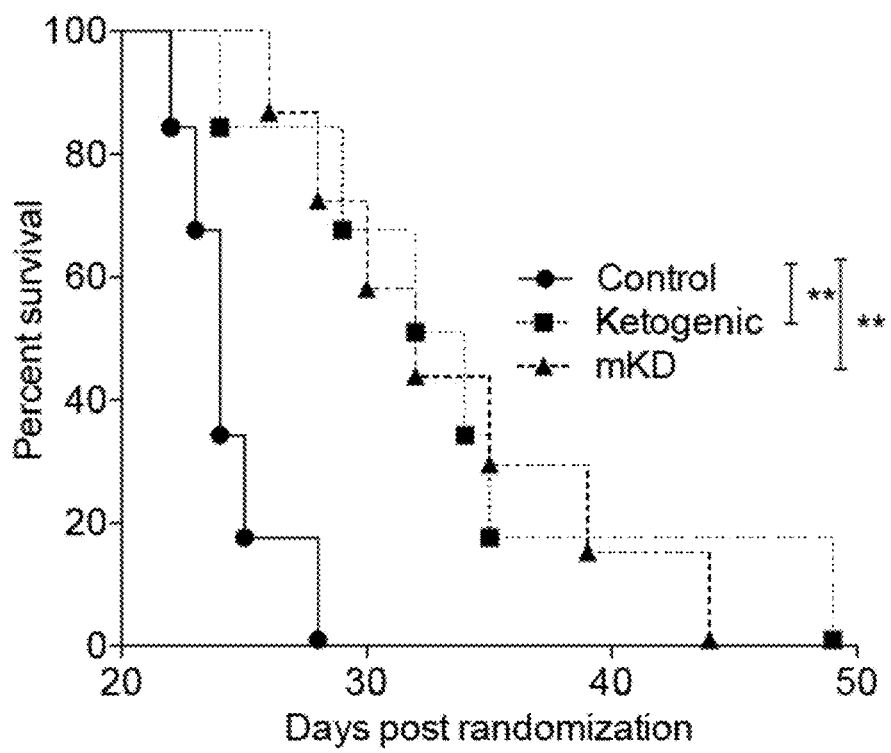
FIG. 14: Effect of mKD on KM curve. NOD/SCID animals were inoculated with 1M hGB cells in the right flank. Tumor dimensions were monitored 3 times per week using calipers and volume was calculated. Treatments were initiated when a palpable mass was identified [approximately 65 mm$^3$]. Animals were sacrificed when they reached endpoint based on a tumor volume of 1700 mm$^3$ calculated from measurements made with a caliper. The fraction of animals living as a function of time is represented using Kaplan-Meier survival curves. Animals treated with KD or mKD showed similar survival and demonstrated a significant improvement over controls (**, p<0.005, Log rank test).
Figure 15:
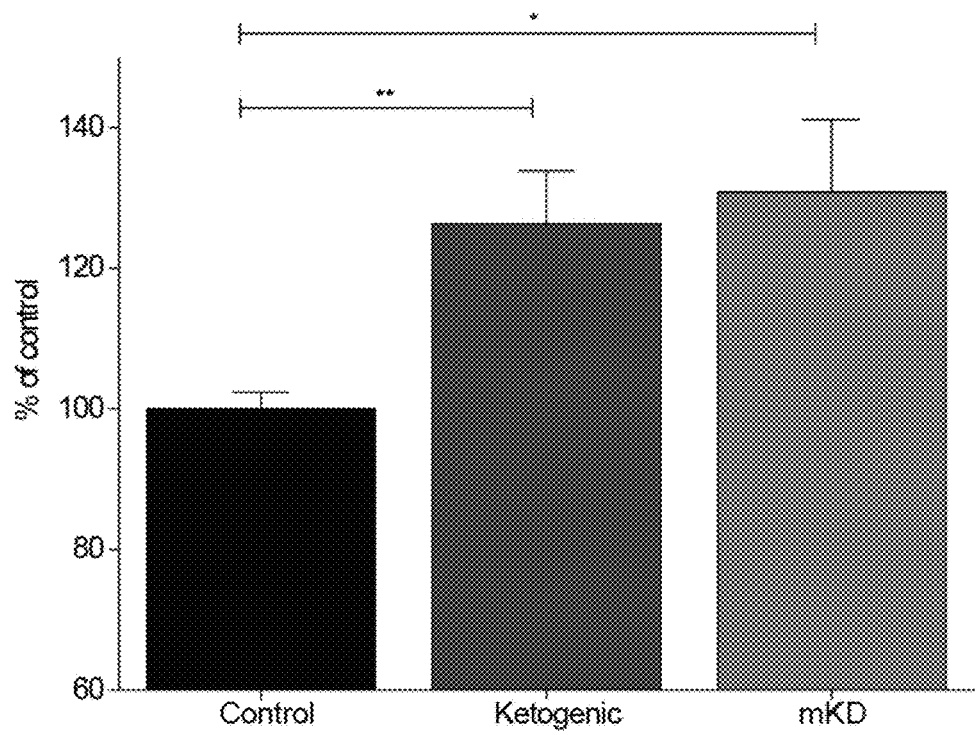
FIG. 15: Effect of mKD progression free survival. NOD/SCID animals were inoculated with 1M hGB cells in the right flank. Tumor volume was calculated 3 times per week and the time from a barely palpable tumor [approximately 65 mm$^3$] to a tumor of a significant size [300 mm$^3$] was calculated. Treatments were initiated when a palpable mass was identified [approximately 65 mm$^3$]. Animals treated with KD or mKD showed similar progression free survival (time during which tumor volume is maintained lower than 300 mm$^3$) and demonstrated a significant improvement over controls (*, **, p<0.05, p<0.005, t-test).
Figure 16:
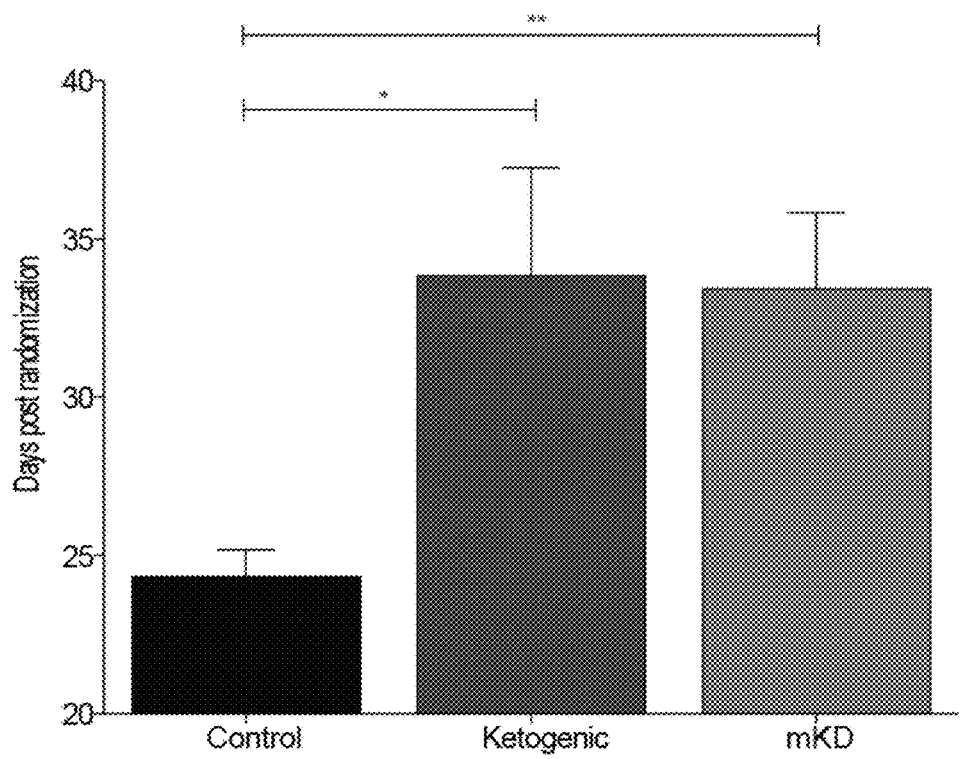
FIG. 16: Effect of mKD on overall survival. NOD/SCID animals were inoculated with 1M hGB cells in the right flank. Tumor dimensions were monitored 3 times per week using calipers and volume was calculated. Treatments were initiated when a palpable mass was identified [approximately 65 mm$^3$]. Animals were sacrificed when they reached endpoint (1700 mm$^3$). The average time to reach endpoint volume was then compared. Animals treated with KD or mKD showed similar overall survival and demonstrated a significant improvement over controls (**, p<0.005, Log rank test).

Following inoculation of 1M GB tumor cells into the right flank of NOD-SCID mice animals were randomized and put on one of the three diets. Tumor progression was followed by recording 2 measurements of tumor diameter and converting this into a volume using the following formula: $(4/3)\pi R^3$. For spheroid tumors the two measurements were averaged to determine the diameter of the sphere. In the case of ellipsoid tumors (i.e. prolate or oblate spheroid mass) the formula used was: $(4/3)\pi*(d/2)*(d/2)2$. In this case the second measurement "d2" would count twice and "d" only once. For prolate spheroids, the long measurement occurs once while the short measurement occurs twice. Conversely, for the oblate spheroid tumors, the long measurement occurs twice while the short one occurs only once. Following this criteria, tumor volume was tracked over time. FIG. 13 illustrates that the KD and mKD resulting in a significant delay in tumor progression compared to the control group. No difference was seen between the KD and mKD fed animals. Overall survival was analyzed using Kaplan-Meier survival curve [GraphPad], and both the mKD and KD feed animals lived significantly longer than controls [FIG. 14]. Similar to tumor progression, there was no significant difference between the mKD and KD groups. Lastly, we compared the time to tumor progression [defined as the time it took for a palpable tumor to reach a size that was visible—300 mm3], in this case there were a statistically significant reduction in the time to tumor progression in both the KD and mKD group [FIG. 15]. No difference was seen between the KD and mKD feed animals. FIG. 16 depicts the mean survival of our three treatment groups. Mean survival was significantly enhanced in both the KD and mKD fed animals, with no differences seen between these two groups.

Overall, these data support our conclusion that our mKD is nutritionally sufficient with no adverse effects on overall health and like the KD is an effective cancer treatment that delays tumor progression and enhances overall survival.

Example 8: Combining the mKD and NPs Enhances the Therapeutic Effect on GB Cell Proliferation and Targeting of the Cancer Stem Cell Population In Vitro Patient derived hGB cell lines were exposed to either the mKD, NPs or both for 5-7 days in culture after which total cell number was determined and compared to control cultures. The mKD was mimicked in vitro by reducing glucose levels to those found in patients who are on a KD [65-80 mg/dl] and elevating ketones to 4 mM [hydroxybutyrate, Sigma]. The three natural products that were added were:

[1] EGCG-8 µM

[2] Curcumin-0.5 µM

[3] SFN-2.5 µM

Figure 17:
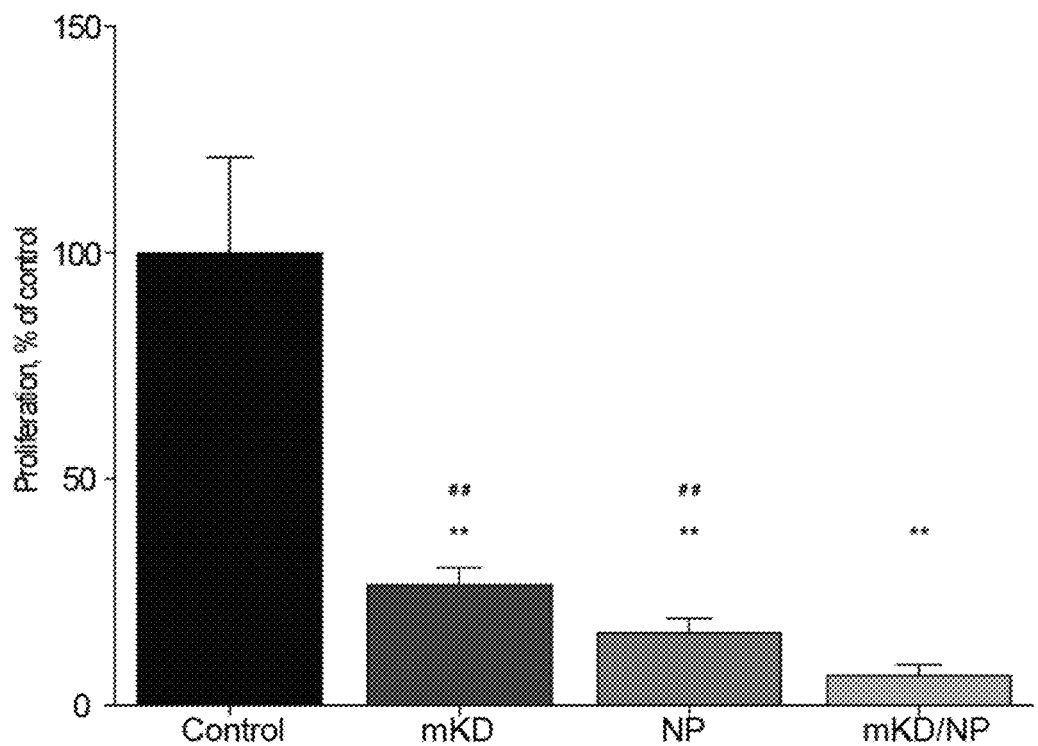
FIG. 17: Effect of mKD/NP on proliferation (In vitro). Human GB cells were plated at 50,000 cells per ml in the neurosphere assay. The cells were treated with the indicated treatments and harvested for cell number quantification after 7 days of culture. The three treatment groups demonstrated significant decrease of proliferation compared to control, with mKD/NP treated animals showing significant difference compared to mKD and NP groups. **, compared to control, ## compared to mKD/NP, p<0.001, t-test. Details of the treatments: [1] mKD=4 mM ketones [Beta Hydroxybutyrate] (Single treatment applied 2 days post plating), [2] NP=EGCG [8 µM]+SFN [2.5 µM]+Curcumin [0.5 µM]: daily treatment from day 3 to day 6, [3] mKD/NP=4 mM ketones+EGCG [8 µM]+SFN [5 µM]+Curcumin [0.5 µM]. Of note, glucose level was 65 mg/dL in the mKD and mKD/NP groups, and 130 mg/dL in the control and NP groups.
Figure 18:
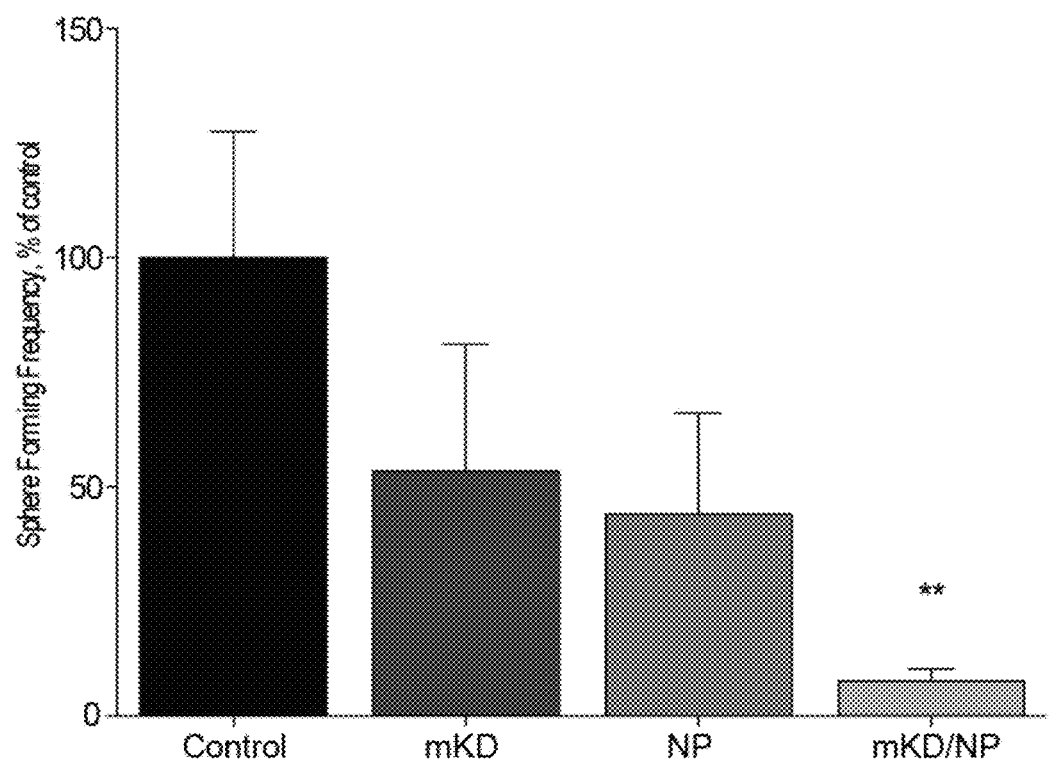
FIG. 18: Effect of mKD/NP on CSC. Sphere forming frequency was measured to evaluate the effect of the different treatments on the proliferation of CSCs. Human GB cells were plated at 50,000 cells per ml in the neurosphere assay. The cells were treated with the indicated treatments and harvested to be plated in regular medium (no treatment) at clonal density for comparison of their respective sphere formation ability. mKD/NP treated cells showed significant decrease of sphere forming ability compared to the control group. **, p<0.005, t-test.

Under these conditions there was a significant reduction in the number of cells that were generated over the 5-7 day in both the mKD and NP treated cultures. The most significant reduction however was seen when the mKD was used together with NPs [FIG. 17]. In a separate experiment we examined the effects of each treatment [mKD, NPs, and combination] on the number of proliferating or clonogenic cells. Cultured hGB cells were treated with one of our three treatment conditions for seven days in vitro, after which cultures were washed, dissociated into a single cell suspension and we plated in control medium so as to assess the effects of treatment on the number of sphere forming cells [or clonogenic frequency]. The number of spheres was enumerated 7 to 10 days later. FIG. 18 demonstrates that while the mKD and the NPs treatments resulted in an approximate 50% reduction in the number of sphere forming cells [which was not significant due to a high variability] there was a statistically significant reduction in the mKD/NP treated cultures [90%].

Figure 19:
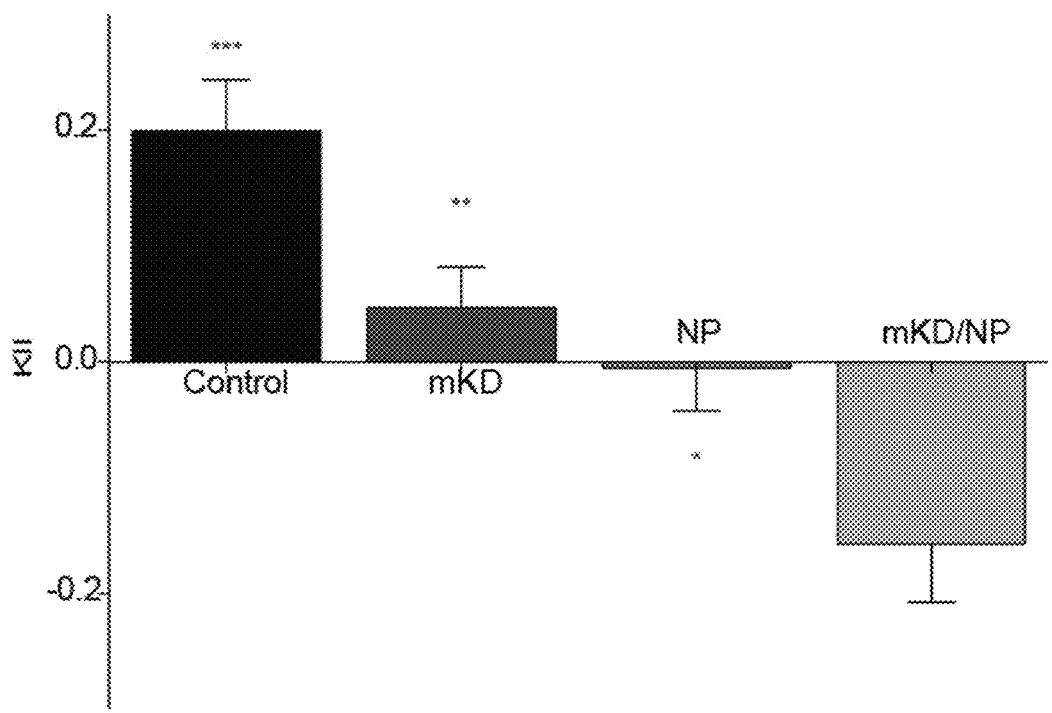
FIG. 19: Effect of mKD/NP on CSC expansion. The rate of cancer stem cell (CSC) expansion (Kll) is directly correlated to the probability CSCs undergo self-renewing symmetric division and can be calculated by taking the natural logarithm of the fold expansion and dividing by the passage time (Deleyrolle et al., 2011). Human GB cells were cultured in the neurosphere assay over 4 passages during which CSC expansion rate was evaluated. The three treatment groups demonstrated significant decrease of CSCs self-renewing symmetric division rate compared to control. mKD/NP group also demonstrated significant decrease compared to mKD and NP groups. *, , *, p<0.05, p<0.01, p<0.001, compared to mKD/NP, t-test.

Cancer stem cells are thought to contribute to therapy resistance and be responsible for driving long term tumor growth, targeting this population is widely believed to be essential for the development of successful cancer therapeutics. Using a previously published algorithm that is able to enumerate symmetric cancer stem cell divisions, data was collected by serially passage of patient derived hGB cells in one of our four treatment conditions [control, mKD, NP or mKD/NP]. Our data indicates that each of the treatment conditions resulted in a significant reduction in the frequency of symmetric cancer stem cell divisions relative to the control. The greatest effect was seen in the combination treatment of mKD/NP [FIG. 19].

Together the experiments in this example demonstrate that the combination of a mKD and our NPs exhibit the greatest effect at reducing overall proliferation, reducing the number of proliferating clonogenic cells and targeting the cancer stem cell population by reducing the number of symmetric stem cell divisions within this important subpopulation of GB tumor cells.

Example 9: Combining mKD and NPs Reduces Tumor Progression, Increases Overall Survival Compared to mKD or NPs Alone NOD-SCID animals were inoculated with 1M patient derived hGB cells. Once a palpable tumor was identified [2 to 4 weeks later], animals were randomized into 1 of 4 groups:

[1] Control diet: Is a standard mouse chow and is composed of 55% carbohydrate, 30% protein, 15% fat.

[2] mKD: 10% carbohydrate, 60% Fat (half coming from medium chain triglycerides [MCT, Neobee 598]), 30% Protein.

[3] NP diet: 55% carbohydrate, 30% protein, 15% fat+ SFN (25 mg/kg; BSP95%/DRSP5%), Curcumin (1200 mg/kg), EGCG (1200 mg/kg).

[4] mKD/NP: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg).

Figure 20:
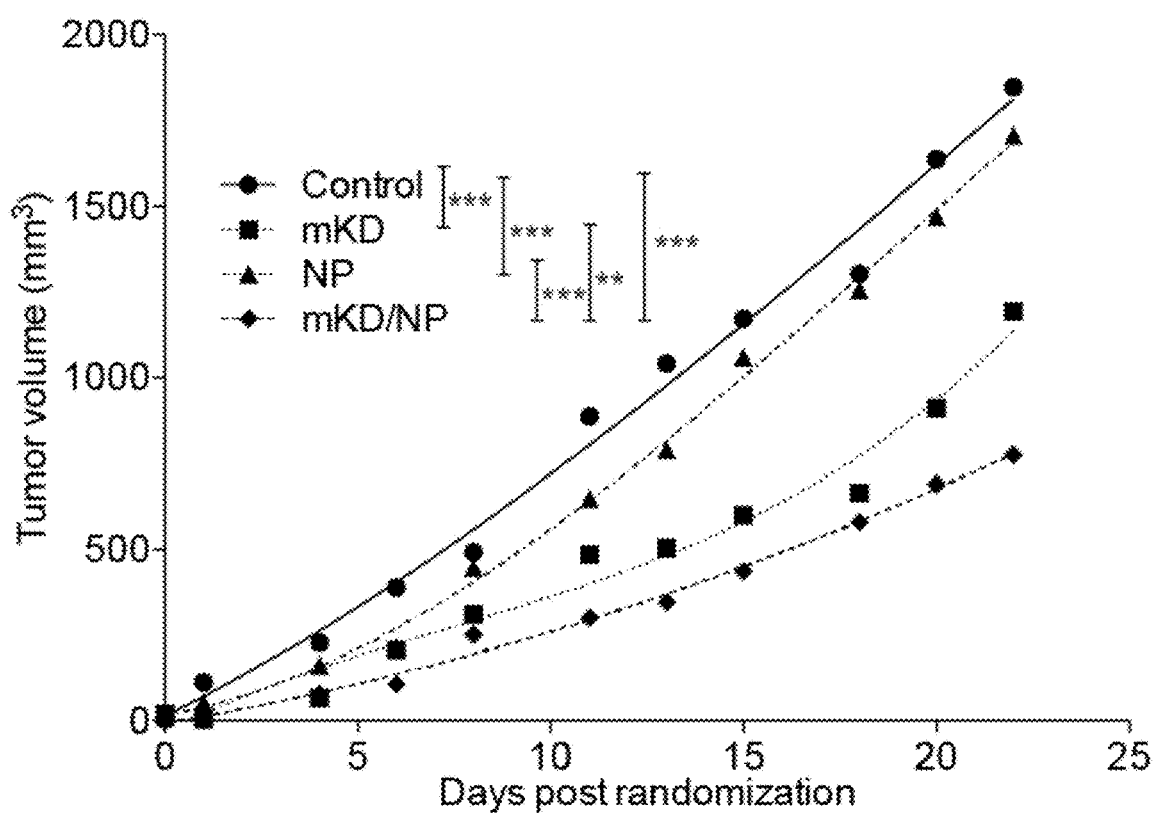
FIG. 20: Effect of mKD/NP on Tumor Progression. NOD/SCID animals were inoculated with 1M hGB cells in the right flank. Tumor dimensions were monitored 3 times per week using calipers and volume was calculated. Treatments were initiated when a palpable mass was identified [approximately 65 mm$^3$]. Animals were sacrificed when they reached endpoint (1500 mm$^3$). Animals treated with mKD/NP demonstrated a significant slower tumor progression compared to controls or animals treated with mKD or NP (, *p<0.01, p<0.002, two-way ANOVA). These results demonstrate a synergistic effect in vivo between mKD and NP.
Figure 21:
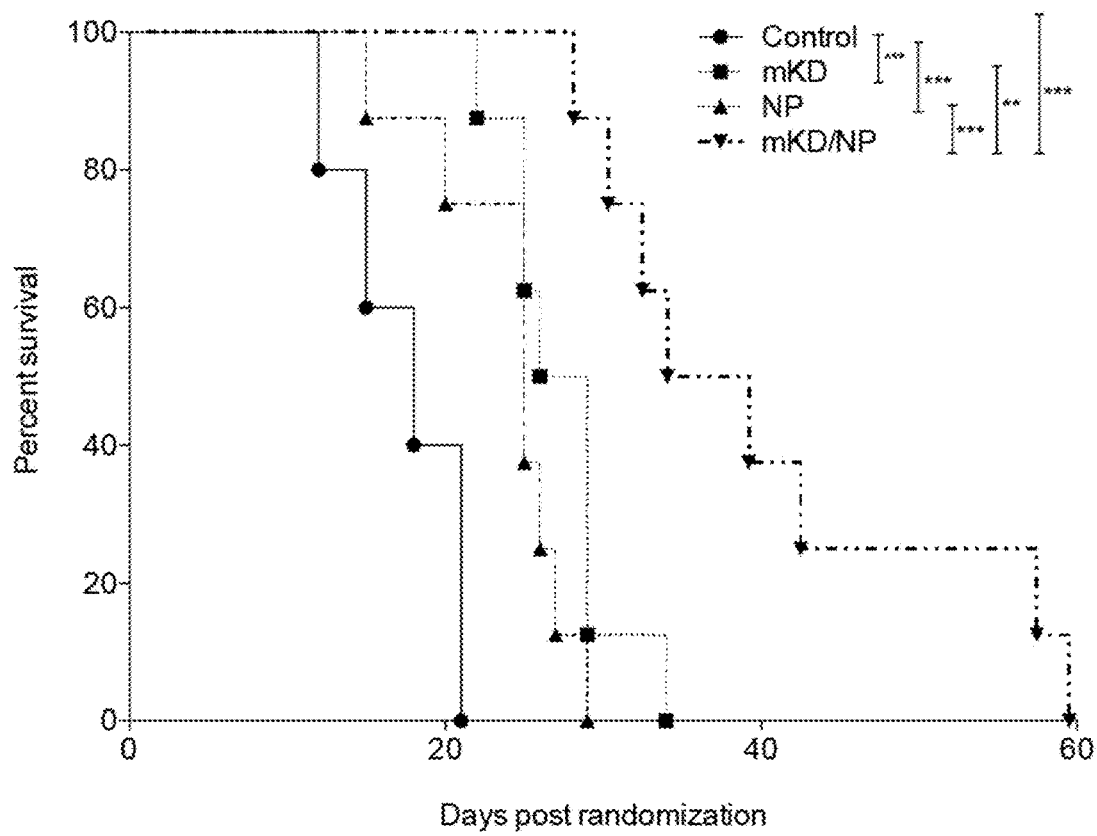
FIG. 21: Effect of mKD/NP on KM curve. NOD/SCID animals were inoculated with 1M hGB cells in the right flank. Tumor volume was monitored 3 times per week. Treatments were initiated when a palpable mass was identified [approximately 65 mm$^3$]. Animals were sacrificed when they reached endpoint (1500 mm$^3$). The fraction of animals living as a function of time is represented using Kaplan-Meier survival curves. Animals treated with mKD/NP demonstrated a significant improvement over controls or animals treated with mKD or NP (, *p<0.01, p<0.002, Log rank test).
Figure 22:
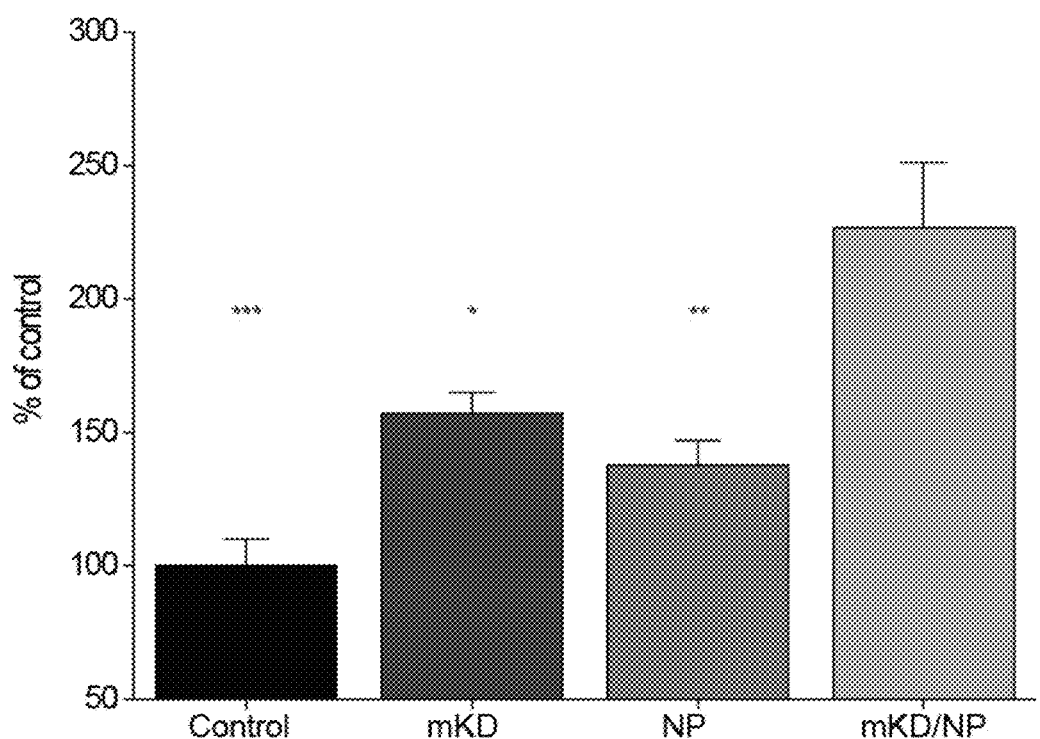
FIG. 22: Effect of mKD/NP on overall survival. NOD/SCID animals were inoculated with 1M hGB cells in the right flank. Tumor volume was monitored 3 times per week. Treatments were initiated when a palpable mass was identified [approximately 65 mm$^3$]. Animals were sacrificed when they reached endpoint (1500 mm$^3$). The average time to reach endpoint volume was then compared. Animals treated with mKD/NP demonstrated a significant increase of overall survival compared to controls or animals treated with mKD or NP (*, , *p<0.05, p<0.01, p<0.002, compared to mKD/NP, t-test).
Figure 23:
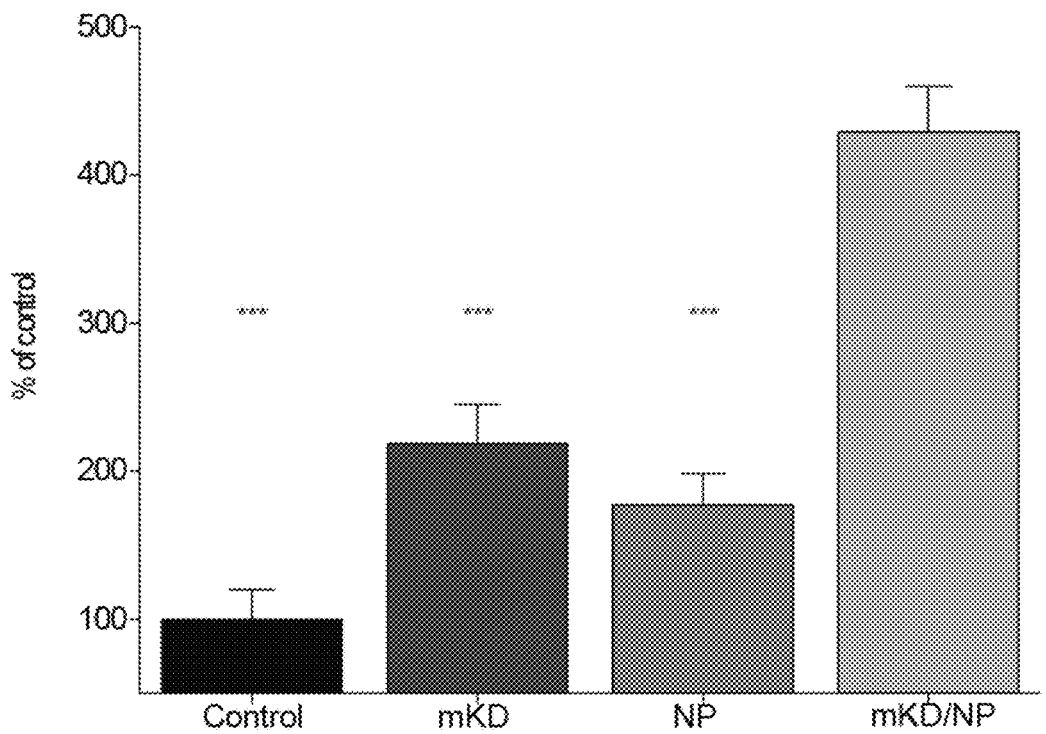
FIG. 23: Effect of mKD/NP on Progression Free Survival. NOD/SCID animals were inoculated with 1M hGB cells in the right flank. Tumor volume was calculated 3 times per week and the time from a barely palpable tumor [approximately 65 mm$^3$] to a tumor of a significant size [300 mm$^3$] was calculated. Treatments were initiated when a palpable mass was identified [approximately 65 mm$^3$]. mKD/NP animals demonstrated a significant increase of tumor progression free survival (time during which tumor volume is maintained lower than 300 mm$^3$) compared to controls or animals treated with mKD or NP (***, p<0.0001, compared to mKD/NP, 1-way ANOVA). These results suggest a synergistic effect between mKD and NP treatments.

Tumor were measured 3 times per week, volume calculated and progression tracked, presented and statistical comparison made in GraphPad [using non-linear regression, 2-way ANOVA]. FIG. 20 illustrates tumor progression for these four treatment groups and demonstrates a significant reduction in tumor progression for all treatment groups relative to control. The combination of mKD/NP demonstrated the most significant reduction compared to any of the treatment groups. When animals reached the endpoint, [tumors greater than 1500 mm3], they were killed and Kaplan-Meier plot was used to analyze survival [GraphPad]. FIG. 21 reveals that all treatment groups survived significantly longer than the controls, with the mKD/NP treated animals demonstrating statistically significant increase in survival compared to mKD and NP treated animals. The mean survival is depicted in FIG. 22 and further demonstrates the superiority of mKD/NP in increasing survival. The combination of the two treatments also resulted in a statistically significant increase in progression free survival as determined by the time it took a palpable tumor to reach a volume of 300 mm$^3$ [FIG. 23].

Together these data demonstrate the advantage of combining two novel and effective therapeutic protocols [mKD and NPs] to produce an unexpected synergistic effect delaying tumor progression and increasing mean and maximum lifespan.

Example 10: The mKD/NP Diet Increases Lifespan in an Orthotopic Xenograft Model of GB NOD-SCID mice received an intracranial injection of 200K hGB cells into the right striatum. Three days after initial surgery animals were randomized into one of two groups:

[1] Control diet: Is a standard mouse chow and is composed of 55% carbohydrate, 30% protein, 15% fat.

[2] mKD/NP: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg).

Figure 24:
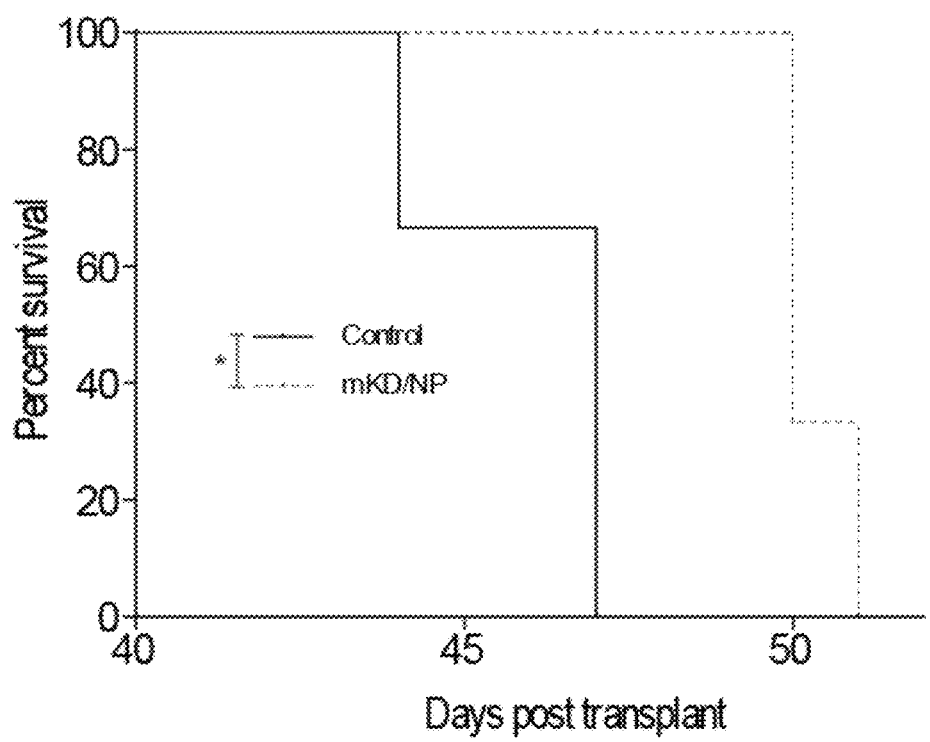
FIG. 24: Effect of mKD/NP on KM after intracranial inoculation of hGB cells. NOD/SCID animals were inoculated with 200K hGB cells in the striatum. Treatments were initiated 3 days post implant. Animals were sacrificed when they reached endpoint marked by the development of neurologic signs (including, but not limited to, lethargy, paralysis, or seizure). The fraction of animals living as a function of time is represented using Kaplan-Meier survival curves. mKD/NP treated animals demonstrated a significant increased survival compared to control animals (*, p=0.014, Log-Rank test).
Figure 25:
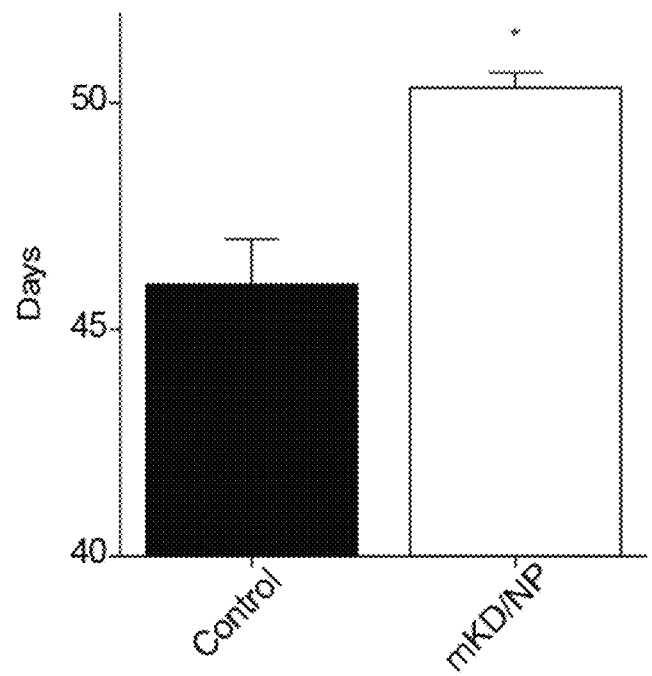
FIG. 25: Effect of mKD/NP on overall survival after intracranial inoculation of hGB cells. NOD/SCID animals were inoculated with 200K hGB cells in the striatum. Treatments were initiated 3 days post implant. Animals were sacrificed when they reached endpoint marked by the development of neurologic signs (including, but not limited to, lethargy, paralysis, or seizure). The average time to reach endpoint volume (i.e. overall survival time) was then compared. mKD/NP treated animals demonstrated a significant increased overall survival compared to controls (*, p<0.05, t-test).

Animals were closely monitored for any signs of disease or distress and when they began to exhibit abnormal neurological signs [lethargy, paralysis, seizure or abnormal motor behavior] animals were killed. Kaplan-Meier plots indicate that the mKD/NP group survived significantly longer than the control fed animals [FIG. 24]. The mean survival was calculated for both groups and FIG. 25 reveals a significant increase in mean survival for the mKD/NP fed animals.

These data strongly support the efficacy of using our combination mKD/NP treatment in an orthotopic xenograft cancer model.

Example 11: mKD/NP Treatment Performs as Well as Standard of Care Chemotherapy for GB The standard of care [SOC] for patients with high-grade gliomas such as GB involves the use of the chemotherapy drug Temozolomide [TMZ]. While TMZ demonstrates some degree of effectiveness for GB patients, the increase in survival is marginal [about 2-3 months] and the negative side effects are significant [nausea, vomiting and hematological toxicity]. Hence, there exists a need for less toxic but effective treatments. NOD-SCID animals were inoculated with 1M patient derived hGB cells. Once a palpable tumor was identified [approximately 2-3 weeks post implant], animals were randomized into 1 of 3 groups:

[1] Control diet: Is a standard mouse chow and is composed of 55% carbohydrate, 30% protein, 15% fat.

[2] Standard of Care: Control diet together with daily TMZ injections [5 mg/kg].

[3] mKD/NP: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg).

Figure 26:
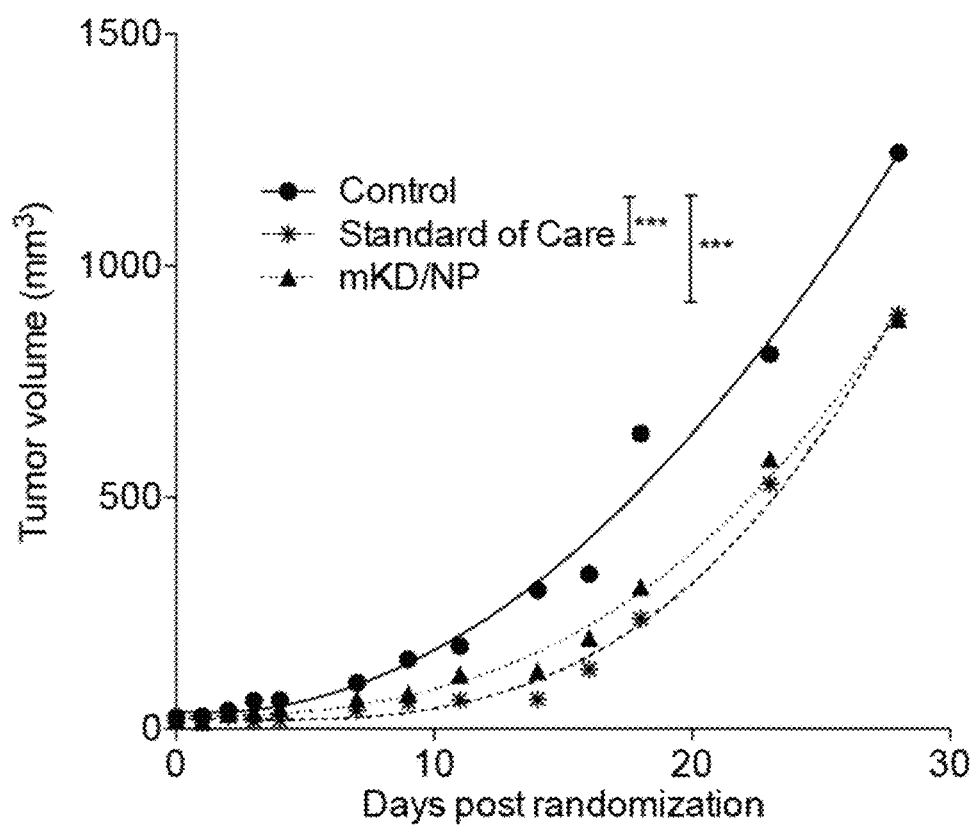
FIG. 26: Tumor Progression—TMZ vs. mKD/NP. NOD/SCID animals were inoculated with 1M hGB cells in the right flank. Tumor volume was monitored 3 times per week using a caliper and tumor volume was calculated. Treatments were initiated when a palpable mass was identified [approximately 65 mm$^3$]. Animals were sacrificed when they reached endpoint (1500 mm$^3$). Animals treated with standard of care (temozolomide, TMZ, 5 mg/kg) or mKD/NP demonstrated a similar and significant slower tumor progression compared to controls (***, p<0.0001, two-way ANOVA).
Figure 27:
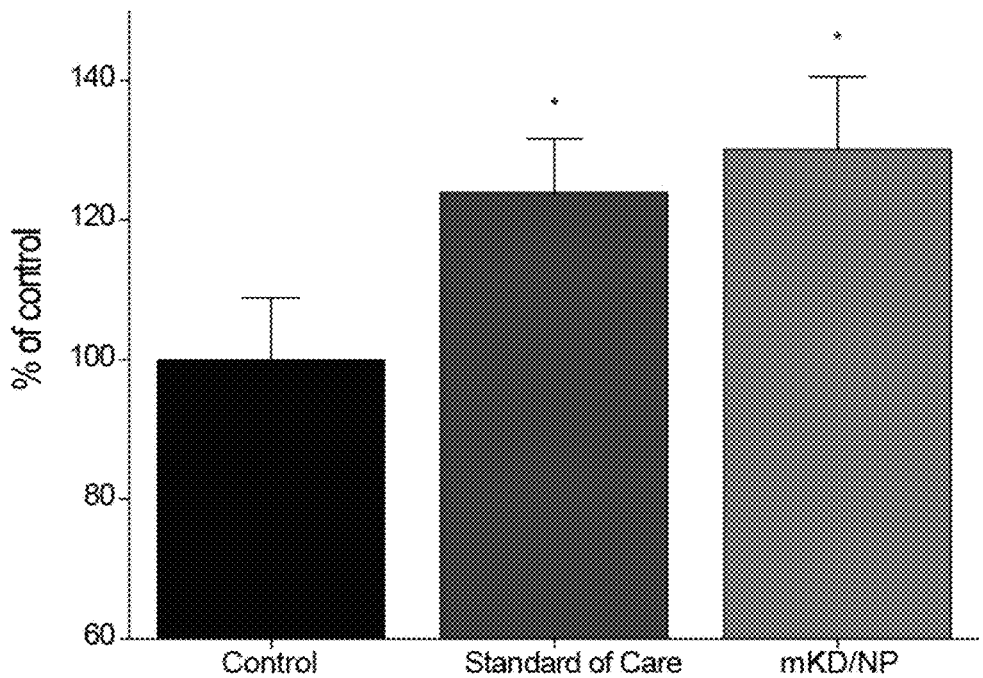
FIG. 27: Progression Free Survival—TMZ vs. mKD/NP. NOD/SCID animals were inoculated with 1M hGB cells in the right flank. Tumor volume was calculated 3 times per week and the time from a barely palpable tumor [approximately 65 mm$^3$] to a tumor of a significant size [300 mm$^3$] was calculated. Treatments were initiated when a palpable mass was identified [approximately 65 mm$^3$]. Animals treated with standard of care (temozolomide, TMZ, 5 mg/kg) or mKD/NP demonstrated a similar and significant increase of progression free survival time (time during which tumor volume is maintained lower than 300 mm$^3$) compared to controls (*p<0.05, t-test).

Tumors were measured 3 times per week, volume calculated and progression tracked, presented and statistical comparison made in GraphPad [using non-linear regression, two-way ANOVA]. FIG. 26 demonstrates that the mKD/NP diet is able to reduce tumor progression to the same extent as SOC. Relative to the control animals both SOC and mKD/NP resulted in a significant increase in progression free survival as measured by the time they took a palpable tumor to reach 300 mm3 [FIG. 27].

Together these data indicate that the mKD/NP therapeutic is as effective as SOC chemotherapy in delaying tumor progression and enhancing progression free survival.

Example 12: mKD/NP is an Effective Adjunct Treatment when Used Together with Standard of Care for GB NOD-SCID animals received an injection of 1M patient derived hGB cells into the right flank. Once a palpable tumor was identified animals were randomized into 1 of 4 treatment groups:

[1] Control diet: Is a standard mouse chow and is composed of 55% carbohydrate, 30% protein, 15% fat.

[2] Standard of Care: Control diet together with daily TMZ injections [5 mg/kg].

[3] mKD/NP: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg).

[4] SOC+mKD/NP: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg), together with daily TMZ injections [5 mg/kg].

Figure 28:
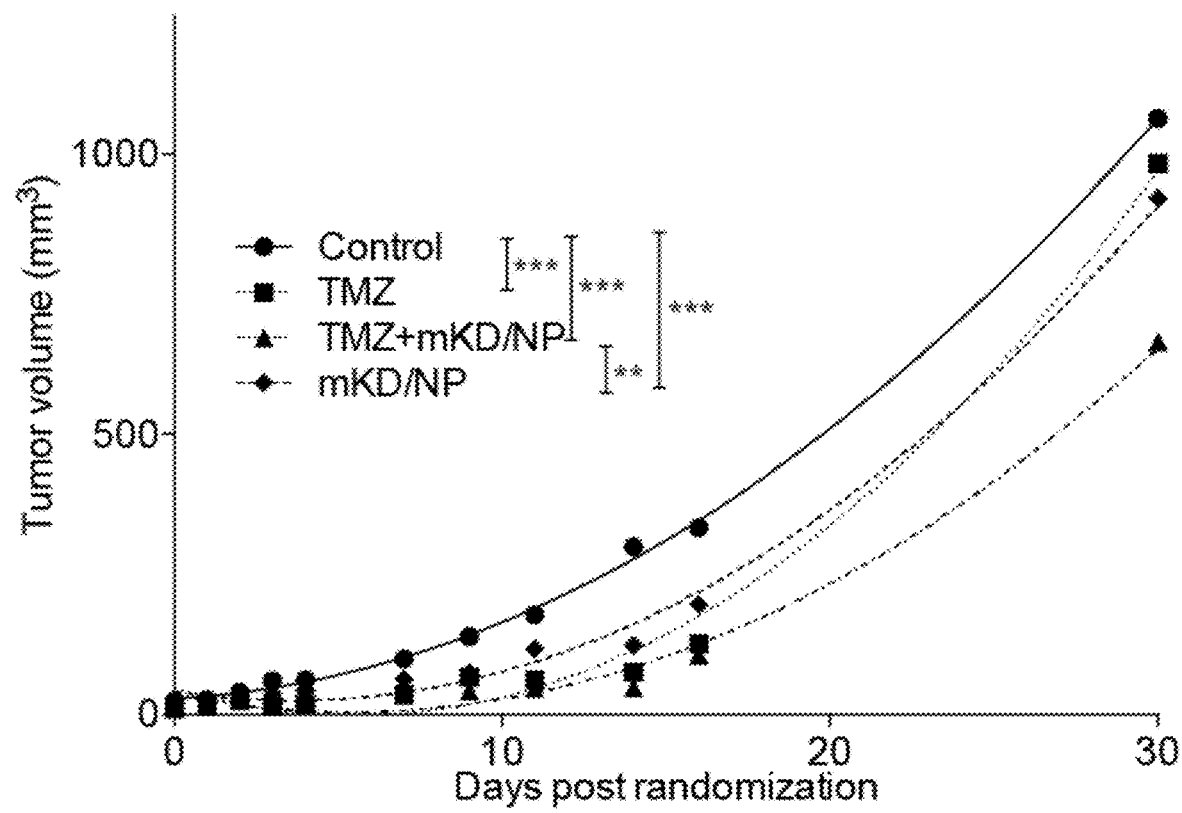
FIG. 28: mKD/NP—Adjuvant Tumor Progression. NOD/SCID animals were inoculated with 1M TMZ sensitive hGB cells in the right flank. Tumor volume was monitored 3 times per week using a caliper and tumor volume was calculated. Treatments were initiated when a palpable mass was identified [approximately 65 mm$^3$]. Animals treated with standard of care (temozolomide, TMZ, 5 mg/kg) or mKD/NP demonstrated a similar and significant slower tumor progression compared to controls. The combination of standard of care with mKD/NP showed a significant decrease of tumor progression compared to controls and mKD/NP treated group. , *, p<0.005, p<0.0001, two-way ANOVA.

Tumor volume was measured 3 times per week, recorded and analyzed using GraphPad software. FIG. 28 depicts tumor growth over time and indicates that mKD/NP performs as well as SOC; however, the combination of mKD/

NP together with SOC demonstrates a further reduction in tumor progression. When TMZ-resistant hGB cells were used as the donor cells implanted into the NOD-SCID mice, SOC had no effect on tumor progression. However, mKD/NP was an effective treatment that was enhanced by combining mKD/NP and SOC [FIG. 29].

In summary, the experiments in this example demonstrate the efficiency of mKD/NP treatment and that the efficacy can be enhanced by combining with SOC. Unexpectedly, SOC resistant tumors are not only responsive to mKD/NP but addition of mKD/NP with TMZ sensitizes the tumor cells to previous ineffective SOC therapy. As virtually all patients with stage IV cancers will develop resistance to their SOC chemotherapy, the ability to sensitize the tumor to SOC therapy with a safe and low toxicity adjunct treatment is of tremendous value for the cancer care community.

Example 13: mKD/NP as a Preventative Treatment

There are currently nearly 14 million people living with cancer in the USA alone, a number that is expected to rise to 18M in the next 10 years. Developing treatments that prevent or delay initial development of cancer or recurrence will have a significant effect on not only the personal impact of the cancer but a tremendous economic influence as well.

Towards this end we have tested the ability of the mKD/NP treatment as a preventive treatment and to delay tumor onset.

NOD-SCID animals were placed on one of two diets:
[1] Control diet: Is a standard mouse chow and is composed of 55% carbohydrate, 30% protein, 15% fat.
[2] mKD/NP: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg).

Figure 30:
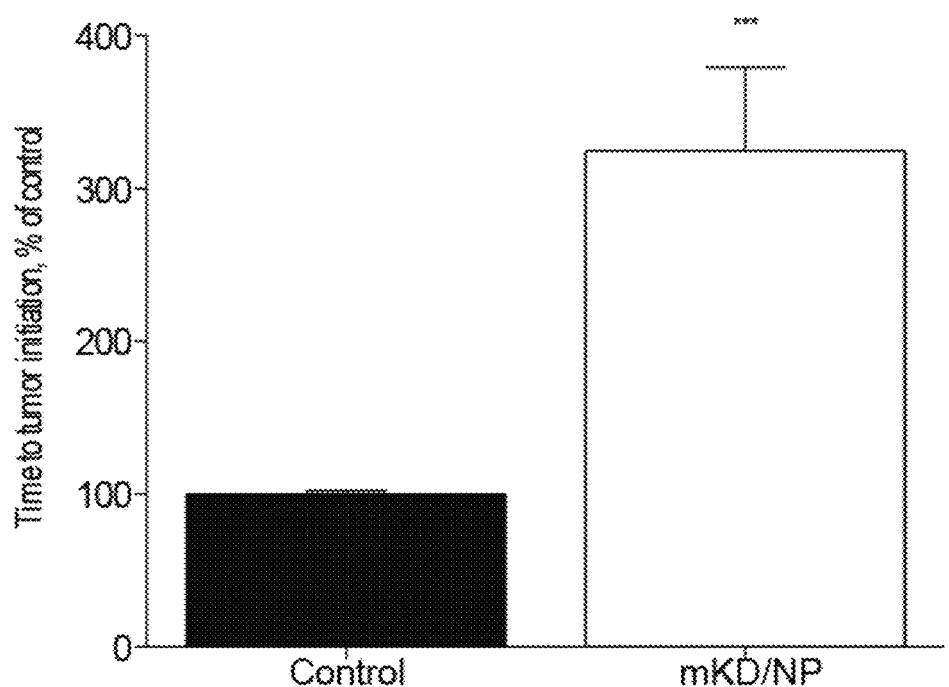
FIG. 30: Effect of mKD/NP on time to tumor initiation—GB. Animals were placed on mKD/NP for 2 months prior to sub-Q tumor implantation. After 2 months of treatment the NOD/SCID animals were inoculated with 1M hGB cells in the right flank. Tumor growth was then monitored 3 times per week to determine the time between tumor cell implantation and the time a tumor could be palpable (i.e. reaching a volume approximating 65 mm$^3$). The graph depicts the average time between implant and positive palpation. The mKD/NP treated group demonstrated a time to tumor initiation approximately 3 times greater than in the controls (***, p<0.01, t-test).
Figure 31:
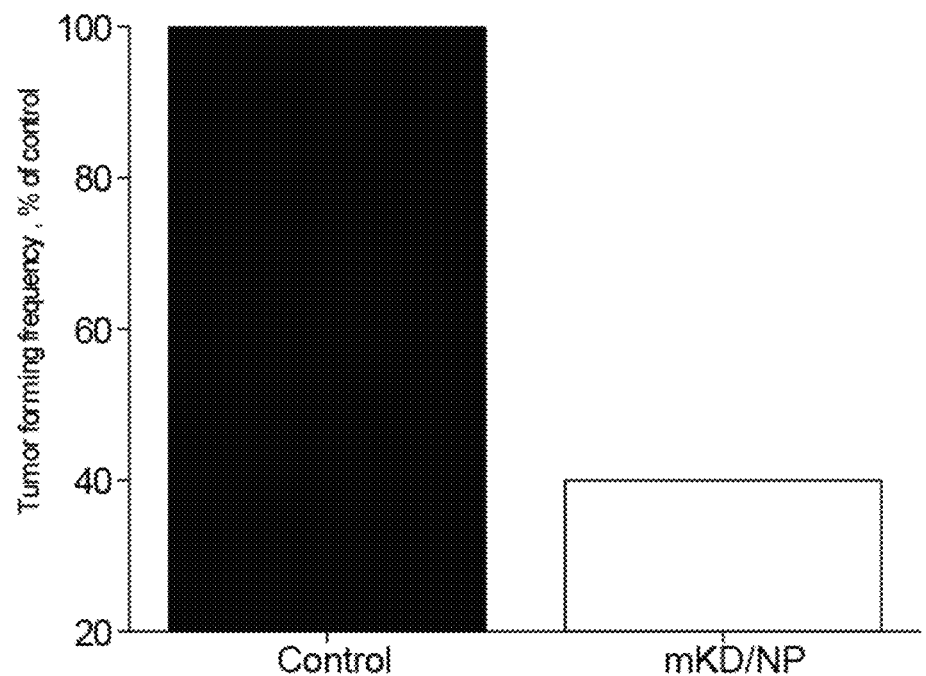
FIG. 31: Effect of mKD/NP on tumor forming frequency—GB. Animals were placed on mKD/NP for 2 months prior to sub-Q tumor implantation. After 2 months of treatment the NOD/SCID animals were inoculated with 1M hGB cells in the right flank. Tumor growth was then monitored 3 times per week to determine the time between tumor cell implantation and the time a tumor could be palpable (i.e. reaching a volume approximating 65 mm$^3$). The percentage of animals that had developed tumor was recorded. mKD/NP pre-treated group showed a 60% decrease in tumor initiation compared to controls.

After being on the diets for two months animals received a subcutaneous injection of 1M patient derived hGB cells into the right flank. Animals were monitored daily for the initial appearance of a palpable tumor [approximately 65 mm³]. FIG. 30 indicates that animals on the mKD/NP diet had a significant delay in the time to first appearance of a tumor [approximately 300%]. Of greater interest was the 60% reduction in the numbers of animals that developed tumors [FIG. 31].

Figure 32:
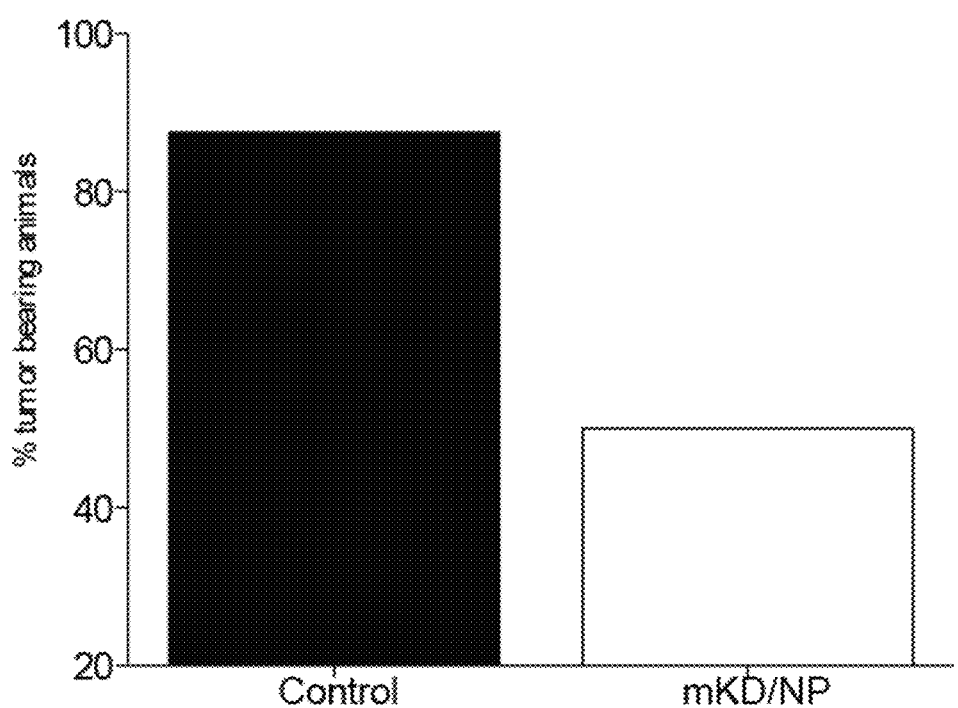
FIG. 32: Effect of mKD/NP on tumor forming frequency—Lung Cancer. NOD/SCID animals were treated for 2 weeks with control diet or mKD/NP before to be inoculated with 2M of lung carcinoma cells (A549) in the right flank. Tumor growth was then monitored 3 times per week. 21 days after implant almost 90% of the control animals developed tumor whereas only 50% of the animals treated with mKD/NP showed tumor formation.

Using a similar paradigm, animals were placed on the control or mKD/NP diet for two weeks prior to being inoculated with 2M lung carcinoma cells [A549] in the right flank of NOD-SCID animals. 21 days after tumor implantation approximately 90% of the control animals had developed a palpable tumor, in contrast, only 50% of the animals on the mKD/NP diet had a palpable tumor [FIG. 32].

Together these data demonstrate the efficacy of the mKD/NP diet in not only delaying the onset of a discernible tumor but also its ability to reduce the occurrence of tumor and hence have a preventive effect.

Example 14: mKD/NP Attenuates the Effects of a Peripheral Tumor on Central Nervous System Stem Cell Proliferation and NP is Able to Enhance In Vitro the Pool of Neural Stem Cells NOD-SCID animals were inoculated with 1M cells in the right flank. Once a discernible tumor was palpated, animals were randomized into one of two groups:
[1] Control diet: Is a standard mouse chow and is composed of 55% carbohydrate, 30% protein, 15% fat.
[2] mKD/NP: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg).

Figure 33A:
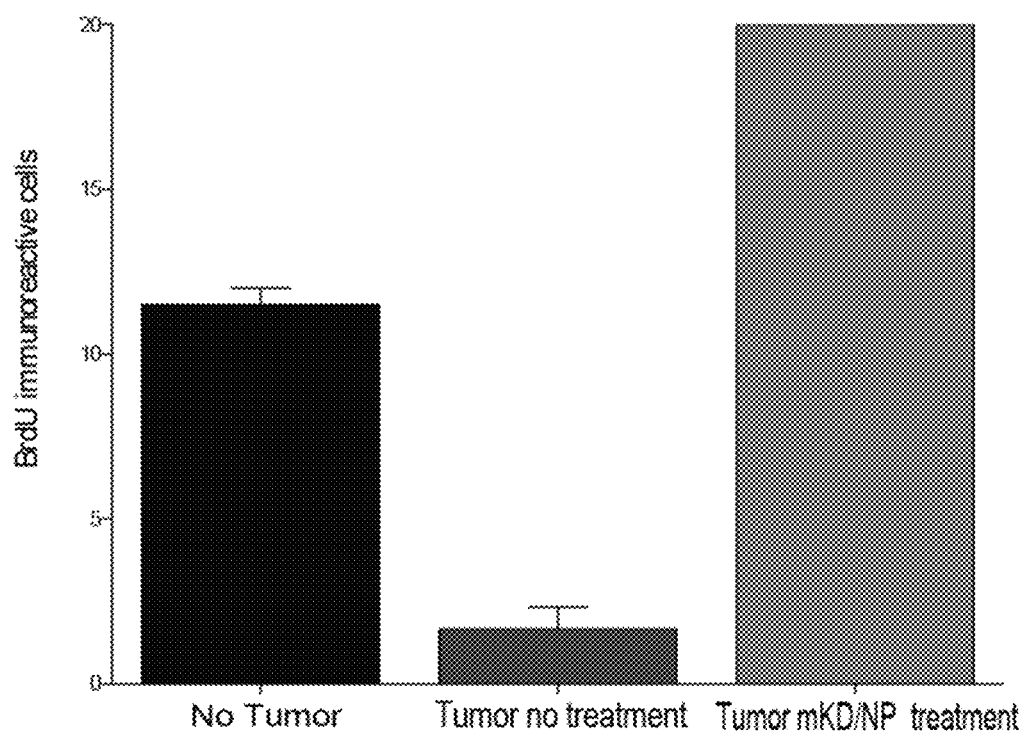
FIGS. 33A-33B: Effect of mKD/NP on neural stem cell (NSC) activity.

When tumors reached end point, animals received three injections of BrdU [50 mg/kg] over a 72-hour time period. Animals were killed, brains removed, fixed, sectioned and BrdU antibodies used to identify cells that were in S-phase during the 72 hour injection period. The number of BrdU-immunoreactive cells were enumerate in the dentate gyrus of the hippocampus. FIG. 33A reveals that relative to normals [non-tumor bearing animals], peripheral tumors caused a dramatic and significant reduction in the number of proliferating cells. However, in animals treated with mKD/NP diet there was a striking increase in the number of proliferating dentate gyrus stem cells. These data indicate that the mKD/NP treatment is able to protect the endogenous neural stem cells from the negative effects of a tumor located outside of the CNS. Given the growing body of literature demonstrating cognitive impairment in cancer patients, this data supports the use of the mKD/NP diet for maintaining normal brain function and memory.

Figure 33B:
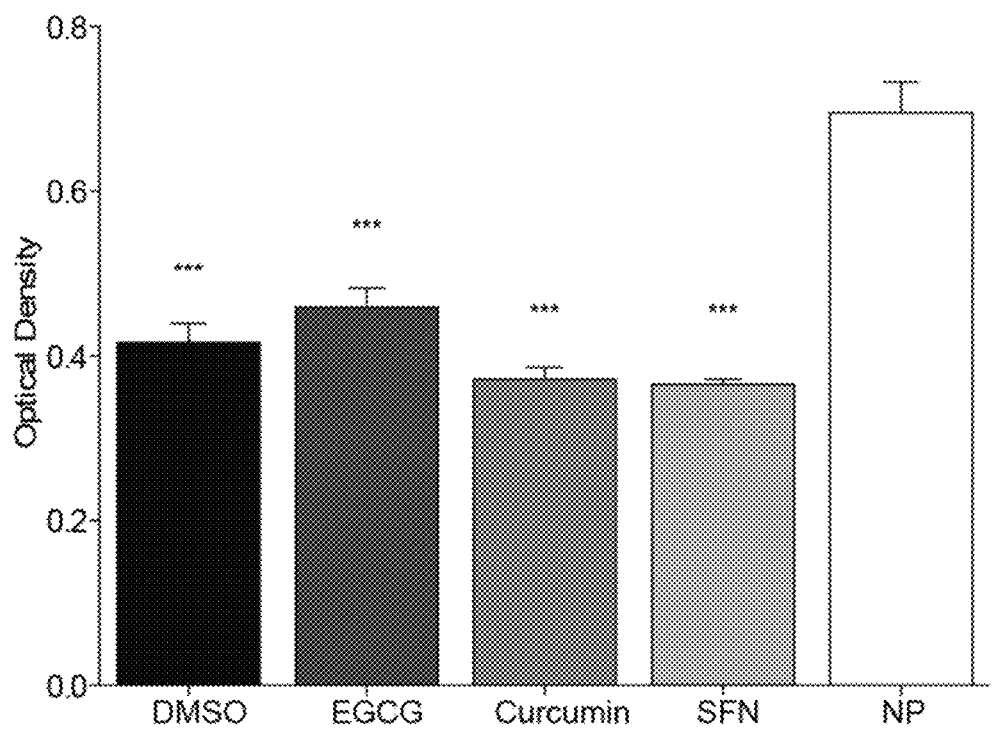

When somatic human neural stem cells (hNSCs) were cultured in vitro using the Neurosphere Assay and treated with each of the individual natural products ([1] EGCG-8 µM, 2] Curcumin-0.5 µM or [3] SFN-2.5 µM) or the combination of all three, each natural product on its own did not show any effect on the viability of hNSCs (analyzed using the standard MTT assay). However, the combination of all three natural products exhibited a significantly increased viability [FIG. 33B].

Together these data support the notion that mKD/NP and NP represent unique combinations able to efficiently enhance and maintain the pool of somatic neural stem cells both in vitro and in vivo.

Example 15: Optimization of the mKD/NP Diet

To improve the effectiveness of the mKD/NP diet we investigated the addition of Daikon Radish Sprout Powder [DRSP]. NOD-SCID animals were inoculated with 1M patient derived GB cells and once a palpable tumor was identified animals were randomized into 1 or 3 groups:
[1] Control diet: Is a standard mouse chow and is composed of 55% carbohydrate, 30% protein, 15% fat.
[2] mKD/NP.001: 10% carbohydrate, 60% Fat (half coming from medium chain triglycerides [MCT, Neobee 598]), 30% Protein+SFN (25 mg/kg; BSP100%), Curcumin (1200 mg/kg), EGCG (1200 mg/kg).
[3] mKD/NP.002: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg).

Figure 34:
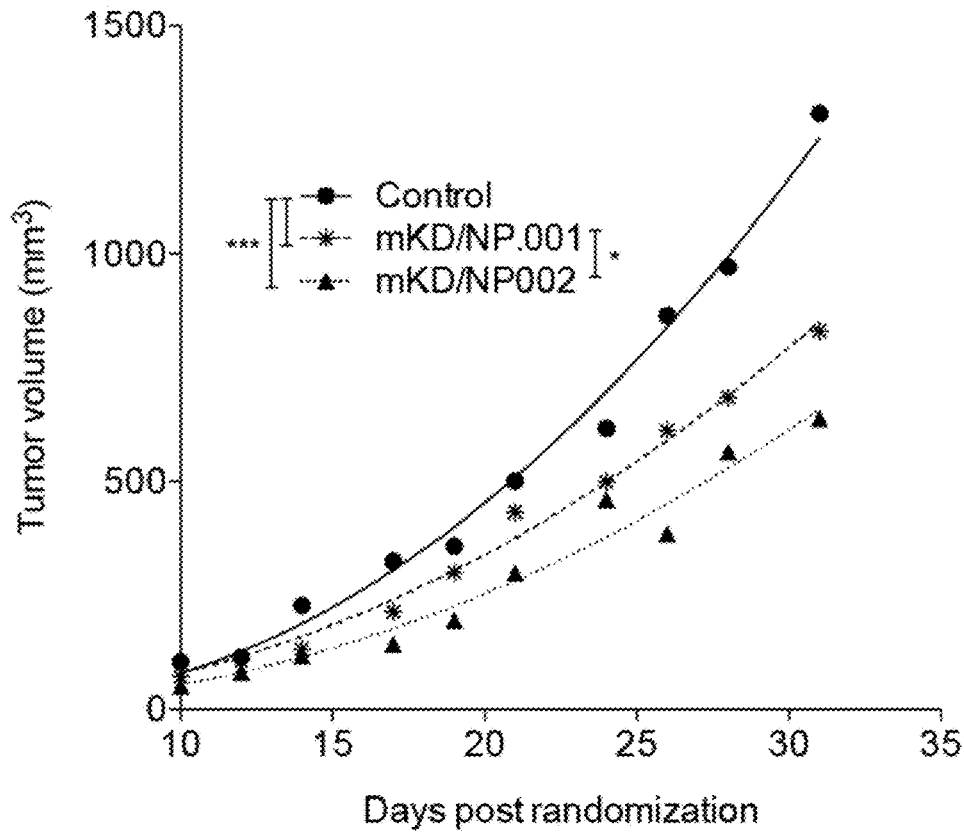
FIG. 34: Optimization mKD/NP—Tumor progression. The presence of Daikon Radish Sprout Powder (DRSP)

Tumor volume was measured three times per week using calipers. FIG. 34 demonstrates that mKD/NP.002 had a significant effect on reducing tumor progression relative to the control [$p<0.001$] and was statistically significantly better than mKD/NP.001 [$p<0.05$]. Similarly, the time for a palpable tumor to reach a volume of 300 mm3 was significantly delayed in the mKD/NP.002 fed animals in comparison to mKD/NP.001 group [FIG. 35]. Importantly, mean survival was enhanced in the mKD/NP.002 treated animals relative to mKD/NP.001 group [FIG. 36, $p<0.05$].

Once animals had reached end point the tumors were surgically excised and dissociated into a single cell suspension so they could be analyzed by using flow cytometry. The cells were fixed [4% PFA] and processed for immunohistochemistry using an antibody that identified the cell proliferation antigen Ki67 and pSTAT3 (pathway activated in GB that is a number one driver of uncontrolled proliferation). FIG. 37A illustrates a significant reduction in the percentage of cells that are actively dividing in the mKD/NP.002 group compared to mKD/NP.001 [p<0.05] and control [p<0.01]. Similarly, there was a marked reduction in the percentage of GB cells with activated STAT3 signaling as evidenced by the reduction in the number of pSTAT3 immunoreactive cells [FIG. 37B].

Example 16: mKD/NP Treatment is an Effective Therapy for Colon Cancer

Using a colorectal adenocarcinoma cell line [HT-29], 2M cells were implanted into the right flank of NOD/SCID animals. Once a palpable tumor was noted, animals were randomly assigned to one of two groups:

[1] Control diet: Is a standard mouse chow and is composed of 55% carbohydrate, 30% protein, 15% fat.

[2] mKD/NP: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg).

Tumors were measured 3 times/week and animals sacrificed once the tumors reach endpoint [1000 mm3]. Tumor volume was measured over time and FIG. 38 indicates a significant reduction in tumor progression for the mKD/NP treated animals. The effects of mKD/NP on delaying tumor progression are further reflected in FIG. 39 where tumor volume was compared between the control and the treated group 30 days after tumor inoculation. In this case there was a significant reduction in the mean tumor volume [student's t-test, p<0.01].

Importantly, Kaplan-Meier survival curves demonstrated that the mKD/NP treated animals survive significantly longer than the controls [FIG. 40, p<0.01, Log rank test], which was also reflected in the meantime to reach endpoint [FIG. 41].

When colon cancer cells were treated in vitro with each of the individual natural products, or the combination of all three, each natural product on its own exhibited a significant reduction in the number of cells that were generated. However, the combination of all three natural products demonstrated the largest reduction in cell numbers.

Together these data support the notion that mKD/NP and NP are able to reduce the proliferation of colon cancer both in vitro and in vivo.

Example 17: mKD/NP Treatment is an Effective Therapy for Lung Cancer

Using a lung carcinoma cells (A549), 2M cells were implanted into the right flank of NOD/SCID animals. Once a palpable tumor was noted, animals were randomly assigned to one of two groups:

[1] Control diet: Is a standard mouse chow and is composed of 55% carbohydrate, 30% protein, 15% fat.

[2] mKD/NP: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg).

Tumors were measured 3 times/week and animals sacrificed once the tumors reach endpoint [1000 mm3]. Tumor volume was measured over time and FIG. 43 demonstrates a significant reduction in tumor progression for the mKD/NP treated animals [p<0.001]. The effects of mKD/NP on delaying tumor progression are further reflected in FIG. 44 where tumor volume was compared between the control and the treated group 31 days after treatment initiation. In this case there was a significant reduction in the mean tumor volume [student's t-test, p<0.05]. The progression free survival of the tumors was determined by measuring the time it took tumors to go from a palpable stage to a size of 300 mm3. In this case the progression free survival was significantly delayed in the mKD/NP group [FIG. 45]. Importantly, Kaplan-Meier survival curves demonstrated that the mKD/NP treated animals survive significantly longer than the controls [FIG. 46, p<0.05, Log rank test], which was also reflected in the meantime to reach endpoint [FIG. 47].

When colon cancer cells were treated in vitro with each of the individual natural products, or the combination of all three, each natural product on its own exhibited a significant reduction in the number of cells that were generated. However, the combination all three natural products demonstrated the greatest reduction in cell numbers [FIG. 48].

Together these data support the notion that mKD/NP and NP are able to reduce the proliferation of colon cancer both in vitro and in vivo and that this unique combination is an effective cancer treatment.

Example 18: mKD/NP Treatment is an Effective Therapy for Breast Cancer

Human breast cancer cells [ZR751] grown in culture and treated daily with physiological concentrations of either EGCG (8 µM), Curcumin (0.5 µM) or SFN (2.5 µM) or used in combination (NP). Once the control cultures had reached confluency, cell numbers were determined using the standard MTT Assay. FIG. 49 reveals that each of the NPs on their own had no statistically significant effect on reducing the number of breast cancer cells, however, the combination of all three NPs reduced the number of cells by nearly 40%.

Next 2M ZR751 breast cancer cells were implanted into the flank of a NOD/SCID mouse and host animals randomized into 1 of 2 groups once a detectable tumor could be palpated:

[1] Control diet: Is a standard mouse chow and is composed of 55% carbohydrate, 30% protein, 15% fat.

[2] mKD/NP: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg).

Tumors are measured 3 times per week using calipers and tumor volume is calculated using the following procedure. Tumor progression was followed by recording 2 measurements of tumor diameter and converting this into a volume using the following formula: $(4/3)\pi R3$. For spheroid tumors the two measurements were averaged to determine the diameter of the sphere. In the case of ellipsoid tumors (i.e. prolate or oblate spheroid mass) the formula used was: $(4/3)\pi*(d/2)*(d/2)2$. In this case the second measurement "d2" would count twice and "d" only once. For prolate spheroids, the long measurement occurs once while the short measurement occurs twice. Conversely, for the oblate spheroid tumors, the long measurement occurs twice while the short one occurs only once. Following these criteria, tumor volume was tracked over time. FIG. 50 depicts the progression of the tumor over time until the animals reached endpoint [1000 mm$^3$] and reveals that the mKD/NP diet results in a significant reduction in overall tumor progression [p<0.0001, two-way ANOVA]. The ability of mKD/NP to effectively reduce tumor progression is also reflected in comparing the mean size of the breast tumors at 70 and 145 days post treatment initiation. In this case, as depicted in FIGS. 51 and 52, there is an approximate 50% reduction in tumor size at day 70 [p<0.01, student t-test] and a similar reduction at Day 145, respectively.

Progression free survival was determined by calculating the time it took the tumors to grow from a barely palpable stage [approximately 65 mm$^3$] to a tumor of significant size [visually identifiable, 300 mm$^3$]. In this case, the mKD/NP diet produced an approximate 20% increase in progression free survival [FIG. 53, p<0.01, students t-test]. Importantly, comparison of the survival curves [Kaplan-Meier] between the two groups indicate that the mKD/NP diet resulted in a statistically significant increase in survival [FIG. 53, p<0.01, log rank test].

Together these data demonstrate the effectiveness of mKD/NP at treating an aggressive and deadly form of breast cancer.

Example 19: Mechanisms of mKD/NP: Cell Death, Cancer Stem Cells and DNA Damage

Using patient derived GB cells that were expended in culture, 1M were implanted into the right flank of NOD/SCID animals. Once a palpable tumor was identified animals were randomized to one of two treatment groups:

[1] Control diet: Is a standard mouse chow and is composed of 55% carbohydrate, 30% protein, 15% fat.

[2] mKD/NP: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg).

Tumors were monitored 3 times per week and animals sacrificed when they reached endpoint [1500 mm$^3$]. Tumors were harvested and prepared [fixed and labeled with DAPI] for identification of the SubG1 population, which is representative of the apoptotic subpopulation. The percentage of cells undergoing cell death is significantly increased in the mKD/NP treated animals [FIG. 55, p<0.001, student t-test].

CD133 is a prospective marker for GB cancer stem cells where an increase in their frequency is indicative of a more aggressive or more difficult to treat tumor. Development of therapies that are able to target this population and reduce the frequency of CD133 positive cells or cancer stem cells are thought to be a critical component in the development of more effective therapeutics. Using the paradigm details in this example, we probed the control and mKD/NP treated tumors with a CD133 specific antibody so as to calculate the overall percentage of CD133-positive cancer stem cells. FIG. 56 depicts the results from one particular experiment where we noted a 60% reduction in the size of the CD133-positive cancer stem cell population. It was also noted, FIG. 57, in the mKD/NP treated animals that the CD133-positive cancer stem cells contained notable double-stranded DNA breaks approximately 3 times than the control treated animals [this was determined using an antibody that marks the phosphorylated form of H2AX, which is positively correlated to the amount of DNA double-stranded breaks].

Together these data demonstrate the ability of mKD/NP to not only increase the incidence of apoptotic cell death but to importantly target GB cancer stem cells by increasing the amount of DNA damage in this particular and clinically relevant subpopulation.

Example 20: mKD/NP Targets Known Drivers of Tumor Proliferation and Mechanisms that Afford Resistance to Conventional Treatments Using cell lines that were derived from patient tumors and cultured in serum free media, 1M GB cells were implanted into the right flank of NOD/SCID animals. Once a palpable tumor was identified animals were randomized to one of two treatment groups:

[1] Control diet: Is a standard mouse chow and is composed of 55% carbohydrate, 30% protein, 15% fat.

[2] mKD/NP: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg).

Tumor volume was monitored 3 times per week using calipers and animals were sacrificed when they reached endpoint [1500 mm$^3$], tumors excised and cells processed for immunohistochemistry and identification of intracellular pathway activation. Analysis was performed using flow cytometry. FIG. 58 summarizes the effects of mKD/NP on the expression [FIG. 58A] and activation [FIG. 58B] of Y-box binding protein 1 [YB1], a protein that is implicated in the maintenance and proliferation of tumor cells [including brain and breast tumors]. The data in FIG. 58 demonstrates a significant reduction in overall YB1 expression and in the number of cells that demonstrate phosphorylation, and hence activation, of YB1 [FIGS. 58A and B, respectively].

Within this same experimental series we also assessed the CD133+ cancer stem cell population and levels of the anti-apoptotic effector NFkB [FIG. 59] and noted a marked reduction of over 80% in the percentage of cancer stem cells that were expressing NFkB. This demonstrates the ability of mKD/NP to target the anti-apoptotic mechanisms that cancer stem cells use to survive conventional treatments.

In summary, the data from these experiments demonstrate that mKD/NP targets known drivers of tumor proliferation and anti-apoptotic mechanisms and together provide a better mechanistic understanding of the target[s] of mKD/NP.

Example 21: mKD/NP Attenuates Chemotherapy Induced Upregulation of Proteins that Contribute to Treatment Resistance Patient derived GB cells were cultured in the NeuroSphere Assay [using defined culture conditions]. The cells were treated daily for 4 of their seven days in culture with one of the following:

[1] Control

[2] TMZ [10 μM]

[3] NP combination [EGCG (8 μM), Curcumin (0.5 μM) and sulforaphane (2.5 μM)]

[4] TMZ [10 μM] & NP combination [EGCG (8 μM), Curcumin (0.5 μM) and sulforaphane (2.5 μM)]

After seven days in culture cells were harvested, fixed with 4% PFA, processed for immunocytochemistry and analyzed by flow cytometry. FIG. 60 depicts the increase in MGMT levels in cells that are treated with TMZ [approximately 30%] and the attenuation of this increase [less than 10% of the control levels] when the TMZ treated cultures were also treated with the NP combination. FIG. 61 depicts the changes in overall survivin expression [a member of the inhibitor of apoptosis for which the overexpression is associated with chemoresistance] within the population and the number of survivin expressing cells. While TMZ resulted in a statistically significant increase in the overall expression of survivin and in the number of cells that expressed it, the addition of NP returned the levels back to those that were comparable to control. Interestingly, NP on its own did not affect the expression of survivin compared to the control cells.

Following inoculation of 1M GB cells into the right flank of NON/SCID animals, and their randomization into one of two treatment groups, animals were treated with one of two diets:

[1] Control diet: Is a standard mouse chow and is composed of 55% carbohydrate, 30% protein, 15% fat.

[2] mKD/NP: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg).

When animals reached endpoint they were sacrificed, tumors removed, dissociated into a single cell suspension, fixed in 4% PFA and analyzed by flow cytometry for MGMT or pSTAT3 expression. FIG. 62 summarized the results of this experiment and teaches that MGMT [FIG. 61A] and pSTAT3 [FIG. 61B] levels markedly reduced when treated with mKD/NP relative to controls. As both elevated MGMT and pSTAT are mechanism correlated and known to increase resistance to chemotherapy, mKD/NP demonstrates a promising approach to decrease the expression levels of these proteins and sensitize cells to chemotherapy.

In summary, the experiments in this example provide a mechanism for our observed reduction in tumor progression, increased survival and enhanced response to chemotherapy.

Example 22: Mechanism for mKD/NP Therapeutic Effect on Reducing Tumor Progression and Enhancing Survival FIGS. 63-66 illustrates a number of mechanisms that mKD/NP diet can influence to reduce tumor progression and increase life span. Following inoculation of 1M GB cells into the right flank of NON/SCID animals, and randomization into one of two treatment groups, animals were treated with one of two diets:

[1] Control diet: Is a standard mouse chow and is composed of 55% carbohydrate, 30% protein, 15% fat.

[2] mKD/NP: 10% carbohydrate, 60% Fat (half coming from medium chain triglycerides [MCT, Neobee 598]), 30% Protein+SFN (25 mg/kg; BSP95%/DRSP5%), Curcumin (1200 mg/kg), EGCG (1200 mg/kg).

When tumors reached endpoint the animals were sacrificed, tumors removed, dissociated into a single cell suspension, fixed in 4% PFA and analyzed by flow cytometry [FIGS. 63, 64, 65 & 66], immunohistochemisty [FIG. 66B] and western blots [FIG. 66D]. Together, these data illustrate that mKD/NP diet is able to reduce the expression of many of the drivers of tumor progression including ZEB1 [FIG. 63], mTOR [FIG. 66], those that enhance survival such as NFkB [FIG. 64]. mKD/NP diet is also able to target a key protein involved in glucose metabolism that is upregulated in GB and that plays a key role in providing glucose, and hence fuel, to actively proliferating GB cells [FIG. 65].

These data support the broad effect that mKD/NP has on tumor cells and its ability to simultaneously target multiple mechanisms that play a role in altering the primary drivers of tumor progression but also the escape mechanisms that are responsible for inherent and acquired tumor resistance.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

Deleyrolle, L. P., Harding, A., Cato, K., Siebzehnrubl, F. A., Rahman, M., Azari, H., et al. (2011). Evidence for label-retaining tumour-initiating cells in human glioblastoma. *Brain.*, pp. 1-13.

Redon, C. E., Dickey, J. S., Nakamura, A. J., Kareva, I. G., Naf, D., Nowsheen, S., et al. (2010). Tumors induce complex DNA damage in distant proliferative tissues in vivo. *Proceedings of the National Academy of Sciences of the United States of America,* 107(42), 17992-17997.

Sherry, M. M., Reeves, A., Wu, J. K., & Cochran, B. H. (2009). STAT3 is required for proliferation and maintenance of multipotency in glioblastoma stem cells. *Stem Cells* (Dayton, Ohio), 27(10), 2383-2392.

Fotovati, A., Abu-Ali, S., Wang, P.-S., Deleyrolle, L. P., Lee, C., Triscott, J., et al. (2011). YB-1 Bridges Neural Stem Cells and Brain Tumor-Initiating Cells via Its Roles in Differentiation and Cell Growth. *Cancer Research,* 71(16), 5569-5578.

Gao, Y., Fotovati, A., Lee, C., Wang, M., Cote, G., Guns, E., et al. (2009). Inhibition of Y-box binding protein-1 slows the growth of glioblastoma multiforme and sensitizes to temozolomide independent 06-methylguanine-DNA methyltransferase. *Molecular Cancer Therapeutics,* 8(12), 3276-3284.

Kohsaka, S., Wang, L., Yachi, K., Mahabir, R., Narita, T., Itoh, T., et al. (2012). STAT3 inhibition overcomes temozolomide resistance in glioblastoma by downregulating MGMT expression. *Molecular Cancer Therapeutics,* 11(6), 1289-1299.

Boado, R J., Black, K L., Pardrige, W M. Gene expression of GLUT3 and GLUT1 glucose transporters in human brain tumors. (1994). Gene expression of GLUT3 and GLUT1 glucose transporters in human brain tumors. *Brain Res Mol Brain Res,* 27(1), 51-57.

Le Calvé, B., Rynkowski, M., Le Mercier, M., Bruyere, C., Lonez, C., Gras, T., et al. (2010). Long-term in vitro treatment of human glioblastoma cells with temozolomide increases resistance in vivo through up-regulation of GLUT transporter and aldo-keto reductase enzyme AKR1C expression. *Neoplasia* (New York, NY), 12(9), 727-739.

F. A. Siebzehnrubl, D. J. Silver, B. Tugertimur, L. P. Deleyrolle, D. Siebzehnrubl, M. R. Sarkisian, K. G. Devers, A. T. Yachnis, M. D. Kupper, D. Neal, NH Nabilsi, M. P. Kladde, O. Suslov, S. Brablertz, T. Brabletz, B. A. Reynolds, D. A. Steindler. A single pathway linking invasion, chemoresistance and tumor initiation in glioblastoma. *Under review.*

We claim:

1. A method of treating a subject for a proliferative disease, comprising administering to the subject having the proliferative disease, each of (i), (ii), and (iii):
   (i) a composition comprising epigallocatechin-3-gallate,
   (ii) a composition comprising curcumin, and
   (iii) a composition comprising glucoraphanin and/or sulforaphane (SFN),
   wherein (i), (ii), and (iii) are administered individually or as a single composition, and, optionally, providing a modified ketogenic diet or a ketogenic diet to the subject, wherein the proliferative disease is cancer selected from the group consisting of brain cancer, breast cancer, colon cancer, and lung cancer.

2. The method of claim 1, further comprising administering to the subject Daikon radish sprout, a Daikon radish sprout extract or a powder of said extract or the Daikon radish sprout.

3. The method of claim 1, wherein the method further comprises an additional therapy or therapies to treat the proliferative disease.

4. The method of claim 3, wherein the additional therapy or therapies to treat the proliferative disease are selected from radiotherapy, chemotherapy, surgery, immunotherapy, and/or monoclonal antibody therapy.

5. The method of claim 4, wherein the additional therapy or therapies comprise(s) administering one or more compounds selected from abiraterone acetate, methotrexate, paclitaxel albumin-stabilized nanoparticle formulation, a combination of doxorubicin hydrochloride, bleomycin sulfate, vinblastine sulfate, and dacarbazine, a combination of doxorubicin hydrochloride, bleomycin sulfate vincristine sulfate, and etoposide, a combination of doxorubicin hydrochloride, bleomycin sulfate, vincristine sulfate, etoposide, prednisone, and cyclophosphamide, a combination of doxorubicin hydrochloride and cyclophosphamide, a regimen of a combination of doxorubicin hydrochloride and cyclophosphamide followed by paclitaxel, brentuximab vedotin, a combination of cytarabine, daunorubicin, and etoposide, doxorubicin hydrochloride, fluorouracil, everolimus, imiquimod, aldesleukin, alemtuzumab, pemetrexed disodium, palonosetron hydrochloride, chlorambucil, chlorambucil, aminolevulinic acid, anastrozole, aprepitant, anastrozole, exemestane, nelarabine, arsenic trioxide, ofatumumab, asparaginase Erwinia chrysanthemi, bevacizumab, axitinib, azacitidine, a regimen of bleomycin, etoposide, doxorubicin hydrochloride, cyclophosphamide, vincristine, procarbazine, and prednisone, bendamustine hydrochloride, a combination of bleomycin, etoposide, and cisplatin, bevacizumab, bexarotene, tositumomab and I 131 iodine tositumomab, bleomycin, bortezomib, bosutinib, brentuximab vedotin, cabazitaxel, cabozantinib-S-malate, a combination of cyclophosphamide, doxorubicin hydrochloride, and fluorouracil, alemtuzumab, irinotecan hydrochloride, capecitabine, a combination of oxaliplatin and capecitabine, carboplatin, a combination of carboplatin and paclitaxel, carfilzomib, lomustine, daunorubicin hydrochloride, recombinant HPV bivalent vaccine, cetuximab, chlorambucil, a combination of chlorambucil and prednisone, a combination of cyclophosphamide, doxorubicin hydrochloride, vincristine sulfate, and prednisone, cisplatin, cyclophosphamide, clofarabine, a combination of cyclophosphamide, methotrexate, and fluorouracil, cabozantinib-S-Malate, a combination of cyclophosphamide, oncovin, procarbazine, and prednisone, dactinomycin, crizotinib, a combination of cyclophosphamide, vincristine sulfate, and prdnisone, cyclophosphamide, ifosfamide, cytarabine, liposomal cytarabine, cyclophosphamide, dacarbazine, decitabine, dactinomycin, dasatinib, daunorubicin hydrochloride, degarelix, denileukin, denosumab, liposomal cytarabine, liposomal cytarabine, dexrazoxane hydrochloride, docetaxel, doxorubicin hydrochloride liposome, doxorubicin hydrochloride, doxorubicin hydrochloride liposome, dacarbazine, fluorouracil, rasburicase, epirubicin hydrochloride, oxaliplatin, eltrombopag olamine, aprepitant, enzalutamide, epirubicin hydrochloride, a combination of etoposide, prednisone, vincristine, cyclophosphamide, and doxorubicin hydrochloride, cetuximab, eribulin mesylate, vismodegib, erlotinib hydrochloride, etoposide phosphate, etoposide, doxorubicin hydrochloride liposome, everolimus, raloxifene hydrochloride, exemestane, toremifene, fulvestrant, a combination of 5-fluorouracil, epiodoxorubicin, and cyclophosphamide, letrozole, filgrastim, fludarabine phosphate, fluorouracil, methotrexate, a combination of calcium folinate, 5-fluorouracil, and irinotecan hydrochloride, and bevacizumab, a, a combination of leucovorin calcium, fluorouracil, irinotecan hydrochloride, and oxaliplatin, a combination of leucovorin calcium, fluorouracil, and oxaliplatin, pralatrexate, a combination of fluorouracil and leucovorin calcium, recombinant HPV quadrivalent vaccine, gefitinib, gemcitabine hydrochloride, a combination of gemcitabine and cisplatin, gemtuzumab ozogamicin, imatinib mesylate, glucarpidase, eribulin mesylate, trastuzumab, human papillomavirus bivalent vaccine (recombinant), human papillomavirus quadrivalent vaccine (recombinant), topotecan hydrochloride, ibritumomab tiuxetan, a combination of carboplatin, etoposide, and ifosfamide, ponatinib hydrochloride, ifosfamide, imatinib mesylate, imiquimod, axitinib, ipilimumab, gefitinib, irinotecan hydrochloride, romidepsin, ixabepilone, ruxolitinib phosphate, cabazitaxel, raloxifene hydrochloride, palifermin, carfilzomib, lapatinib ditosylate, lenalidomide, letrozole, leucovorin calcium, chlorambucil, leuprolide acetate, aminolevulinic acid, chlorambucil, doxorubicin hydrochloride liposome, liposomal cytarabine, lomustine, leuprolide acetate, vincristine sulfate liposome, procarbazine hydrochloride, mechlorethamine hydrochloride, mesna, temozolomide, methotrexate, mitomycin C, a regimen of mechlorethamine, vincristine, procarbazine, and prednisone, plerixafor, mechlorethamine hydrochloride, azacitidine, gemtuzumab ozogamicin, vinorelbine tartrate, nelarabine, cyclophosphamide, filgrastim, sorafenib tosylate, nilotinib, tamoxifen citrate, romiplostim, ofatumumab, omacetaxine, mepesuccinate, pegaspargase, denileukin diftitox, oxaliplatin, palifermin, palonosetron hydrochloride, panitumumab, carboplatin, pazopanib hydrochloride, pegaspargase, pemetrexed disodium, pertuzumab, cisplatin, plerixafor, ponatinib hydrochloride, pralatrexate, prednisone, procarbazine hydrochloride, aldesleukin, denosumab, eltrombopag olamine, sipuleucel-T, raloxifene hydrochloride, rasburicase, a combination of rituximab, cyclophosphamide, doxorubicin hydrochloride, vincritstine sulfate, and prednisone, a combination of rituximab, cyclophosphamide, vincritstine sulfate, and prednisone, recombinant HPV bivalent vaccine, recombinant HPV, quadrivalent vaccine, regorafenib, lenalidomide, methotrexate, rituximab, romidepsin, romiplostim, daunorubicin hydrochloride, ruxolitinib phosphate, talc, sipuleucel-T, sorafenib tosylate, dasatinib, a combination of mechlorethamine, doxorubicin hydrochloride, vinblastine sulfate, vincristine sulfate, bleomycin, etoposide phosphate, and prednisone, sterile talc powder, regorafenib, sunitinib malate, thalidomide, omacetaxine mepesuccinate, tamoxifen citrate, cytarabine, erlotinib hydrochloride, bexarotene, nilotinib, paclitaxel, docetaxel, temozolomide, thalidomide, topotecan hydrochloride, toremifene, temsirolimus, dexrazoxane hydrochloride, bendamustine hydrochloride, lapatinib ditosylate, vandetanib, a combination of vincristine sulfate, doxorubicine hydrochloride, methotrexate, and prednisone, panitumumab, a combination of etoposide, ifosfamide, and cisplatin, vinblastine sulfate, bortezomib, vemurafenib, leuprolide acetate, azacitidine, vincristine sulfate, vincristine sulfate liposome, vinorelbine tartrate, vismodegib, glucarpidase, vorinostat, pazopanib hydrochloride, leucovorin calcium, crizotinib, capecitabine, a combination of capecitabine and oxaliplatin, denosumab, enzalutamide, ipilimumab, ziv-aflibercept, vemurafenib, ibritumomab tiuxetan, dexrazoxane hydrochloride, ziv-aflibercept, vorinostat, zoledronic acid, or abiraterone acetate.

6. The method of claim 1, wherein said method comprises providing to the subject both a modified ketogenic diet or a ketogenic diet, and a composition comprising epigallocatechin-3-gallate, a composition comprising curcumin, and a composition comprising glucoraphanin and/or sulforaphane (SFN).

7. The method of claim 1, wherein the composition of (iii) comprises glucoraphanin.

8. The method of claim 1, wherein (i), (ii), and (iii) are administered together as a single composition.

9. The method of claim 2, wherein the Daikon radish sprout, Daikon radish sprout extract or powder of the extract or of the Daikon radish sprout is administered to the subject together with (i), (ii), and (iii), as a single composition.

10. The method of claim 1, wherein the composition of (iii) comprises SFN.

11. The method of claim 1, wherein the composition of (iii) is in the form of broccoli sprout powder.

12. The method of claim 1, wherein (i), (ii), and (iii) are administered together as a single composition, and wherein the composition of (iii) comprises glucoraphanin.

13. The method of claim 1, wherein (i), (ii), and (iii) are administered together as a single composition, and wherein the composition of (iii) comprises SFN.

14. The method of claim 1, wherein (i), (ii), and (iii) are administered by ingestion.

* * * * *